(12) United States Patent
Contag et al.

(10) Patent No.: US 8,460,906 B2
(45) Date of Patent: Jun. 11, 2013

(54) IMMOBILIZED PRODUCT TOLERANT MICROORGANISMS

(75) Inventors: Pamela Reilly Contag, San Jose, CA (US); Stacy M. Burns-Guydish, Campbell, CA (US); Hendrikus J. Meerman, Scotts Valley, CA (US); David C. Walther, Oakland, CA (US); John C. Chen, Bethlehem, PA (US); Alvin W. Nienow, Edgbaston (GB); Ian Maddox, Eden Terrace (NZ)

(73) Assignee: Cobalt Technologies, Inc., Mountain View, CA (US)

( * ) Notice: Subject to any disclaimer, the term of this patent is extended or adjusted under 35 U.S.C. 154(b) by 0 days.

(21) Appl. No.: 12/936,611

(22) PCT Filed: Apr. 9, 2009

(86) PCT No.: PCT/US2009/040050
§ 371 (c)(1),
(2), (4) Date: Dec. 22, 2010

(87) PCT Pub. No.: WO2009/126795
PCT Pub. Date: Oct. 15, 2009

(65) Prior Publication Data
US 2011/0129887 A1 Jun. 2, 2011

Related U.S. Application Data

(60) Provisional application No. 61/043,710, filed on Apr. 9, 2008.

(51) Int. Cl.
C12P 7/16 (2006.01)
C12P 1/04 (2006.01)
C12P 1/00 (2006.01)
C12M 1/00 (2006.01)

(52) U.S. Cl.
USPC ........... 435/160; 435/289.1; 435/170; 435/41

(58) Field of Classification Search
None
See application file for complete search history.

(56) References Cited

U.S. PATENT DOCUMENTS

| | | |
|---|---|---|
| 2,487,884 A | 11/1949 | Lunt |
| 3,004,089 A | 10/1961 | Hutto |
| 3,390,057 A | 6/1968 | Day |
| 3,875,019 A | 4/1975 | Cocuzza et al. |
| 4,186,058 A | 1/1980 | Katz et al. |
| 4,282,067 A | 8/1981 | Katz et al. |
| 4,309,254 A | 1/1982 | Dahlstrom et al. |
| 4,319,964 A | 3/1982 | Katz et al. |
| 4,326,032 A | 4/1982 | Grove |
| 4,356,196 A | 10/1982 | Hultquist |
| 4,398,920 A | 8/1983 | Guibet et al. |
| 4,424,275 A | 1/1984 | Levy |
| 4,440,601 A | 4/1984 | Katz et al. |
| 4,443,542 A | 4/1984 | Hayashida et al. |
| 4,520,104 A | 5/1985 | Heady |
| 4,539,293 A | 9/1985 | Bergstrom et al. |
| 4,560,658 A | 12/1985 | Datta et al. |
| 4,568,643 A | 2/1986 | Levy |
| 4,600,477 A | 7/1986 | Higashi et al. |
| 4,615,769 A | 10/1986 | Horigome et al. |
| 4,628,116 A | 12/1986 | Cenedella |
| 4,649,112 A | 3/1987 | Datta et al. |
| 4,671,856 A | 6/1987 | Sears |
| 4,757,010 A | 7/1988 | Hermann et al. |
| 4,769,113 A | 9/1988 | Sears |
| 4,777,135 A | 10/1988 | Husted et al. |
| 4,869,067 A | 9/1989 | Sears |
| 4,902,197 A | 2/1990 | Rhodes et al. |
| 4,919,592 A | 4/1990 | Sears et al. |
| 4,978,429 A | 12/1990 | Sears et al. |
| 5,063,156 A | 11/1991 | Glassner et al. |
| 5,124,004 A | 6/1992 | Greithlein et al. |
| 5,192,673 A | 3/1993 | Jain et al. |
| 5,210,032 A | 5/1993 | Kashket |
| 5,229,285 A | 7/1993 | Kajiyama et al. |
| 5,292,658 A | 3/1994 | Cormier et al. |
| 5,411,594 A | 5/1995 | Brelsford |
| 5,418,155 A | 5/1995 | Cormier et al. |
| 5,491,084 A | 2/1996 | Chalfie et al. |
| 5,563,069 A | 10/1996 | Yang |
| 5,595,893 A | 1/1997 | Pometto et al. |
| 5,597,453 A | 1/1997 | Sears |
| 5,604,123 A | 2/1997 | Kazami et al. |
| 5,618,722 A | 4/1997 | Zenno et al. |
| 5,625,048 A | 4/1997 | Tsien et al. |
| 5,641,641 A | 6/1997 | Wood |
| 5,650,135 A | 7/1997 | Contag et al. |
| 5,650,289 A | 7/1997 | Wood |
| 5,670,356 A | 9/1997 | Sherf et al. |
| 5,753,474 A | 5/1998 | Ramey |
| 5,755,967 A | 5/1998 | Meagher et al. |
| 5,777,079 A | 7/1998 | Tsien et al. |
| 5,804,387 A | 9/1998 | Cormack et al. |
| 5,874,304 A | 2/1999 | Zolotukhin et al. |
| 5,968,321 A | 10/1999 | Sears |
| 5,968,738 A | 10/1999 | Anderson et al. |

(Continued)

FOREIGN PATENT DOCUMENTS

EP 0922106 B1 9/2005
EP 2072621 A1 6/2009

(Continued)

OTHER PUBLICATIONS

Huang et al. Continuous production of butanol by Clostridium acetobutylicum immobilized in a fibrous bed reactor, Appl Biochem and Biotechnol 2004, 113-116, 887-898.*

(Continued)

*Primary Examiner* — Anand Desai
*Assistant Examiner* — Iqbal H Chowdhury
(74) *Attorney, Agent, or Firm* — Wilson Sonsini Goodrich & Rosati

(57) ABSTRACT

Methods for mutagenizing and selecting microorganisms with increased product tolerance are provided. Additionally, methods and systems are disclosed for culturing the microorganisms to produce products.

38 Claims, 30 Drawing Sheets

U.S. PATENT DOCUMENTS

| | | | |
|---|---|---|---|
| 6,043,392 | A | 3/2000 | Holtzapple et al. |
| 6,066,476 | A | 5/2000 | Tsien et al. |
| 6,146,826 | A | 11/2000 | Chalfie et al. |
| 6,358,717 | B1 | 3/2002 | Blaschek et al. |
| 6,436,682 | B1 | 8/2002 | Bryan et al. |
| 6,617,156 | B1 | 9/2003 | Doucette-stamm et al. |
| 6,638,398 | B1 | 10/2003 | Ramm-schmidt et al. |
| 6,673,596 | B1 | 1/2004 | Sayler et al. |
| 6,733,997 | B1 | 5/2004 | Ding et al. |
| 6,737,245 | B1 | 5/2004 | Francis et al. |
| 6,841,158 | B1 | 1/2005 | Cotten et al. |
| 6,919,186 | B2 | 7/2005 | Stubbs et al. |
| 6,955,892 | B2 | 10/2005 | Lin et al. |
| 7,005,511 | B2 | 2/2006 | Tsien et al. |
| 7,056,728 | B2 | 6/2006 | Francis et al. |
| 7,090,976 | B2 | 8/2006 | Anderson |
| 7,109,005 | B2 | 9/2006 | Eroma et al. |
| 7,179,644 | B2 | 2/2007 | Farmer |
| 7,300,792 | B2 | 11/2007 | Gupta et al. |
| 7,354,743 | B2 | 4/2008 | Vlasenko et al. |
| 7,572,353 | B1 | 8/2009 | Vander Griend |
| 2003/0044951 | A1 | 3/2003 | Sporleder et al. |
| 2004/0142356 | A1 | 7/2004 | Patterson et al. |
| 2004/0248250 | A1 | 12/2004 | Nakai |
| 2005/0072662 | A1 | 4/2005 | Holtzapple et al. |
| 2005/0080248 | A1 | 4/2005 | Caldwell |
| 2005/0089979 | A1 | 4/2005 | Ezeji |
| 2005/0176121 | A1 | 8/2005 | Takeshita |
| 2005/0191723 | A1 | 9/2005 | Otte et al. |
| 2005/0285129 | A1 | 12/2005 | Jackson et al. |
| 2006/0010506 | A1 | 1/2006 | Otte et al. |
| 2006/0029958 | A1 | 2/2006 | Sakanyan et al. |
| 2006/0195935 | A1 | 8/2006 | Otte et al. |
| 2006/0263882 | A1 | 11/2006 | Fazio |
| 2007/0137996 | A1 | 6/2007 | Beckman |
| 2007/0215453 | A1 | 9/2007 | Eddington |
| 2007/0218541 | A1 | 9/2007 | Denney et al. |
| 2007/0259411 | A1 | 11/2007 | Bramucci et al. |
| 2008/0078205 | A1 | 4/2008 | Cuellar et al. |
| 2008/0248540 | A1 | 10/2008 | Yang |
| 2008/0293086 | A1 | 11/2008 | Contag |
| 2008/0299633 | A1 | 12/2008 | Rush |
| 2009/0081715 | A1 | 3/2009 | Burns-Guydish et al. |
| 2009/0155869 | A1 | 6/2009 | Buelter et al. |
| 2010/0330633 | A1 | 12/2010 | Walther et al. |

FOREIGN PATENT DOCUMENTS

| | | |
|---|---|---|
| JP | 63109766 A | 5/1988 |
| WO | WO 81/01012 A1 | 4/1981 |
| WO | WO 2007/041269 A2 | 4/2007 |
| WO | WO 2007/130560 A2 | 11/2007 |
| WO | WO 2008/006038 A2 | 1/2008 |
| WO | WO 2008/013996 A2 | 1/2008 |
| WO | WO 2007/041269 A3 | 6/2008 |
| WO | WO 2007/130560 A3 | 7/2008 |
| WO | WO 2008/082726 A2 | 7/2008 |
| WO | WO 2008/006038 A3 | 8/2008 |
| WO | WO 2008/013996 A3 | 10/2008 |
| WO | WO 2008/082726 A3 | 11/2008 |
| WO | WO 2009/033114 A2 | 3/2009 |
| WO | WO 2009/033114 A3 | 5/2009 |
| WO | WO 2009/120806 A2 | 10/2009 |
| WO | WO 2009/120806 A3 | 2/2010 |
| WO | WO 2010/027531 A1 | 3/2010 |
| WO | WO 2011/003962 A2 | 1/2011 |
| WO | WO 2011/003962 A3 | 3/2011 |

OTHER PUBLICATIONS

Almeida, et al. Increased tolerance and conversion of inhibitors in lignocellulosic hydrolysates by *Saccharomyces cerevisiae*. Journal of Chemical Technology & Biotechnology. 2007;82(4):340-349.

Alsaker, et al. Transcriptional analysis of spo0A overexpression in Clostridium acetobutylicum and its effect on the cell's response to butanol stress. J Bacteriol. Apr. 2004;186(7):1959-71.

Andersch, et al. Level of enzymes involved in acetate, butyrate, acetone and butanol formation by Clostridium acetobutylicum. Eur J Appl Microbiol Biotechnol. 1983; 18: 327-32.

Araki, et al. Continuous fermentation by butanol-isopropanol by Butanol-Isopropanol Producing Microorganisms Immobilized by Ca-Alginate. J Soc Fermentation and Bioengineering. 1993. 71(1):9-14. (in Japanese with English abstract).

Baer, et al. Effect of Butanol Challenge and Temperature on Lipid Composition and Membrane Fluidity of Butanol-Tolerant Clostridium acetobutylicum. Appl Environ Microbiol. Dec. 1987;53(12):2854-2861.

Bahl, et al. Continuous production of acetone and butanol by Clostridium acetobutylicum in a two-stage phosphate limited chemostat. Eur J Appl Microbiol Biotechnol. 1982; 15: 201-5.

Bahl, et al. Nutritional factors affecting the ratio of solvents produced by Clostridium acetobutylicum. Appl Environ Microbiol 1986; 52(1): 169-72.

Bahl, et al. Parameters affecting solvent production by Clostridium acetobutylicum in continuous culture. In: Wang, et al., ed. Biotechnology and Bioengineering Symposium No. 14, Sixth Symposium on Biotechnology for Fuels and Chemicals. New York, NY: John.

Beesch, S. Acetone-butanol fermentation of starches. Appl Microbiol. 1953; 1: 85-96.

Beesch, S. Acetone-butanol fermentation of sugars. Eng Proc Dev. 1952; 44: 1677-82.

Bermejo, et al. Expression of Clostridium acetobutylicum ATCC 824 genes in *Escherichia coli* for acetone production and acetate detoxification. Appl Environ Microbiol. Mar. 1998;64(3):1079-85.

Blevins, et al. Adaptation of a luciferase gene reporter and lac expression system to Borrelia burgdorferi. Appl Environ Microbiol. Mar. 2007;73(5):1501-13.

Boynton, et al. Cloning, sequencing, and expression of clustered genes encoding beta-hydroxybutyryl-coenzyme A (CoA) dehydrogenase, crotonase, and butyryl-CoA dehydrogenase from Clostridium acetobutylicum ATCC 824. J Bacteriol. 1996; 178(11): 3015-24.

Boynton, et al. Cloning, sequencing, and expression of genes encoding phosphotransacetylase and acetate kinase from Clostridium acetobutylicum ATCC 824. Appl Environ Microbiol. 1996; 62(8): 2758-66.

Bräu, et al. Cloning and expression of the structural gene for pyruvate decarboxylase of Zymomonas mobilis in *Escherichia coli*. Arch Microbiol. 1986; 144: 296-301.

Bringer-Meyer, et al. Pyruvate decarboxylase from Zymomonas mobilis. Isolation and partial characterization. Arch Microbiol. 1986; 146(2): 105-10.

Burchhardt, et al. Cloning and analysis of the β-galactosidase-encoding gene from Clostridium thermosulferogenes EMI. Gene. 1991; 106: 13-9.

Chakraborty, et al. Coordinate regulation of virulence genes in Listeria monocytogenes requires the product of the prfA gene. J Bacteriol. 1992; 174(2): 568-74.

Chalfie, et al. Green fluorescent protein as a marker for gene expression. Science. 1994; 263(5148): 802-5.

Chin, et al. Fedbatch operation using Clostridium acetobutylicum suspension culture as biocatalyst for enhancing hydrogen production. Biotechnol Prog. Mar.-Apr. 2003;19(2):383-8.

Contag, et al. Cloning of a lactate dehydrogenase gene from Clostridium acetobutylicum B643 and expression in *Escherichia coli*. Appl Environ Microbiol. 1990; 56(12):3760-5.

Conway, et al. Cloning and sequencing of the alcohol dehydrogenase II gene from Zymomonas mobilis. J Bacteriol. 1987; 169(6): 2591-7.

Cormack, et al. Yeast-enhanced green fluorescent protein (yEGFP)a reporter of gene expression in Candida albicans. Microbiology. 1997; 143(Pt 2): 303-11.

Craney, et al. A synthetic luxCDABE gene cluster optimized for expression in high-GC bacteria. Nucleic Acids Res. 2007;35(6):e46. Epub Mar. 1, 2007.

Davies, et al. Studies of the acetone-butyl alcohol fermentation. I. Nutritional and other factors involved in the preparation of active suspensions of Clostridium acetobutylicum. Biochem J. 1941; 35: 1320-31.

Davison, et al. Continuous direct solvent extraction of butanol in a fermenting fluidized-bed bioreactor with immobilized Clostridium acetobutylicum. In: Applied biochemistry and biotechnology.1993, vol. 39-40 (27 ref.), pp. 415-426.

Davison, et al. Novel immobilized-biocatalyst bioreactors for productioin of fuels and chemicals. In: ACS National Meeting & Exposition (Anaheim), 1999, vol. 42(2), pp. 215-218.

De Wet, et al. Cloning of firefly luciferase cDNA and the expression of active luciferase in *Escherichia coli*. Proc Natl Acad Sci USA. 1985; 82(23): 7870-3.

De Wet, et al. Firefly luciferase gene: structure and expression in mammalian cells. Mol Cell Biol. 1987; 7: 725-37.

Doyle, et al. Expression of firefly luciferase in Candida albicans and its use in the selection of stable transformants. Microb Pathog. Feb. 2006;40(2):69-81.

Durre, et al. Transcriptional regulation of solventogenesis in Clostridium acetobutylicum. J Mol Microbiol Biotechnol. 2002; 4: 295-300.

European search report (supplemental) dated Nov. 23, 2010 for Application No. 08829763.5.

European search report and search opinion dated Nov. 4, 2010 for Application No. 08829763.5.

European search report dated Oct. 8, 2010 for Application No. 07842375.3.

Ezeji, et al. Bioproduction of butanol from biomass: from genes to bioreactors. Curr Opin Biotechnol. Jun. 2007;18(3):220-7.

Ezeji, et al. Butanol fermentation research: upstream and downstream manipulations. Chem Rec. 2004;4(5):305-14.

Feustel, et al. Characterization and development of two reporter gene systems for Clostridium acetobutylicum. Appl Environ Microbiol. 2004; 70: 798-803.

Fey, et al. Green fluorescent protein production in the cellular slime molds Polysphondylium pallidum and Dictyostelium discoideum. Gene. 1995; 165(1): 127-30.

Fischer, et al. Cloning, sequencing, and molecular analysis of the sol operon of Clostridium acetobutylicum, a chromosomal locus involved in solventogenesis. J. Bacteriol. 1993; 175(21): 6959-69.

Fischer, et al. Selection and optimization of microbial hosts for biofuels production. Metab Eng. Nov. 2008;10(6):295-304.

Fontaine, et al. Molecular characterization and transcriptional analysis of adhE2, the gene encoding the NADH-dependent aldehyde/alcohol dehydrogenase responsible for butanol production in alcohologenic cultures of Clostridium acetobutylicum ATCC 824. J Bacteriol. 2002; 184(3): 821-30.

Frackman, et al. Cloning, organization, and expression of the bioluminescence genes of Xenorhabdus luminescens. J Bacteriol. 1990; 172(10): 5767-73.

Frick, et al. Continuous acetone-butanol production with free and immobilized Clostridium acetobutylicum. In: Applied microbiology and biotechnology. 1986, vol. 25, No. 3, pp. 186-193.

George, et al. Acetone, isopropanol, and butanol production by Clostridium beijernickii (syn. Clostridium butylicum) and Clostridium aurantibutyricum. Appl Environ Microbiol. 1983; 45: 1160-3.

Gerischer, et al. Cloning, sequencing, and molecular analysis of the acetoacetate decarboxylase gene region from Clostridium acetobutylicum. J Bacteriol. 1990; 172(12): 6907-18.

Gerischer, et al. mRNA analysis of the adc gene region of Clostridium acetobutylicum during the shift to solventogenesis. J Bacteriol. 1992; 174: 426-33.

Girbal, et al. Development of a sensitive gene expression reporter system and an inducible promoter-repressor system for Clostridium acetobutylicum. Appl Environ Microbiol. 2003; 69: 4985-8.

Girbal, et al. Regulation of metabolic shifts in Clostridium acetobutylicum ATCC824. FEMS Microbiol Rev. 1995; 17: 287-97.

Gottschalk. Bacterial Metabolism, 2nd Ed. New York, NY: Springer-Verlag; 1986.

Gottwald, et al. Formation of n-butanol from D-glucose by strains of Clostridium tetanomorphum group. Appl Environ Microbiol. 1984; 48: 573-6.

Gupta, et al. Expression of the Photorhabdus luminescens lux genes (luxA, B, C, D, and E) in *Saccharomyces cerevisiae*. FEMS Yeast Res. Dec. 2003;4(3):305-13.

Harris, et al. Characterization of recombinant strains of the Clostridium acetobutylicum butyrate kinase inactivation mutant: Need for new phenomenological models for solventogenesis and butanol inhibition? Biotechnol Bioeng. Jan. 5, 2000;67(1):1-11.

Hartmanis, et al. Uptake and activation of acetate and butyrate in Clostridium acetobutylicum. Appl Microbiol Biotechnol. 1984; 20: 66-71.

Hausding, et al. Inhibition of small G proteins of the rho family by statins or clostridium difficile toxin B enhances cytokine-mediated induction of NO synthase II. Br J Pharmacol. Oct. 2000;131(3):553-61.

Hermann, et al. Isolation and characterization of butanol-resistant mutants of Clostridium acetobutylicum. Appl Environ Microbiol. Nov. 1985;50(5):1238-43.

Hung, et al. Continuous perfusion microfluidic cell culture array for high-throughput cell-based assays. Biotechnol Bioeng. Jan. 5, 2005;89(1):1-8.

Hunter, et al. Formaldehyde metabolism by *Escherichia coli*. Carbon and solvent deuterium incorporation into glycerol, 1,2-propanediol, and 1,3-propanediol. Biochemistry. 1985; 24(15): 4148-55.

Hüsemann, et al. Solventogenesis in Clostridium acetobutylicum fermentations related to carboxylic acid and proton concentrations. Biotechnol Bioeng. 1988; 32: 843-52.

Ingram, et al. Expression of different levels of ethanologenic enzymes from Zymomonas mobilis in recombinant strains of *Escherichia coli*. Appl Environ Microbiol. 1988; 54(2): 397-404.

Ingram, et al. Genetic engineering of ethanol production in *Escherichia coli*. Appl Environ Microbiol, 1987; 53(10): 2420-5.

International search report dated Apr. 13, 2009 for PCT Application No. US2008/75515.

International search report dated Jan. 6, 2010 for PCT Application No. US2009/40050.

International search report dated Oct. 19, 2009 for PCT Application No. US2009/036868.

International search report dated Dec. 18, 2009 for PCT Application No. US2009/038300.

International search report dated Jun. 28, 2010 for PCT Application No. US2010/32463.

International search report dated Aug. 23, 2010 for PCT Application No. US10/39873.

International search report dated Aug. 3, 2010 for PCT Application No. US2010/032462.

International search report dated Sep. 16, 2008 for PCT Application No. US07/78321.

Jones, et al. Acetone-butanol fermentation revisited. Microbio. Rev. 1986; 50: 484-524.

Junelles, et al. Effect of pyruvate on glucose metabolism in Clostridium acetobutylicum. Biochimie. 1987; 69: 1183-90.

Keis, et al. Emended descriptions of Clostridium acetobutylicum and Clostridium beijerinckii, and descriptions of Clostridium saccharoperbutylacetonicum sp. nov. and Clostridium saccharobutylicum sp. nov. Int J Syst Evol Microbiol. Nov. 2001;51(Pt 6):2095-103.

Killeffer, D. Butanol and acetone from corn. A description of the fermentation process. Ind Eng Chem. 1927; 19: 46-50.

Klinke, et al. Inhibition of ethanol-producing yeast and bacteria by degradation products produced during pre-treatment of biomass. Applied Microbiology and Biotechnology. 2004;66(1):10-26.

Knoshaug, et al. Butanol Tolerance in a Selection of Microorganisms. Appl Biochem Biotechnol. Dec. 17, 2008. (8 pages).

Largier, et al. Immobilized Clostridium acetobutylicum P262 Mutants for Solvent Production. Appl Environ Microbiol. Aug. 1985;50(2):477-81.

Lee, et al. Fermentative butanol production by Clostridia. Biotechnol Bioeng. Oct. 1, 2008;101(2):209-28.

Lee. Biological conversion of lignocellulosic biomass to ethanol. Journal of Biotechnology. 1997;56(1):1-24.

Liu, et al. Genomic adaptation of ethanologenic yeast to biomass conversion inhibitors. Journal Applied Microbiology and Biotechnology. 2006;73(1): 27-36.

Lopez-Contreras, A. Utilisation of saccharides in extruded domestic organic waste by Clostridium acetobutylicum ATCC 824 for production of acetone, butanol, and ethanol. Appl Microbiol Biotechnol. 2000; 54: 162-7.

Martin, et al. Engineering a mevalonate pathway in *Escherichia coli* for production of terpenoids. Nature Biotech. 2003; 21: 796-802.

McCutchan, et al. The Butanol-Acetone Fermentations. Industrial Fermentations, Underkofler, et al., eds. New York, NY: Chemical Publishing. 1954. 347-388.

McNeil, et al. Effect of temperature upon growth rate and solvent production in batch cultures of Clostridium acetobutylicum. Biotech Lett. 1985; 7: 499-502.

Meighen, E. Bacterial bioluminescence: organization, regulation, and application of the lux genes. FASEB J. Aug. 1993;7(11):1016-22.

Mermelstein, et al. Expression of cloned homologous fermentative genes in Clostridium acetobutylicum ATCC 824. Biotechnology (NY). 1992; 10(2): 190-5.

Miller, et al. An improved GFP cloning cassette designed for prokaryotic transcriptional fusions. Gene. 1997; 191(2); 149-53.

Miyamoto, et al. Nucleotide sequence of the LuxC gene and the upstream DNA from the bioluminescent system of Vibrio harveyi. Nucleic Acids Res. 1988;16(4):1551-62.

Mosier, et al. Features of promising technologies for pretreatment of lignocellulosic biomass. Bioresource Technology. 2005;96(6):673-686.

Nair, et al. Molecular characterization of an aldehyde/alcohol dehydrogenase gene from Clostridium acetobutylicum ATCC 824. J Bacteriol. 1994; 176(3): 871-85.

Neale, et al. Nucleotide sequence of the pyruvate decarboxylase gene from Zymomonas mobilis. Nucl Acids Res. 1987; 15(4): 1753-61.

Ohta, et al. Genetic improvement of *Escherichia coli* for ethanol production: chromosomal integration of Zymomonas mobilis genes encoding pyruvate decarboxylase and alcohol dehydrogenase II. Appl Environ Microbiol. 1991; 57(4): 893-900.

Palmqvist, et al. Fermentation of lignocellulosic hydrolysates. II: inhibitors and mechanisms of inhibition. Bioresource Technology. 2000;74(1):25-33.

Paredes, et al. Transcriptional organization of the Clostridium acetobutylicum genome. Nuc Acids Res. 2004; 32(6): 1973-81.

Patterson, et al. Codon optimization of bacterial luciferase (lux) for expression in mammalian cells. J Ind Microbiol Biotechnol. Mar. 2005;32(3):115-23.

Petersen, et al. Molecular cloning of an alcohol (butanol) dehydrogenase gene cluster from Clostridium acetobutylicum ATCC 824. J Bacteriol. 1991; 173: 1831-4.

Phillips-Jones, et al. Use of a lux reporter system for monitoring rapid changes in alpha-toxin gene expression in Clostridium perfringens during growth. FEMS Microbiol Lett. Jul. 1, 2000;188(1):29-33.

Phillips-Jones, M. Bioluminescence (lux) expression in the anaerobe Clostridium perfringens. FEMS Microbiol Lett. Feb. 1, 1993;106(3):265-70.

Prendergast, et al. Chemical and physical properties of aequorin and the green fluorescent protein isolated from Aequorea forskalea. Biochemistry. 1978; 17(17): 3448-53.

Quixley; et al. Construction of a reporter gene vector for Clostridium beijerinckii using a Clostridium endoglucanase gene. J Mol Microbiol Biotechnol. 2000; 2: 53-7.

Quratulain, et al. Development and characterization of butanol—Resistant strain of Clostridium acetobutylicum in molasses medium. Folia Microbiologica. 1995;40(5):467-471.

Qureshi, et al. Biofilm reactors for industrial bioconversion processes: employing potential of enhanced reaction rates. Microb Cell Fact. Aug. 25, 2005;4:24-45. (21 pages).

Qureshi, et al. Butanol production from corn fiber xylan using Clostridium acetobutylicum. Biotechnol Prog. May-Jun. 2006;22(3):673-80.

Qureshi, et al. Continuous production of acetone-butanol-ethanol using immobilized cells of Clostridium acetobutylicum and integration with product removal by liquid-liquid extraction. Journal of Fermentation and Bioengineering. 1995;80(2):185-189.

Qureshi, et al. Continuous solvent production by Clostridium beijerinckii BA101 immobilized by adsorption onto brick. In: World journal of microbiology & biotechnology. 2000, vol. 16, No. 4, pp. 377-382.

Reardon, et al. In Situ Fluorescence Monitoring of Immobilized Clostridum Acetobutylicum. Biotechnol Lett. 1986; 8(11): 817-822.

Rogers, et al. Clostridium acetobutylicum mutants that produce butyraldehyde and altered quantities of solvents. Appl Enviorn Microbiol. 1987; 53: 2761-6.

Rogers, P. Genetics and biochemistry of Clostridium relevant to development of fermentation process. Adv Appl Microbiol. 1986; 31: 1-60.

Sauer, et al. Differential induction of genes related to solvent formation during the shift from acidogenesis to solventogenesis in continuous culture of Clostridium acetobutylicum. FEMS Microbiol Lett. 1995; 125: 115-20.

Scotcher, et al. Sequences affecting the regulation of solvent production in Clostridium Acetobutylicum. J. Ind. Microbiol. Biotechnol. 2003; 30:414-420.

Stim-Herndon, et al. Characterization of an acetyl-CoA C-acetyltransferase (thiolase) gene from Clostridium acetobutylicum ATCC 824. Gene. 1995; 154(1): 81-5.

Straight, et al. GFP tagging of budding yeast chromosomes reveals that protein-protein interactions can mediate sister chromatid cohesion. Curr Biol. 1996; 6(12): 1599-608.

Syed, et al. Enhanced butanol production by mutant strains of clostridium acetobutylicum in molasses medium. Turkish Journal of Biochemistry. 2008; 33(1):25-30.

Tashiro, et al. High butanol production by Clostridium saccharoperbutylacetonicum N1-4 in fed-batch culture with pH-Stat continuous butyric acid and glucose feeding method. J Biosci Bioeng. 2004;98(4):263-8.

Tatsumi, et al. Molecular cloning and expression in *Escherichia coli* of a cDNA clone encoding luciferase of a firefly, Luciola lateralis. Biochim Biophys Acta. 1992; 1131(2): 161-5.

Thormann, et al. Control of butanol formation in Clostridium acetobutylicum by transcriptional activation. J Bacteriol. Apr. 2002;184(7):1966-73.

Tolan, et al. Fermentation of d-xylose and l-arabinose to ethanol by Erwinia chrysanthemi. Appl Environ Microbiol. 1987; 53(9): 2033-2038.

Tomas, et al. Transcriptional analysis of butanol stress and tolerance in Clostridium acetobutylicum. J Bacteriol. Apr. 2004;186(7):2006-18.

Tummula, et al. Development and characterization of a gene expression reporter system for Clostridium acetobutylicum ATCC 824. Appl Environ Microbiol. 1999; 65: 3793-9.

UK combined office action dated Jan. 18, 2008 and search report for Application No. GB0718077.1.

UK combined office action dated Jul. 27, 2010 and search report dated Jan. 17, 2008 for Application No. GB0718077.1.

UK office action dated Aug. 19, 2010 for Application No. GB0906322.3.

Walter, et al. Molecular characterization of two Clostridium acetobutylicum ATCC 824 butanol dehydrogenase isozyme genes. J Bacteriol. 1992; 174(22): 7149-58.

Ward, et al. An energy transfer protein in coelenterate bioluminescence. Characterization of the Renilla green-fluorescent protein. J Biol Chem. 1979; 254(3): 781-8.

Ward, et al. Energy-transfer via protein-protein interaction in renilla bioluminescence. Photochemistry and Photobiology. 1978; 27: 389-96.

Ward, et al. Reversible denaturation of Aequorea green-fluorescent protein: physical separation and characterization of the renatured protein. Biochemistry. 1982; 21(19): 4535-40.

Winzer, et al. Differential regulation of two thiolase genes fromClostridium acetobutylicum DSM 792. J Mol Microbiol Biotechnol. 2000; 2(4): 531-41.

Wood, et al. Complementary DNA coding click beetle luciferases can elicit bioluminescence of different colors. Science. 1989; 244: 700-2.

Xi, et al. Cloning and nucleotide sequences of lux genes and characterization of luciferase of Xenorhabdus luminescens from a human wound. J Bacteriol. 1991; 173: 1399-405.

Yamada, et al. Production of glycerol from methanol by a mutant strain of Candida boidinii No. 2201. Agric Biol Chem. 1989; 53(2): 541-3.

Yu, et al. Differential induction of β-galactosidase and phosopho-β-galactosidase activities in the fermentation of whey permeate by Clostridium acetobutylicum. Appl Microbiol Biotechnol. 1987; 26: 254-7.

Zaldivar, et al. Fuel ethanol production from lignocellulose: a challenge for metabolic engineering and process integration. Journal Applied Microbiology and Biotechnology. 2001;56(1-2):17-34.

Biebl. Fermentation of glycerol by Clostridium pasteurianum—batch and continuous culture studies. J Ind Microbiol Biotechnol. Jul. 2001;27(1):18-26.

Chiao, et al. History of the acetone-butanol-ethanol fermentation industry in China: development of continuous production technology. J Mol Microbiol Biotechnol. 2007;13(1-3):12-4.

Forsberg. Production of 1,3-Propanediol from Glycerol by Clostridium acetobutylicum and Other Clostridium Species. Appl Environ Microbiol. Apr. 1987;53(4):639-43.

Gonzalez-Pajuelo, et al. Microbial conversion of glycerol to 1,3-propanediol: physiological comparison of a natural producer, Clostridium butyricum VPI 3266, and an engineered strain, Clostridium acetobutylicum DG1(pSPD5). Appl Environ Microbiol. Jan. 2006;72(1):96-101.

Ni, et al. Recent progress on industrial fermentative production of acetone-butanol-ethanol by Clostridium acetobutylicum in China. Appl Microbiol Biotechnol. Jun. 2009;83(3):415-23. Epub May 9, 2009.

Office action dated Jul. 13, 2011 for EP Application No. 07842375.3.

Sun, et al. The Acetone-Butanol (ABE) Fermentation Industries in China. Accessed Sep. 2, 2011. services.bepress.com/cgi/viewcontent.cgi?article=1006&context=eci/bioenergy_i.

Zverlov, et al. Bacterial acetone and butanol production by industrial fermentation in the Soviet Union: use of hydrolyzed agricultural waste for biorefinery. Appl Microbiol Biotechnol. Aug. 2006;71(5):587-97. Epub May 10, 2006.

Office action dated Jul. 19, 2011 for U.S. Appl. No. 11/853,681.

U.S. Appl. No. 13/061,898, filed Mar. 2, 2011, Burns-Guydish et al.

Office action dated Sep. 28, 2010 for U.S. Appl. No. 11/853,681.

UK office action dated Mar. 31, 2011 for Application No. GB0906322.3.

Chang, et al. Kinetics of butanol fermentation by Clostridium acetobutylicum in multiple-step fibrous bed bioreactor—BIOT 388. Aug. 20, 2008, 236th ACS National Meeting. Phildelphia, PA.

European search report and opinion dated Mar. 16, 2012 for EP Application No. 09811872.2.

European seasrch report and search opinion dated Apr. 3, 2012 for EP 09730267.3.

Gholizadeh, L. Thesis. Enhanced Butanol Production by Free and Immobilized Clostridium sp. Cells Using Butyric Acid as Co-Substrate. School of Engineering. University of Boras, School of Engineering. Aug. 12, 2009.

Huang, et al. Acetic acid production from fructose by clostridium formicoaceticum immobilized in a fibrous-Bed bioreactor . Biotechnol Prog. Sep. 1998;14(5):800-6.

Liu, et al. Construction and characterization of ack deleted mutant of Clostridium tyrobutyricum for enhanced butyric acid and hydrogen production. Biotechnol Prog. Sep.-Oct. 2006;22(5):1265-75.

Office action dated Sep. 6, 2012 for U.S. Appl. No. 12/823,092.

Ramey, et al. Production of Butyric Acid and Butanol from Biomass. Work performed under Contract No. DE-F-G02-00ER86106 for U.S. Department of Energy, Morgantown, WV. 2004.

Suwannakham, et al. Enhanced propionic acid fermentation by Propionibacterium acidipropionici mutant obtained by adaptation in a fibrous-bed bioreactor. Biotechnol Bioeng. Aug. 5, 2005;91(3):325-37.

Wu, et al. Extractive fermentation for butyric acid production from glucose by Clostridium tyrobutyricum. Biotechnol Bioeng. Apr. 5, 2003;82(1):93-102.

Zhu, et al. Adaptation of Clostridium tyrobutyricum for enhanced tolerance to butyric acid in a fibrous-bed bioreactor. Biotechnol Prog. Mar.-Apr. 2003;19(2):365-72.

Zhu, et al. Construction and characterization of pta gene-deleted mutant of Clostridium tyrobutyricum for enhanced butyric acid fermentation. Biotechnol Bioeng. Apr. 20, 2005;90(2):154-66.

Zhu, Y. Dissertation. Enhanced Butyric Acid Fermentation by Clostridium Tyrobutyricum Immobilized in a Fibrous-Bed Bioreactor. Graduate School of The Ohio State University. 2003.

U.S. Appl. No. 13/353,233, filed Jan. 18, 2012, Contag.

U.S. Appl. No. 13/441,786, filed Apr. 6, 2012, Burns-Guydish et al.

Office action dated Oct. 7, 2011 for U.S. Appl. No. 12/205,845.

UK office action dated Sep. 30, 2011 for Application No. GB0906322.3.

European office action dated Oct. 24, 2012 for EP 07842375.3.

European office action dated Nov. 29, 2012 for EP 09730267.3.

Office action dated Nov. 28, 2012 for CN Application No. 200980121678.2.

Yang, et al. Continuous propionate production from whey permeate using a novel fibrous bed bioreactor. Biotechnol Bioeng. May 1994;43(11):1124-30.

\* cited by examiner

Figure 2A

| Butanol % (v/v) | OD600 0 h Co-5673* | OD600 0 h Co-0124* | OD600 0 h Co-7449* | OD600 24 h Co-5673 | OD600 24 h Co-0124 | OD600 24 h Co-7449 | OD600 96 h Co-5673 | OD600 96 h Co-0124 | OD600 96 h Co-7449 |
|---|---|---|---|---|---|---|---|---|---|
| 0 | 0.037 | 0.046 | 0.043 | 1.34 | 1.455 | 1.145 | 2.048 | 1.959 | 2.022 |
| 0.5 | 0.037 | 0.046 | 0.043 | 1.279 | 1.231 | 0.491 | 1.906 | 1.764 | 1.739 |
| 1 | 0.037 | 0.046 | 0.043 | 1.223 | 0.915 | 0.291 | 1.359 | 1.172 | 0.981 |
| 1.1 | 0.037 | 0.046 | 0.043 | 1.09 | 0.784 | 0.306 | 1.281 | 0.998 | 0.682 |
| 1.2 | 0.037 | 0.046 | 0.043 | 0.93 | 0.717 | 0.231 | 0.923 | 0.935 | 0.43 |
| 1.3 | 0.037 | 0.046 | 0.043 | 0.706 | 0.531 | 0.189 | 0.721 | 0.847 | 0.335 |
| 1.4 | 0.037 | 0.046 | 0.043 | 0.345 | 0.27 | 0.011 | 0.298 | 0.271 | 0.268 |
| 1.5 | 0.037 | 0.046 | 0.043 | 0.019 | 0.069 | 0.007 | 0.023 | 0.176 | 0.011 |
| 1.6 | 0.037 | 0.046 | 0.043 | 0.035 | 0.114 | 0.01 | 0.033 | 0.098 | 0.011 |

Figure 2B

| OD600 0 h Co-5673* | OD600 0 h Co-0124* | OD600 0 h Co-7449* |
|---|---|---|
| 0.741 | 0.917 | 0.869 |

| Butanol % (v/v) | Co-5673 | Co-0124 | Co-7449 |
|---|---|---|---|
| 0 | * | * | * |
| 2.2 | * | * | |
| 2.3 | | | |
| 2.4 | | | |
| 2.5 | | | |
| 2.6 | | | |

FIGURE 6A

| Strain | Butanol % (v/v) (Liquid) | Butanol % (v/v) (Solid) |
|---|---|---|
| Co-5673 | 1.4 | 2.2 |
| Co-0124 | 1.6 | 2.2 |
| Co-7449 | 1.3 | 2.1 |

FIGURE 6B

| Butanol % (v/v) | Co-5673 | Co-0124 | Co-7449 |
|---|---|---|---|
| 0 | * | * | * |
| 2.2 | * | * | * |
| 2.3 |  | * |  |
| 2.4 |  |  |  |
| 2.5 |  |  |  |
| 2.6 |  |  |  |

FIGURE 7A

| Strain | Butanol % (v/v) (Liquid) | Butanol % (v/v) (Solid) |
|---|---|---|
| Co-5673 | 1.4 | 2.2 |
| Co-0124 | 1.6 | 2.3 |
| Co-7449 | 1.4 | 2.2 |

FIGURE 7B

Bonechar Particles

| Type | Settling Velocity (cm/s) | | | Equiv. Diameter (μm) | | |
|---|---|---|---|---|---|---|
| | "-1σ" | Mean | "+1σ" | "-1σ" | Mean | "+1σ" |
| 5x8 | 8.85 | 11.42 | 13.99 | 550 | 763 | 988 |
| 10x28 | 4.84 | 6.4 | 7.96 | 239 | 341 | 451 |
| 20x60 | 3.45 | 4.42 | 5.39 | 156 | 215 | 277 |

| Case: Bonechare (type 5x8) in 4% glucose solution | | | | | | | |
|---|---|---|---|---|---|---|---|
| $\rho_p$(kg/m$^3$)= 2270 | | $\rho_f$(kg/m$^3$)= 1014 | | | $\mu$(N.s/m$^2$)= 0.0009 | | |
| $\varepsilon_{mf}$ | $D_p$ (μm) | A | B | C | Ar | $Re_{mf}$ | $U_{mf}$(cm/s) |
| 0.25 | 550 | 1.75 | 112.5 | -50.314 | 3,220 | 0.444 | 0.072 |
| 0.25 | 763 | 1.75 | 112.5 | -134.330 | 8,597 | 1.173 | 0.136 |
| 0.25 | 988 | 1.75 | 112.5 | -291.655 | 18,666 | 2.496 | 0.224 |
| 0.30 | 550 | 1.75 | 105 | -86.942 | 3,220 | 0.817 | 0.132 |
| 0.30 | 763 | 1.75 | 105 | -232.122 | 8,597 | 2.135 | 0.248 |
| 0.30 | 988 | 1.75 | 105 | -503.979 | 18,666 | 4.467 | 0.401 |
| 0.35 | 550 | 1.75 | 97.5 | -138.061 | 3,220 | 1.382 | 0.223 |
| 0.35 | 763 | 1.75 | 97.5 | -368.600 | 8,597 | 3.554 | 0.413 |
| 0.35 | 988 | 1.75 | 97.5 | -800.301 | 18,666 | 7.262 | 0.652 |
| 0.40 | 550 | 1.75 | 90 | -206.085 | 3,220 | 2.196 | 0.354 |
| 0.40 | 763 | 1.75 | 90 | -550.214 | 8,597 | 5.521 | 0.642 |
| 0.40 | 988 | 1.75 | 90 | -1,194.618 | 18,666 | 10.944 | 0.983 |
| 0.45 | 550 | 1.75 | 82.5 | -293.429 | 3,220 | 3.323 | 0.536 |
| 0.45 | 763 | 1.75 | 82.5 | -783.410 | 8,597 | 8.103 | 0.943 |
| 0.45 | 988 | 1.75 | 82.5 | -1,700.930 | 18,666 | 15.513 | 1.394 |
| 0.50 | 550 | 1.75 | 75 | -402.510 | 3,220 | 4.824 | 0.778 |
| 0.50 | 763 | 1.75 | 75 | -1,074.637 | 8,597 | 11.332 | 1.318 |
| 0.50 | 988 | 1.75 | 75 | -2,333.238 | 18,666 | 20.909 | 1.878 |

| Case: Bonechare (type 10x28) in 4% glucose solution | | | | | | |
|---|---|---|---|---|---|---|
| $\rho_p(kg/m^3)=$ 2360 | | $\rho_f(kg/m^3)=$ 1014 | | $\mu(N.s/m^2)=$ 0.0009 | | |
| $\varepsilon_{mf}$ | $D_p$ (μm) | A | B | C | Ar | $Re_{mf}$ | $U_{mf}$(cm/s) |
| 0.25 | 239 | 1.75 | 112.5 | -4.128 | 264 | 0.037 | 0.014 |
| 0.25 | 341 | 1.75 | 112.5 | -11.991 | 767 | 0.106 | 0.028 |
| 0.25 | 451 | 1.75 | 112.5 | -27.741 | 1,775 | 0.246 | 0.048 |
| 0.30 | 239 | 1.75 | 105.0 | -7.134 | 264 | 0.068 | 0.025 |
| 0.30 | 341 | 1.75 | 105.0 | -20.721 | 767 | 0.197 | 0.051 |
| 0.30 | 451 | 1.75 | 105.0 | -47.937 | 1,775 | 0.453 | 0.089 |
| 0.35 | 239 | 1.75 | 97.5 | -11.329 | 264 | 0.116 | 0.043 |
| 0.35 | 341 | 1.75 | 97.5 | -32.904 | 767 | 0.335 | 0.087 |
| 0.35 | 451 | 1.75 | 97.5 | -76.122 | 1,775 | 0.770 | 0.152 |
| 0.40 | 239 | 1.75 | 90.0 | -16.910 | 264 | 0.187 | 0.070 |
| 0.40 | 341 | 1.75 | 90.0 | -49.116 | 767 | 0.540 | 0.141 |
| 0.40 | 451 | 1.75 | 90.0 | -113.629 | 1,775 | 1.233 | 0.243 |
| 0.45 | 239 | 1.75 | 82.5 | -24.077 | 264 | 0.290 | 0.108 |
| 0.45 | 341 | 1.75 | 82.5 | -69.932 | 767 | 0.833 | 0.217 |
| 0.45 | 451 | 1.75 | 82.5 | -161.788 | 1,775 | 1.886 | 0.371 |
| 0.50 | 239 | 1.75 | 75.0 | -33.028 | 264 | 0.436 | 0.162 |
| 0.50 | 341 | 1.75 | 75.0 | -95.929 | 767 | 1.243 | 0.324 |
| 0.50 | 451 | 1.75 | 75.0 | -221.931 | 1,775 | 2.779 | 0.547 |

| Case: Bonechare (type 20x60) in 4% glucose solution | | | | | | | |
|---|---|---|---|---|---|---|---|
| $\rho_p(kg/m^3)=$ | 2380 | $\rho_f(kg/m^3)=$ | 1014 | $\mu(N.s/m^2)=$ | 0.0009 | | |
| $\varepsilon_{mf}$ | $D_p\ (\mu m)$ | A | B | C | Ar | $Re_{mf}$ | $U_{mf}(cm/s)$ |
| 0.25 | 156 | 1.75 | 112.5 | -1.148 | 73 | 0.010 | 0.006 |
| 0.25 | 215 | 1.75 | 112.5 | -3.005 | 192 | 0.027 | 0.011 |
| 0.25 | 277 | 1.75 | 112.5 | -6.427 | 411 | 0.057 | 0.018 |
| 0.3 | 156 | 1.75 | 105 | -1.984 | 73 | 0.019 | 0.011 |
| 0.3 | 215 | 1.75 | 105 | -5.193 | 192 | 0.049 | 0.020 |
| 0.3 | 277 | 1.75 | 105 | -11.107 | 411 | 0.106 | 0.034 |
| 0.35 | 156 | 1.75 | 97.5 | -3.150 | 73 | 0.032 | 0.018 |
| 0.35 | 215 | 1.75 | 97.5 | -8.247 | 192 | 0.084 | 0.035 |
| 0.35 | 277 | 1.75 | 97.5 | -17.637 | 411 | 0.180 | 0.058 |
| 0.40 | 156 | 1.75 | 90 | -4.703 | 73 | 0.052 | 0.030 |
| 0.40 | 215 | 1.75 | 90 | -12.310 | 192 | 0.136 | 0.056 |
| 0.40 | 277 | 1.75 | 90 | -26.327 | 411 | 0.291 | 0.093 |
| 0.45 | 156 | 1.75 | 82.5 | -6.696 | 73 | 0.081 | 0.046 |
| 0.45 | 215 | 1.75 | 82.5 | -17.528 | 192 | 0.212 | 0.087 |
| 0.45 | 277 | 1.75 | 82.5 | -37.485 | 411 | 0.450 | 0.144 |
| 0.5 | 156 | 1.75 | 75 | -9.185 | 73 | 0.122 | 0.069 |
| 0.5 | 215 | 1.75 | 75 | -24.044 | 192 | 0.318 | 0.131 |
| 0.5 | 277 | 1.75 | 75 | -51.419 | 411 | 0.675 | 0.216 |

| Bonechar (type 5x8) in 4% glucose solution | | | | | | |
|---|---|---|---|---|---|---|
| $\rho_p$(kg/m³)= 2270 | | $\rho_f$(kg/m³)= 1014 | | $\mu$(N.s/m²)= 0.0009 | | |
| | $D_p$ (μm)= 550 | | $D_p$ (μm)= 763 | | $D_p$ (μm)= 988 | |
| | D (cm)= 10 | | D (cm)= 10 | | D (cm)= 10 | |
| | $U_t$ (cm/s)= 8.84 | | $U_t$ (cm/s)= 11.43 | | $U_t$ (cm/s)= 13.99 | |
| | $\varepsilon_{mf}$= 0.50 | | $\varepsilon_{mf}$= 0.50 | | $\varepsilon_{mf}$= 0.50 | |
| | $U_{mf}$ (cm/s)= 0.78 | | $U_{mf}$ (cm/s)= 1.32 | | $U_{mf}$ (cm/s)= 1.88 | |
| | Ar= 3,220 | | Ar= 8,597 | | Ar= 18,666 | |
| | y= 1.765 | | y= 2.680 | | y= 3.626 | |
| | n= 3.268 | | n= 3.052 | | n= 2.919 | |
| U (cm/s) | $\varepsilon$ | H/H$_{packed}$ | $\varepsilon$ | H/H$_{packed}$ | $\varepsilon$ | H/H$_{packed}$ |
| 0.78 | 0.476 | 1.004 | | | 0.372 | 0.796 |
| 1.32 | 0.559 | 1.183 | 0.493 | 0.996 | | |
| 1.88 | 0.623 | 1.375 | 0.554 | 1.120 | 0.503 | 1.006 |
| 2.30 | 0.662 | 1.530 | 0.591 | 1.224 | 0.539 | 1.084 |
| 2.60 | 0.688 | 1.650 | 0.616 | 1.301 | 0.562 | 1.141 |
| 3.00 | 0.718 | 1.825 | 0.645 | 1.409 | 0.590 | 1.220 |

FIGURE 13A

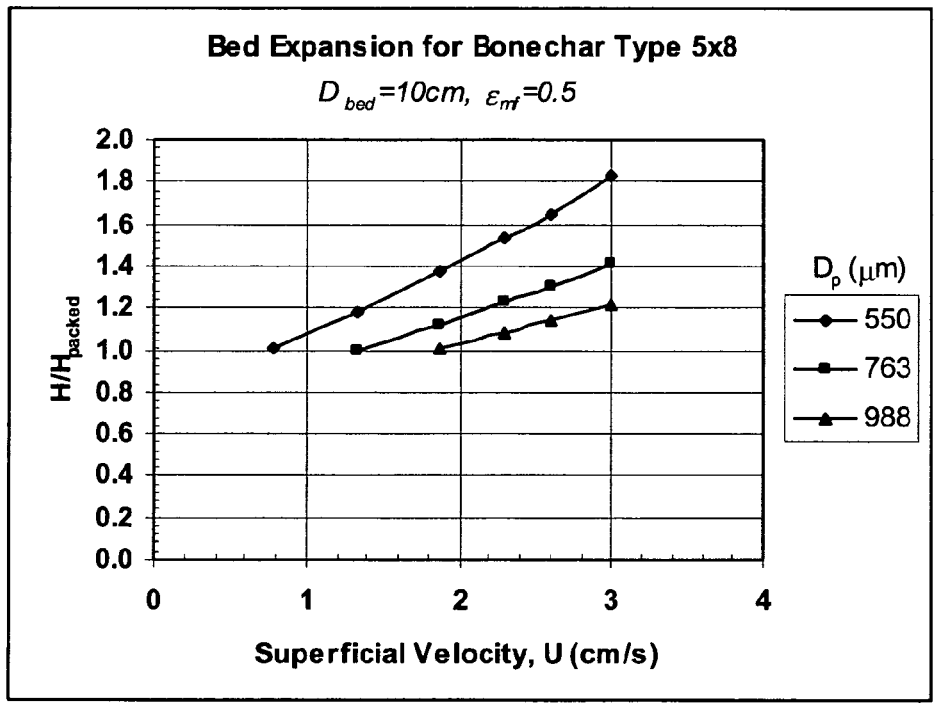

FIGURE 13B

| Bonechar (type 10x28) in 4% glucose solution | | | | | | |
|---|---|---|---|---|---|---|
| $\rho_p$(kg/m³)= 2380 | | $\rho_f$(kg/m³)= 1014 | | $\mu$(N.s/m²)= 0.0009 | | |
| | $D_p$ (μm)= 239 | | $D_p$ (μm)= 341 | | $D_p$ (μm)= 451 | |
| | D (cm)= 10 | | D (cm)= 10 | | D (cm)= 10 | |
| | $U_t$ (cm/s)= 4.84 | | $U_t$ (cm/s)= 6.40 | | $U_t$ (cm/s)= 7.96 | |
| | $\varepsilon_{mf}$= 0.50 | | $\varepsilon_{mf}$= 0.50 | | $\varepsilon_{mf}$= 0.50 | |
| | $U_{mf}$ (cm/s)= 0.16 | | $U_{mf}$ (cm/s)= 0.32 | | $U_{mf}$ (cm/s)= 0.55 | |
| | Ar= 264 | | Ar= 767 | | Ar= 1,775 | |
| | y= 0.547 | | y= 0.915 | | y= 1.351 | |
| | n= 3.951 | | n= 3.653 | | n= 3.421 | |
| U (cm/s) | $\varepsilon$ | H/H$_{packed}$ | $\varepsilon$ | H/H$_{packed}$ | $\varepsilon$ | H/H$_{packed}$ |
| 0.16 | 0.422 | 1.005 | | | | |
| 0.32 | 0.503 | 1.146 | 0.441 | 1.004 | | |
| 0.55 | 0.577 | 1.321 | 0.511 | 1.132 | 0.458 | 1.002 |
| 0.80 | 0.634 | 1.506 | 0.566 | 1.262 | 0.511 | 1.102 |
| 1.10 | 0.687 | 1.738 | 0.618 | 1.418 | 0.561 | 1.218 |
| 1.30 | 0.717 | 1.906 | 0.647 | 1.525 | 0.589 | 1.296 |

FIGURE 14A

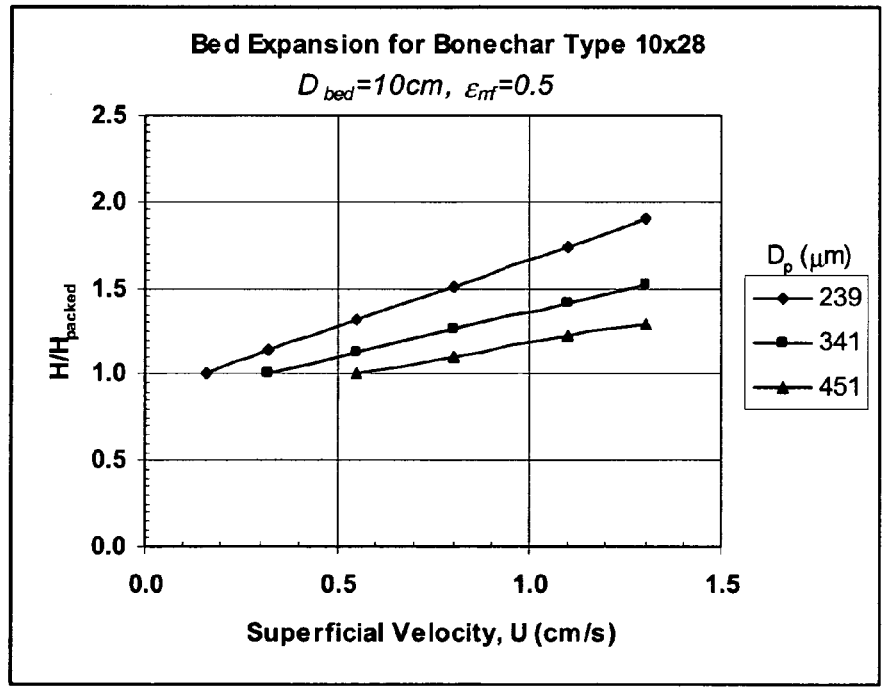

FIGURE 14B

| Bonechar (type 20x60) in 4% glucose solution | | | | | | |
|---|---|---|---|---|---|---|
| $\rho_p(kg/m^3)$= 2360 | | $\rho_f(kg/m^3)$= 1014 | | $\mu(N.s/m^2)$= 0.0009 | | |
| $D_p$ (μm)= | 156 | $D_p$ (μm)= | 215 | $D_p$ (μm)= | 277 | |
| D (cm)= | 10 | D (cm)= | 10 | D (cm)= | 10 | |
| $U_t$ (cm/s)= | 3.44 | $U_t$ (cm/s)= | 4.42 | $U_t$ (cm/s)= | 5.39 | |
| $\varepsilon_{mf}$= | 0.50 | $\varepsilon_{mf}$= | 0.50 | $\varepsilon_{mf}$= | 0.50 | |
| $U_{mf}$ (cm/s)= | 0.07 | $U_{mf}$ (cm/s)= | 0.13 | $U_{mf}$ (cm/s)= | 0.22 | |
| Ar= | 73 | Ar= | 192 | Ar= | 411 | |
| y= | 0.289 | y= | 0.468 | y= | 0.679 | |
| n= | 4.262 | n= | 4.035 | n= | 3.830 | |
| U (cm/s) | ε | H/H$_{packed}$ | ε | H/H$_{packed}$ | ε | H/H$_{packed}$ |
| 0.07 | 0.401 | 0.985 | | | | |
| 0.13 | 0.464 | 1.082 | 0.417 | 1.008 | | |
| 0.22 | 0.525 | 1.202 | 0.475 | 1.103 | 0.434 | 1.003 |
| 0.50 | 0.636 | 1.524 | 0.583 | 1.348 | 0.538 | 1.201 |
| 1.00 | 0.748 | 2.137 | 0.692 | 1.773 | 0.644 | 1.525 |
| 1.20 | 0.781 | 2.434 | 0.724 | 1.961 | 0.676 | 1.661 |

Specifications

$V_R$ (ltrs): 1.0 (packed bed volume)
Particles: Bonechar 5x8
$\sim\varepsilon_{mf}$: 0.5

| $D_b$ (cm) | $A_b$ (cm²) | $H_p$ (cm) | To fluidize large particles | | Bed expansion for small particles | | |
|---|---|---|---|---|---|---|---|
| | | | $U_b$ (cm/s) | $\mathcal{V}_f$ (ltrs/min) | $H/H_p$ | H (cm) | $H_e$ (cm) |
| 6 | 28.28 | 35.36 | 1.88 | 3.19 | 1.42 | 50.14 | 14.78 |
| 8 | 50.27 | 19.89 | 1.88 | 5.67 | 1.39 | 27.68 | 7.79 |
| 10 | 78.55 | 12.73 | 1.88 | 8.85 | 1.37 | 17.50 | 4.77 |
| 12 | 113.11 | 8.84 | 1.88 | 12.75 | 1.36 | 12.05 | 3.21 |
| 14 | 153.96 | 6.50 | 1.88 | 17.35 | 1.35 | 8.80 | 2.30 |

Specifications

$V_R$ (ltrs): 1.0 (packed bed volume)
Particles: Bonechar 10x28
$\sim\varepsilon_{mf}$: 0.5

| $D_b$ (cm) | $A_b$ (cm$^2$) | $H_p$ (cm) | To fluidize large particles | | Bed expansion for small particles | | |
|---|---|---|---|---|---|---|---|
| | | | $U_b$ (cm/s) | $\mathcal{V}_f$ (ltrs/min) | $H/H_p$ | H (cm) | $H_e$ (cm) |
| 6 | 28.28 | 35.36 | 0.55 | 0.93 | 1.34 | 47.31 | 11.95 |
| 8 | 50.27 | 19.89 | 0.55 | 1.65 | 1.33 | 26.42 | 6.52 |
| 10 | 78.55 | 12.73 | 0.55 | 2.58 | 1.32 | 16.82 | 4.09 |
| 12 | 113.11 | 8.84 | 0.55 | 3.71 | 1.32 | 11.63 | 2.79 |
| 14 | 153.96 | 6.50 | 0.55 | 5.05 | 1.31 | 8.52 | 2.03 |

Specifications

$V_R$ (ltrs): 1.0 (packed bed volume)
Particles: Bonechar 20x60
$\sim\varepsilon_{mf}$: 0.5

| $D_b$ (cm) | $A_b$ (cm$^2$) | $H_p$ (cm) | To fluidize large particles | | Bed expansion for small particles | | |
|---|---|---|---|---|---|---|---|
| | | | $U_b$ (cm/s) | $\mathscr{V}_f$ (ltrs/min) | $H/H_p$ | $H$ (cm) | $H_e$ (cm) |
| 6 | 28.28 | 35.36 | 0.22 | 0.37 | 1.21 | 42.78 | 7.42 |
| 8 | 50.27 | 19.89 | 0.22 | 0.66 | 1.21 | 23.97 | 4.08 |
| 10 | 78.55 | 12.73 | 0.22 | 1.04 | 1.20 | 15.30 | 2.57 |
| 12 | 113.11 | 8.84 | 0.22 | 1.49 | 1.20 | 10.60 | 1.76 |
| 14 | 153.96 | 6.50 | 0.22 | 2.03 | 1.20 | 7.78 | 1.28 |

| Bonechar Grade | Dry Weight (g) | Wet Weight (g) | Original Bed Vol (cm³) | Original Bed Height (cm) | Flow at Fluidization (L/min) | Fluidized Bed Vol (cm³) | Fluidized Bed Height (cm) | Superficial Velocity (cm/s) | Bulk Density (g/mL) | Measured Void Volume | Effective Void Volume |
|---|---|---|---|---|---|---|---|---|---|---|---|
| 5x8 | 10 | 12.7 | 19.5 | 9.8 | 0.68 | 22-25 | 11-12.5 | 5.63 | 0.72 | 0.63 | 0.43 |
| 10x28 | 10 | 13.3 | 22.0 | 11.0 | 0.51 | 40 | 20 | 4.25 | 0.69 | 0.63 | 0.40 |
| 20x60 | 10 | 14.0 | 19.0 | 9.5 | 0.30 | 34 | 17 | 2.50 | 0.74 | 0.65 | 0.35 |

FIGURE 20A

| Bonechar Grade | Dry Weight (g) | Glass beads (cm³) | Bonechar Volume (cm³) | Bonechar Height (cm) | Flow at Fluidization (L/min) | Fluidized Bed Vol (cm³) | Fluidized Bed Height (cm) | Superficial Velocity (cm/s) |
|---|---|---|---|---|---|---|---|---|
| 5x8 | 10.0 | 3.0 | 17.5 | 8.8 | 0.226 | 18 | 9.0 | 1.88 |
| 10x28 | 10.0 | 3.0 | 15.5 | 7.8 | 0.103 | 16.5 | 8.3 | 0.86 |
| 20x60 | 10.1 | 3.0 | 17.0 | 8.5 | 0.040 | 17.5 | 8.8 | 0.33 |

FIGURE 20B

| Run No. | Strain | Support | Substrate | Dilution Rate [$h^{-1}$] | Butanol Titer [g/L] | Butanol Yield (Y) [g BuOH/ g substrate] | Butanol Productivity (P) [g/L/h] |
|---|---|---|---|---|---|---|---|
| 2008065 | Co-7449 | Bonechar | Glucose | 0.73 | 4.0 – 4.5 | 0.19 – 0.21 | 2.9 – 3.3 |
| 2008137 | Co-7449 | Bonechar | Sucrose | 0.51 | 5.0 – 8.0 | 0.24 – 0.26 | 2.6 – 4.1 |
| 2009012 | Co-5673 | Bonechar | Sucrose | 0.73 | 8.4* | 0.26* | 6.1* |
| 2009021 | Co-7449 | Bonechar | Xylose | 0.76 | 5.4* | 0.26* | 4.1* |
| 2009023 | Co-5673 | Bonechar | Xylose | 0.73 | 4.0* | 0.26* | 2.95* |

FIGURE 27

IMMOBILIZED PRODUCT TOLERANT MICROORGANISMS

CROSS REFERENCE

This application claims the benefit of U.S. Provisional Application No. 61/043,710, filed, Apr. 9, 2008 that is herein incorporated by reference in its entirety.

BACKGROUND OF THE INVENTION

Industrial scale fermentations were historically performed for solvent and acid production prior to the rise of the petrochemical industry. Concerns about pollution, climate change, and resulting environmental degradation have renewed interest, particular where low cost or waste biomatter are available as feedstock. One problem that economically constrains more widespread adoption is the high energy expenditure required to recover fermentation products from the low concentrations typically seen in fermentation broths. Efforts to increase product concentrations in fermentation broths have met with limited success owing to the toxicity of these compounds to the cultured microorganisms. Another issue which constrains the economic feasibility of fermentation based bioproducts is the productivity of the fermentation process. Increases in productivity lead to an improved use of installed capital.

The present invention details the surprising discovery that strains, environmental isolates, or mutants of product producing microorganisms can be adapted or selected for their simultaneous ability to grow on solid support and tolerate high concentrations of a product and that these strains, environmental isolates, or mutants of product producing microorganisms retain the higher product tolerance in culture if they are immobilized on a solid support rather than cultured as a suspension culture. Higher product concentrations are now possible that improve overall culture productivity and reduce energy usage. Increased product tolerance may rely on decreased inhibitory effect by known inhibitory agents such as HMF, fufural, levulenic acid, glucoronic acid or acetic acid, which may be generated by the organism or be present in the initial feed.

SUMMARY OF THE INVENTION

One aspect of the invention comprises a method comprising the step of culturing microorganisms immobilized on a solid support in a fermentation process to produce a solvent, wherein the microorganisms are mutants and exhibit at least 125% tolerance for the solvent compared to the solvent tolerance for a corresponding non-mutant microorganism.

In some embodiments of the method, the mutant microorganisms exhibit at least 150% tolerance to the solvent. In some embodiments of the method, the mutant microorganisms exhibit at least 200% tolerance to the solvent. In some embodiments of the method, the mutant microorganisms exhibit at least 250% tolerance to the solvent. In some embodiments of the method, the mutant microorganisms exhibit at least 500% tolerance to the solvent. In some embodiments of the method, the mutant microorganisms exhibit at least 1,000% tolerance to the solvent.

In some embodiments of the method, the step of culturing microorganisms is performed in a bioreactor comprising a vessel, solid support, and growth media. In some embodiments of the method, the microorganisms comprise bacteria or fungi. In some embodiments of the method, the microorganisms comprise a single species. In some embodiments of the method, the microorganisms comprise a mixed culture of strains from the same species. In some embodiments of the method, the microorganisms comprise a mixed culture of different species. In some embodiments of the method, the microorganisms comprise environmental isolates.

In some embodiments of the method, the microorganisms comprise the genera *Clostridium, Enterococcus, Klebsiella, Lactobacillus*, or *Bacilus*. In some embodiments of the method, the microorganisms comprises *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium tetanomorphum*, or *Clostridium thermosaccharolyticum*.

In some embodiments of the method, the mutant microorganism is *Clostridium acetobutylicum, Clostridium saccharobutylicum*, or *Clostridium beijerinckii* and exhibits tolerance to at least 2% butanol. In some embodiments of the method, the mutant microorganism is *Clostridium acetobutylicum, Clostridium saccharobutylicum*, or *Clostridium beijerinckii* and exhibits tolerance to at least 2.5% butanol. In some embodiments of the method, the mutant microorganism is *Clostridium acetobutylicum, Clostridium saccharobutylicum*, or *Clostridium beijerinckii*. In some embodiments of the method, the mutant microorganism is *Clostridium acetobutylicum, Clostridium saccharobutylicum*, or *Clostridium beijerinckii* and exhibits tolerance to at least 5% butanol. In some embodiments of the method, the mutant microorganism is *Clostridium acetobutylicum, Clostridium saccharobutylicum*, or *Clostridium beijerinckii*. In some embodiments of the method, the mutant microorganism is *Clostridium acetobutylicum, Clostridium saccharobutylicum*, or *Clostridium beijerinckii* and exhibits tolerance to at least 10% butanol. In some embodiments of the method, the mutant microorganism is *Clostridium acetobutylicum, Clostridium saccharobutylicum*, or *Clostridium beijerinckii* and exhibits tolerance to at least 12% butanol. In some embodiments of the method, the mutant microorganism is *Clostridium acetobutylicum, Clostridium saccharobutylicum*, or *Clostridium beijerinckii* and exhibits tolerance to at least 15% butanol.

In some embodiments, the method comprises the step of immobilizing mutant microorganisms on a solid support by circulating fermentation media containing mutant cells through the bioreactor. In some embodiments of the method, the microorganisms are in logarithmic growth state.

In some embodiments of the method, the microorganisms are selected for solvent tolerance on a first solid support prior to culturing on an immobilized second solid support. In some embodiments of the method, the first solid support comprises agar.

In some embodiments of the method, the microorganisms are cultured in liquid media containing a mutagen prior to selection on the first solid support. In some embodiments of the method, the solid support comprises a porous material. In some embodiments of the method, the solid support comprises a material selected from the group consisting of bone char, synthetic polymers, natural polymers, inorganic materials, or organic materials. In some embodiments of the method, the solid support comprises a composite material of two or more materials of said group. In some embodiments of the method, the solid support comprises an organic material comprising a feedstock. In some embodiments of the method, the feedstock comprises corn starch or cellulosic biomass. In some embodiments of the method, the solid support comprises cellular biomass or agglomerations of cellular biomass. In some embodiments of the method, the solid support comprises organic molecules formed during Maillard reactions. In some embodiments, the solid support comprises organic precipitate formed in the media.

In some embodiments of the method, the fermentation process comprises using at least two bioreactors arranged in series or in parallel. In some embodiments, the method comprises the use of suspension culture in at least one of the least two bioreactors. In some embodiments of the method, the fermentation process of at least one of the at least two bioreactors is a continuous culture. In some embodiments of the method, the at least one continuous culture receives fermentation effluent from another culture. In some embodiments of the method, at least one continuous culture has a higher solvent tolerance than the culture producing the fermentation effluent. In some embodiments of the method, the fermentation process comprises batch, fed-batch, or continuous culture. In some embodiments of the method, the fermentation process comprises extractive fermentation wherein the solvent product is continuously extracted. In some embodiments of the method, the fermentation process is aerobic, anaerobic or microaerobic.

In some embodiments of the method, the continuous culture comprises the continuous addition of fresh media and the continuous removal of the fermentation effluent from the culture. In some embodiments of the method, the continuous culture comprises maintaining the mutant microorganisms in a logarithmic growth state. In some embodiments of the method, the immobilized mutant microorganisms comprise *Clostridium* tolerant to at least 2% butanol.

In some embodiments of the method, the solvent is selected from the group consisting of aldehydes, ketones, or alcohols. In some embodiments of the method, the solvent comprises an aldehyde selected from acetaldehyde, butyraldehyde, or propionaldehyde. In some embodiments of the method, the solvent comprises a ketone selected from acetone or butanone. In some embodiments of the method, the solvent comprises an alcohol selected from methanol, ethanol, propanol, isopropanol, butanol, 1-butanol, 2-butanol, isobutanol, 1,3-propanediol, 2,3-propanediol, 2,3-butanediol, 2-methyl-1-butanol, 3-methyl-1-butanol, 2-phenylethanol, and glycerol.

One aspect of the invention comprises a system comprising a bioreactor comprising growth medium in contact with a solid support and microorganisms immobilized on the solid support, wherein the microorganisms are mutant microorganisms that exhibit at least 125% tolerance for a solvent compared to the solvent tolerance for a corresponding non-mutant microorganism.

In some embodiments of the system, the mutant microorganisms exhibit at least 150% tolerance to the solvent. In some embodiments of the system, the mutant microorganisms exhibit at least 200% tolerance to the solvent. In some embodiments of the system, the mutant microorganisms exhibit at least 250% tolerance to the solvent. In some embodiments of the method, the mutant microorganisms exhibit at least 500% tolerance to the solvent. In some embodiments of the method, the mutant microorganisms exhibit at least 1,000% tolerance to the solvent.

In some embodiments of the system, the bioreactor further comprises an anaerobic or microaerobic environment. In some embodiments, the system comprises at least one further bioreactor, wherein the bioreactors are arranged in series or parallel. In some embodiments, the system comprises at least two of the bioreactors comprise microorganisms from different species or different strains from the same species. In some embodiments, the system comprises at least one bioreactor comprises suspended microorganisms and at least one bioreactor comprises immobilized microorganisms. In some embodiments, the system comprises two bioreactors arranged in series, wherein the effluent from the first bioreactor in the series comprises a feed stream for the second bioreactor.

In some embodiments, the system is adapted for batch, fed-batch, or continuous cultures. In some embodiments, the system is adapted for extractive fermentation wherein the solvent product is continuously extracted. In some embodiments, the system comprises a means for maintaining the microorganisms in a continuous culture. In some embodiments of the system, the fermentation process is a continuous culture, further comprising the recycle and reutilization of fermentation broth nutrients and minerals recovered during solvent purification.

In some embodiments of the system, the microorganisms are selected for solvent tolerance on a first solid support prior to culturing on an immobilized second solid support. In some embodiments of the system, the first solid support comprises agar. In some embodiments of the system, the microorganisms are cultured in liquid media containing a mutagen prior to selection on the first solid support.

In some embodiments of the system, the solid support comprises a porous material. In some embodiments of the system, the solid support comprises a material selected from the group consisting of bone char, synthetic polymers, natural polymers, inorganic materials, or organic materials. In some embodiments of the system, the solid support comprises an organic material comprising feedstock. In some embodiments of the system, the solid support comprises a feedstock comprising corn starch or cellulosic biomass. In some embodiments of the system, the solid support comprises a composite material of two or more materials of said group.

In some embodiments of the system, the microorganisms comprise bacteria and/or fungi. In some embodiments of the system, the microorganisms comprise a single species. In some embodiments of the system, the microorganisms comprise a mixed culture of strains from the same species. In some embodiments of the system, the microorganisms comprise a mixed culture of different species. In some embodiments of the system, the fermentation culture, generated by a species or mixed culture species of microorganisms, is transferred into another fermentation culture comprising different species or mixed culture of species.

In some embodiments of the system, the microorganisms comprise the genera *Clostridium, Enterococcus, Klebsiella, Lactobacillus*, or *Bacillus*. In some embodiments of the system, the microorganisms comprise *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium tetanomorphum*, or *Clostridium thermosaccharolyticum*.

In some embodiments of the system, the mutant microorganism is *Clostridium acetobutylicum* or *Clostridium saccharobutylicum*. In some embodiments of the system, the mutant microorganism is *Clostridium acetobutylicum* or *Clostridium saccharobutylicum* and exhibits tolerance to at least 2% butanol. In some embodiments of the system, the mutant microorganism is *Clostridium acetobutylicum* or *Clostridium saccharobutylicum* and exhibits tolerance to at least 2.5% butanol. In some embodiments of the system, the mutant microorganism is *C. acetobutylicum* or *C. saccharobutylicum* and exhibits tolerance to at least 5% butanol. In some embodiments of the system, the mutant microorganism is *C. acetobutylicum* or *C. saccharobutylicum* and exhibits tolerance to at least 10% butanol. In some embodiments of the system, the mutant microorganism is *C. acetobutylicum* or *C.*

*saccharobutylicum* and exhibits tolerance to at least 12% butanol. In some embodiments of the system, the mutant microorganism is *C. acetobutylicum* or *Clostridium saccharobutylicum* and exhibits tolerance to at least 15% butanol.

In one aspect of the invention, a method for making a product in a bioreactor is provided comprising: i) culturing microorganisms that are adapted or mutagenized so that the exhibit at least a 150% product tolerance for the product compared to the product tolerance of a corresponding non-adapted or non-mutagenized microorganisms; and ii) harvesting said product. In some embodiments, the adapted or mutant microorganisms exhibit at least 200% tolerance to the product, at least 500% tolerance to the product, or at least 1000% tolerance to the product.

In some embodiments of the invention, the microorganisms comprises bacteria or fungi. In some embodiments, the microorganisms comprise a single species, while in other embodiments the microorganisms comprise a mixed culture of strains from the same species or different species. In some embodiments, the microorganisms are in logarithmic growth state.

In some embodiments, the microorganisms comprise the genera *Clostridium, Enterococcus, Klebsiella, Lactobacillus*, or *Bacillus*. In other embodiments, the microorganisms comprises *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium tetanomorphum*, or *Clostridium themosaccharolyticum*. In some embodiments, these *Clostridium* species produce butanol. In other embodiments the *Clostridium acetobutylicum, Clostridium saccharobutylicum* or *Clostridium beijerinckii* exhibits tolerance to at least 2% butanol, at least 2.5% butanol, at least 5% butanol, at least 10% butanol, at least 12% butanol, or at least 15% butanol.

In some embodiments, the microorganisms are immobilized on a solid support. In other embodiments, immobilization is accomplished by circulating fermentation media containing adapted or mutant cells through the bioreactor. In some embodiments, the circulating fermentation media contains adapted or mutant microorganisms immobilized on the solid support.

In some embodiments, the microorganisms are selected for product tolerance on a first solid support prior to culturing on an immobilized second solid support. In some embodiments, the first solid support comprises agar. In some embodiments, the microorganisms exhibit enhanced product tolerance on a solid support compared to product tolerance exhibited in a liquid media. In other embodiments, the solid support is semi-solid or solid. In further embodiments, the solid support comprises a porous material. In still further embodiments, the solid support comprises a material selected from the group consisting of bone char, synthetic polymers, natural polymers, inorganic materials, or organic materials. In some embodiments, the solid support comprises a composite material of two or more materials of said group. In other embodiments, the solid support comprises an organic material comprising a feedstock. In further embodiments, the feedstock comprises corn starch or cellulosic biomass. In other embodiments, the organic matter comprises cellular biomass or agglomerations of cellular biomass. In another embodiment, the organic matter comprises precipitates formed during feed stock preparation and/or during fermentation. In a still further embodiment, the solid support comprises organic molecules formed during Maillard reactions.

In some embodiments, the culturing step comprises using at least two bioreactors arranged in series or in parallel. In some embodiments, at least one suspension culture is included in the at least two bioreactors. In further embodiments, immobilized cultures are used in at least two of the at least two bioreactors. In other embodiments, at least one of the at least two bioreactors is a continuous culture. In further embodiments, at least one continuous culture receives fermentation effluent from another culture. In a still further embodiment, the at least one continuous culture has a higher product tolerance than the culture producing the fermentation effluent.

In some embodiments, the culturing step comprises culturing the microorganisms in batch, fed-batch, or continuous culture. In further embodiments, the culturing step is performed in a packed or fluidized bed bioreactor.

In still other embodiments, the fluidized bed bioreactor is an expanded bed bioreactor. In some embodiments, the culturing step is performed in a bioreactor adapted for operation in either a packed bed or fluidized bed mode.

In some embodiments, the bioreactor comprises: a) a packed bed zone, said packed bed zone adapted to hold a solid support; b) a bed expansion zone coupled to said packed bed zone, said bed expansion zone adapted to hold said solid support when said bioreactor is operated in an expanded bed mode; and c) a particle disengagement zone coupled to said bed expansion zone, said particle disengagement zone adapted to prevent egress of said solid support from said bioreactor.

In some embodiments, the bioreactor further comprises an inlet distribution zone coupled to the packed bed zone. In other embodiments, the column further comprises a column expansion zone. In further embodiments, the bioreactor has a pressure drop in the inlet distribution zone that is no more than 30% of the total pressure drop across the length of the bioreactor. In other embodiments, the diameter of the particle disengagement zone is larger than the diameter of the packed bed zone or the expanded bed zone. In some embodiments, continuous culture comprises the continuous addition of fresh media and the continuous removal of the fermentation effluent from the culture. In other embodiments, continuous culture comprises maintaining the adapted or mutant microorganisms in a logarithmic growth state.

In some embodiments, the microorganisms comprise a *Clostridium* species tolerant to at least 2% butanol. In other embodiments, the culturing step is performed under anaerobic, microaerobic, or aerobic conditions. In some embodiments, the product is selected from the group consisting of organic acids, aldehydes, ketones, or alcohols. In further embodiments, the organic acid is selected from formic acid, acetic acid, lactic acid, propionic acid, butyric acid, succinic acid, adipic acid, or amino acids. In still further embodiments, the aldehyde is selected from acetaldehyde, butyraldehyde, or propionaldehyde. In other embodiments, the ketone is selected from acetone or butanone. In still further embodiments, the alcohol is selected from methanol, ethanol, propanol, isopropanol, butanol, 1-butanol, 2-butanol, isobutanol, 1,3-propanediol, 2,3-propanediol, 2,3-butanediol, 2-methyl-1-butanol, 3-methyl-1-butanol, 2-phenylethanol, and glycerol. In other embodiments, the product is an inhibitory product selected from the group consisting of 5-hydroxymethylfurfural, furfural, acetic acid, glucouronic acid and levulenic acid.

In some embodiments, the harvesting step comprises continuously extracting the product from the culture. In other embodiments, continuous extraction is performed with the use of a stripping gas, solvent, absorbent material, pervaporation membrane, or distillation.

In some embodiments, the culturing step comprises culturing the *Clostridium acetobutylicum, Clostridium saccharobutylicum* or *Clostridium beijerinckii* under conditions that provide for a butanol productivity of at least 6 g/L/hr at least 8 g/L/hr, or at least 10 g/L. In some embodiments, the culturing step comprises culturing the *Clostridium acetobutylicum, Clostridium saccharobutylicum* or *Clostridium beijerinckii* under conditions that provide for a total solvent productivity of at least 10 g/L/hr or at least 13 g/L. In some embodiments, at least 1000 liters of butanol are produced per day or at least 1500 liters of total solvents are produced per day.

In some embodiments, the culturing step comprises culturing for at least 7 days or at least 30 days.

In some embodiments, the microorganisms comprise a heterologous gene. In further embodiments, the heterologous gene encodes an enzyme in a product biosynthetic pathway. In still further embodiments, the enzyme is selected from the group consisting of phosphotransacetylase, acetate kinase, NAD-dependent beta-hydroxybutyryl-CoA dehydrogenase, butyryl-CoA dehydrogenase, 3-hydroxybutyryl-COA dehydratase, acetyl-CoA acetyltransferase, butyrate kinase, phosphate butyryltransferase, NADH-dependent butanol dehydrogenase B, NADH-dependent butanol dehydrogenase A, aldehyde-alcohol dehydrogenase, acetyl coenzyme A acetyltransferase, aldehyde dehydrogenase, butyrate-acetoacetate COA-transferase subunit A, butyrate-acetoacetate COA-transferase subunit B, and acetoacetate decarboxylase.

In one aspect, a system for making a product is provided comprising a bioreactor comprising: a) growth medium in contact with a solid support; b) microorganisms immobilized on the solid support, wherein the microorganisms are adapted or mutagenized so as to exhibit at least a 150% product tolerance for the product compared to the product tolerance of a corresponding non-adapted or non-mutagenized microorganisms. In some embodiments, the adapted or mutant microorganisms exhibit at least 200% tolerance, at least 500% tolerance, or at least 1000% tolerance to the product. In some embodiments, the microorganisms comprise the genera *Clostridium, Enterococcus, Klebsiella, Lactobacillus*, or *Bacillus*. In further embodiments, the microorganisms comprises *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium tetanomorphum*, or *Clostridium thermosaccharolyticum*. In still further embodiments, the adapted or mutant microorganisms are *Clostridium acetobutylicum, Clostridium saccharobutylicum* or *Clostridium beijerinckii*. In some embodiments, the product is butanol. In further embodiments, the microorganisms are *Clostridium acetobutylicum, Clostridium saccharobutylicum* or *Clostridium beijerinckii* exhibits tolerance to at least 2% butanol, to at least 2.5% butanol, to at least 5% butanol, or to at least 10% butanol.

In some embodiments, the microorganisms comprise a heterologous gene. In further embodiments, the heterologous gene encodes an enzyme in a product biosynthetic pathway. In still further embodiments, the enzyme is selected from the group consisting of phosphotransacetylase, acetate kinase, NAD-dependent beta-hydroxybutyryl-CoA dehydrogenase, butyryl-CoA dehydrogenase, 3-hydroxybutyryl-COA dehydratase, acetyl-CoA acetyltransferase, butyrate kinase, phosphate butyryltransferase, NADH-dependent butanol dehydrogenase B, NADH-dependent butanol dehydrogenase A, aldehyde-alcohol dehydrogenase, acetyl coenzyme A acetyltransferase, aldehyde dehydrogenase, butyrate-acetoacetate COA-transferase subunit A, butyrate-acetoacetate COA-transferase subunit B, and acetoacetate decarboxylase.

In some embodiments, the system comprising means for maintaining the microorganisms in a continuous culture. In some embodiments, the fermentation process is a continuous culture, further comprising the recycle and reutilization of fermentation broth nutrients and minerals recovered during product purification. In other embodiments, the microorganisms exhibit enhanced product tolerance on a solid support compared to the product tolerance exhibited in a liquid support. In some embodiments, the solid support comprises a porous material. In other embodiments, the solid support comprises a material selected from the group consisting of bone char, synthetic polymers, natural polymers, inorganic materials, or organic materials. In further embodiments, the solid support comprises an organic material comprising feedstock.

In some embodiments, the product is selected from the group consisting of organic acids, aldehydes, ketones, or alcohols. In further embodiments, the organic acid is selected from formic acid, acetic acid, lactic acid, propionic acid, butyric acid, succinic acid, adipic acid, or amino acids. In other embodiments, the aldehyde is selected from acetaldehyde, butyraldehyde, or propionaldehyde. In still further embodiments, the ketone is selected from acetone or butanone. In some embodiments, the alcohol is selected from methanol, ethanol, propanol, isopropanol, butanol, 1-butanol, 2-butanol, isobutanol, 1,3-propanediol, 2,3-propanediol, 2,3-butanediol, 2-methyl-1-butanol, 3-methyl-1-butanol, 2-phenylethanol, and glycerol.

In some embodiments of the system, *Clostridium acetobutylicum, Clostridium saccharobutylicum* or *Clostridium beijerinckii* are cultured under conditions that provide for a butanol productivity of at least 6 g/L/hr, at least 8 g/L/hr, or at least 10 g/L/hr. In some embodiments, the *Clostridium acetobutylicum, Clostridium saccharobutylicum* or *Clostridium beijerinckii* are cultured under conditions that provide for a total solvent titer of at least 10 g/L or at least 13 g/L. In some embodiments the system produces at least 1000 liters of butanol per day or at least 1500 liters of total solvents are produced per day.

In one aspect, a bioreactor is provided comprising: a) a packed bed zone, said packed bed zone adapted to hold solid support; b) a bed expansion zone coupled to said packed bed zone, said bed expansion zone adapted to hold said solid support when said bioreactor is operated in an expanded bed mode; and c) a particle disengagement zone coupled to said bed expansion zone, said particle disengagement zone adapted to prevent egress of said solid support from said bioreactor. In some embodiments, the ratio of the combined height of said packed bed zone and said bed expansion zone (H) to the height of the packed bed zone ($H_p$) is greater than 1.01, 1.05, 1.10, 1.15, or 1.20.

In some embodiments, the bioreactor further comprises of a column expansion zone adapted to be positioned between the bed expansion zone and the particle disengagement zone, wherein the upstream end of the column expansion zone is coupled to the bed expansion zone and the downstream end of the column expansion zone is coupled to the particle disengagement zone. In some embodiments, the column expansion zone comprises an angled slope that slants upwards by at least 10° or at least 30° from the horizon. In some embodiments, the bioreactor further comprises of a gas-liquid separation zone coupled to the particle disengagement zone. In some embodiments, the bioreactor is configured to operate in either packed bed mode or in expanded bed mode. In other embodiments, the bioreactor is further configured to alternate between operation in packed bed mode and expanded bed mode. In some embodiments, the bioreactor is capable of continuous fermentation for at least 100 hours, at least 500 hours or at least 1000 hours.

In some embodiments, the solid support is semi-solid or solid. In other embodiments, the solid support comprises a porous material. In further embodiments, the solid support comprises a surface area of at least 50 m$^2$/g. In still further embodiments, the solid support comprises a bulk density of at least 0.3 g/cm$^3$. In other embodiments, the solid support comprises a ball-pan hardness number of at least 60. In further embodiments, the solid support comprises a yield strength of at least 20 MaP.

In some embodiments, the solid support comprises a material selected from the group consisting of bone char, synthetic polymers, natural polymers, inorganic materials, or organic materials. In other embodiments, the solid support comprises a composite material of two or more materials of said group. In further embodiments, the solid support comprises an organic material comprising a feedstock. In still further embodiments, the feedstock comprises corn starch, cellulosic biomass, cellular biomass, agglomerations of cellular biomass, precipitates formed during feed stock preparation and/or during fermentation or organic molecules formed during Maillard reactions.

In one aspect, a bioreactor is provided for fermenting a biological product on solid support comprising: a) a packed bed zone, comprising solid support therein, said solid support comprising microorganisms thereon for fermenting said biological product; b) a bed expansion zone coupled to said packed bed zone adapted for containing said solid support when said bioreactor is operated in an expanded bed mode; and c) a particle disengagement zone coupled to said bed expansion zone, said particle disengagement zone adapted for preventing egress of said solid support from said bioreactor. In some embodiments, the ratio of the combined height of said packed bed zone and said bed expansion zone (H) to the height of the packed bed zone ($H_p$) is greater than 1.01, 1.05, 1.10, 1.15, or 1.20.

In some embodiments, the bioreactor further comprising a column expansion zone adapted to be positioned between the bed expansion zone and the particle disengagement zone, wherein the upstream end of the column expansion zone is coupled to the bed expansion zone and the downstream end of the column expansion zone is coupled to the particle disengagement zone.

In some embodiments, the column expansion zone comprises an angled slope that slants upwards by at least 10° or at least 30° from the horizon. In some embodiments, the bioreactor further comprising a gas-liquid separation zone coupled to the particle disengagement zone. In some embodiments, the bioreactor is configured to operate in either packed bed mode or in expanded bed mode. In some embodiments, the bioreactor is further configured to alternate between operation in packed bed mode and expanded bed mode. In some embodiments, the bioreactor is capable of continuous fermentation for at least 100 hours, at least 500 hours, or at least 1000 hours.

In some embodiments, the microorganisms comprise the genera *Clostridium, Enterococcus, Klebsiella, Lactobacillus,* or *Bacillus*. In other embodiments, the microorganisms comprises *Clostridium acetobutylicum, Clostridium beijerinckii, Clostridium puniceum, Clostridium saccharobutylicum, Enterococcus faecium, Enterococcus gallinarium, Clostridium aurantibutyricum, Clostridium tetanomorphum,* or *Clostridium thermosaccharolyticum*.

In some embodiments the microorganisms produce butanol. In further embodiments, *Clostridium acetobutylicum, Clostridium saccharobutylicum* or *Clostridium beijerinckii* exhibits tolerance to at least 2% butanol, at least 2.5% butanol, at least 5% butanol, or at least 10% butanol.

In some embodiments, the microorganisms are immobilized on the solid support by circulating fermentation media containing the microorganisms through the bioreactor. In further embodiments, the circulating fermentation media comprises microorganisms immobilized on particles. In some embodiments, the microorganisms are in logarithmic growth state.

In some embodiments, the solid support is semi-solid or solid. In further embodiments, the solid support comprises a porous material. In still further embodiments, the solid support comprises a material selected from the group consisting of bone char, synthetic polymers, natural polymers, inorganic materials, or organic materials. In some embodiments, the solid support comprises a composite material of two or more materials of said group. In other embodiments, the solid support comprises an organic material comprising a feedstock, cellular biomass, agglomerations of cellular biomass, organic matter comprises precipitates formed during feed stock preparation and/or during fermentation, or organic molecules formed during Maillard reactions. In further embodiments, the feedstock comprises corn starch or cellulosic biomass.

In one aspect of the invention, a method is provided for making a biological product comprising: a) culturing microorganisms in a bioreactor comprising: i) a packed bed zone, comprising solid support therein, said solid support comprising microorganisms thereon for fermenting said biological product; ii) a bed expansion zone coupled to said packed bed zone adapted for containing said solid support when said bioreactor is operated in an expanded bed mode; and iii) a particle disengagement zone coupled to said bed expansion zone, said particle disengagement zone adapted for preventing egress of said solid support from said bioreactor; and b) harvesting the product.

BRIEF DESCRIPTION OF THE DRAWINGS

FIG. 2A shows $OD_{600}$ measurements at various time points and butanol concentrations.

FIG. 2B shows $OD_{600}$ measurements of starter cultures following 1:20 inoculations.

FIG. 6A is a table showing the three strains, Co-5673, Co-7449, and Co-0124 were analyzed for butanol tolerance on solid media (P2+4% Xylose) at 24 hours. Observed growth indicated butanol tolerance.

FIG. 6B is a comparison of the butanol tolerance of the three strains grown in liquid and on solid media at the 24 hr time point.

FIG. 7A is a table showing the three strains, Co-5673, Co-7449, and Co-0124 were analyzed for butanol tolerance on solid media (P2+4% Xylose) at 96 hours. Observed growth indicated butanol tolerance.

FIG. 7B is a comparison of the butanol tolerance of the three strains grown in liquid and on solid media at the 96 hr time point.

FIG. 13A show the parameters used to calculate bed expansion levels for bonechar type 5×8. Results are in the form of ratios for expanded bed height to packed bed height ($H/H_{packed}$).

FIG. 13B, is a graphical representation of the bed expansion for bonechar type 5×8.

FIG. 14A show the parameters used to calculate bed expansion levels for bonechar type 10×28. Results are in the form of ratios for expanded bed height to packed bed height ($H/H_{packed}$).

FIG. 14B, is a graphical representation of the bed expansion for bonechar type 10×28.

FIG. 20 is a table showing experiment data collected to support the bioreactor design and modeling.

FIG. 27 is a chart summarizing the experimental data obtained during continuous production of butanol in immobilized cell bioreactors.

DETAILED DESCRIPTION OF THE INVENTION

Figure 1:
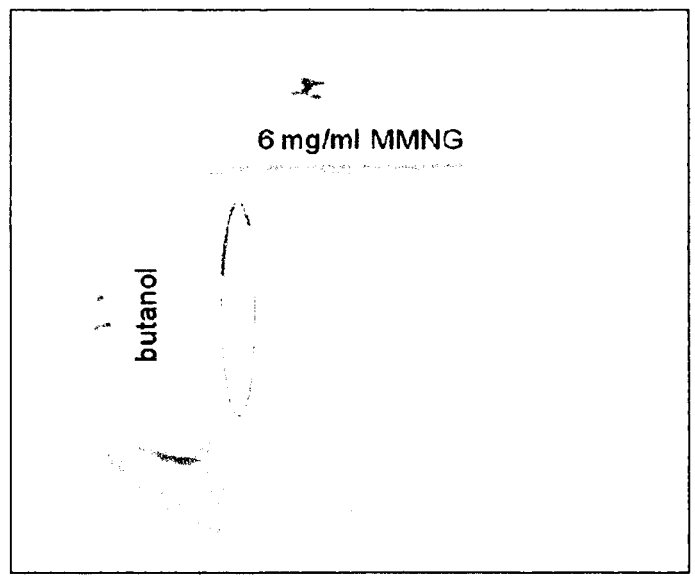
FIG. 1 is a picture showing the set up of the double disc mutagenesis assay.

This invention provides methods and materials for increasing the total yield of products from cultures of microorganisms. The methods are achieved by adapting or selecting microorganisms on semi-solid or solid support that demonstrate high tolerance to products including organic acids, like acetic and butyric acids, and solvents such as alcohols, aldehydes and ketones. The microorganisms are then cultured on semi-solid or solid support under product producing conditions in a bioreactor where the selected microorganisms surprisingly, maintain their tolerance for products and exhibit at least a 125% greater tolerance for a specific product compared to the original parent stock or stocks of microorganisms. The microorganisms of this invention include bacteria and fungi. The microorganisms of the invention can be derived from microorganisms recently isolated from the environment, from known cultures, mutants or from cultures that are genetically modified. In some embodiments, mixed cultures of different strains from the same species or mixed cultures of different species are used.

This invention contemplates the use of these methods to produce products created along a biochemical, metabolic, synthetic or fermentative pathways. This invention is applicable to any product producing pathway, whether naturally occurring, partially genetically engineered, or totally genetically engineered. It further includes microorganisms wherein the expression of one or more genes in a competing pathway that draws intermediates away from a product producing pathway are knocked out or engineered to have reduced expression. One example of a naturally occurring fermentative pathway that produces an organic acid is the homolactic acid fermentation pathway of *Lactobacillus* species. An example of a natural occurring fermentative pathway that produces a solvent is the ethanolic pathway of *Saccharomyces cerevisiae*. Another example of a solvent pathway is the butylic pathway of *Clostridium acetobutylicum*. An example of a partially genetically engineered fermentative pathway is the ethanolic pathway engineered into *E. coli*. An example of a partially genetically engineered synthetic pathway is the four carbon alcohol pathway engineered into *E. coli*.

Acids

The methods of the present invention are useful for the production of organic acids. These include, for example, formic acid, acetic acid, lactic acid, propionic acid, butyric acid, succinic acid and other dicarboxylic acids, adipic acid, and amino acids. Of particular interest is the production by microorganisms of organic acids useful as food or pharmaceutical additives, or industrial chemicals.

Solvents

The methods of the present invention are useful for the production of industrial solvents. These include, for example, alcohols (ethanol, butanol, propanol, isopropanol, 1,2-propanediol 1,3-propanediol, 2,3-propanediol, 1,2-butanediol, 2,3-butanediol, 1,2,4-butanetriol, 1,2-pentanediol, 1,2-hexanediol, glycerol, n-pentanol and its isomers, n-hexanol and its isomers, n-heptanol and its isomers, n-octanol and its isomers), aldehydes (acetaldehyde, butyraldehyde) and ketones (acetone, butanone). Of particular interest is the production by microorganisms of solvents useful as fuels and industrial chemicals. In some embodiments, the methods of the invention are useful for increasing the production of butanol, a high value biofuel, by *C. acetobutylicum, C. beijerinckii, C. puniceum*, or *C. saccharobutylicum*.

Further Adapted or Selected Tolerances

The methods herein are also useful for isolating adapted or selected microorganisms that have increased tolerance to intermediate species produced in a fermentative, metabolic, respiratory or synthetic pathway. Additionally, increased product tolerance may be indirect and rely on decreased inhibitory effects of inhibitory agents, including, but not limited to, HMF, furfural, levulenic acid, glucuronic acid, autolysins or acetic acid. Inhibitory agents may be generated by the organism or be present in the initial feed. Inhibitory agents or species may be formed along fermentative, metabolic, respiratory or synthetic pathways. Increased tolerance to inhibitory agents may increase productivity of desired products, such as ethanol, butanol, etc. In one embodiment, the inhibitory agent to which increased tolerance is achieved compared to an unadapted or unmutagenized and selected microorganism is selected from the group consisting of HMF, furfural, levulinic acid, glucuronic acid, and acetic acid.

Fermentative Pathways

A fermentative pathway is a metabolic pathway that proceeds anaerobically, wherein an organic molecule functions as the terminal electron acceptor rather than oxygen, as happens with oxidative phosphorylation under aerobic conditions. Glycolysis is an example of a wide-spread fermentative pathway in bacteria (*C. acetobutylicum* and *E. coli*) and yeast. During glycolysis, cells convert simple sugars, such as glucose, into pyruvate with a net production of ATP and NADH. At least 95% of the pyruvate is consumed in short pathways which regenerate $NAD^+$, an obligate requirement for continued glycolysis and ATP production. The waste or end products of these $NAD^+$ regeneration systems are referred to as fermentation products. Depending upon the organism and culturing conditions, pyruvate is ultimately converted into end products such as organic acids (formic acid, acetic acid, lactic acid, pyruvate, butyric acid, succinic acid and other dicarboxylic acids, adipic acid, and amino acids), and neutral solvents (ethanol, butanol, acetone, 1,3-propanediol, 2,3-propanediol, acetaldehyde, butyraldehyde, 2,3-butanediol).

The Comprehensive Microbial Resource (CMR) of TIGR lists nine types of fermentation pathways in its atlas based on the fermentative end product: homolactic acid (lactic acid); heterolactic acid (lactic acid), ethanolic, propionic acid, mixed (formic and acetic acid), butanediol, butyric acid, amino acid, and methanogenesis. The method of this invention can be used in any fermentative pathway where an acid or solvent is produced at any stage of the pathway. The fermentative pathways described in this invention can be naturally occurring, altered by chemical mutagenesis, semi- or completely genetically engineered.

Solvent Producing Fermentative Pathways

Native

Via the well known pathway of glycolysis, yeasts convert one hexose molecule into two ethanol molecules and two carbon dioxide molecules. Many species of *Clostridium* produce solvents fermentatively. In *C. acetobutylicum* the solvents acetone, butanol and ethanol (ABE) are produced in a roughly 3:6:1 ratio by weight. Other solvents produced as intermediates include acetaldehyde and butyraldehyde.

Genetically Engineered-*E. coli*

Ethanol

The bacterium *E. coli* produces a minimal level of ethanol when grown anaerobically owing to its lack of the enzyme pyruvate decarboxylase. A semi-genetically engineered fermentative enthanolic pathway can be created in *E. coli* by expressing alcohol dehydrogenase II (adhB) and pyruvate decarboxylase (pdc) cloned from *Z. mobilis*. (Conway et al. (1987a) J. Bacteriol. 169:2591-2597; Neale et al. (1987) Nucleic Acids Res. 15:1752-1761; Ingram and Conway [1988] Appl. Environ. Microbiol. 54:397-404; Ingram et al. (1987) Appl. Environ. Microbiol. 53:2420-2425). Ethanol productivity corresponds directly to the expression level of the *Z. mobilis* ethanologenic genes. The generality of this approach was later demonstrated in two other enteric bacteria, *Erwinia chrysanthemi* and *Klebsiella planticola*. (Tolan and Finn. Appl. Environ. Microbiol. 53:2033-2038, 2039-2044, 1987; Beall et al., 1993; Ingram and Conway, 1988; Wood and Ingram, 1992.)

4 Carbon and Higher Alcohols

Higher alcohols including isobutanol, 1-butanol, 2-methyl-1-butanol, 3-methyl-1-butanol and 2-phenylethanol can be expressed in *E. coli* by harnessing the bacterium's amino acid biosynthetic pathway. The 2-keto acid intermediates produced in this pathway can be diverted to alcohol production by genetically engineering the expression of two heterologous enzymes, 2-keto-acid decarboxylase and alcohol dehydrogenase found in the last two steps in the Ehrlich pathway. (Shota A., et al. Non-fermentative pathways for synthesis of branched-chain higher alcohols as biofuels. Nature, Vol 451/3 Jan. 2008.)

Cells and Cultures

Microorganisms

The present invention provides for the adaptation or selection of strains, environmental isolates, and mutant microorganisms with increased product tolerance compared to those of the corresponding non-mutant microorganism. The methodologies disclosed are applicable to a wide range of microorganisms including bacteria and fungi. The methods herein are also useful for adaptation and selection for the microorganism's adhesion or ability to grow and attach to a solid support of choice. Microorganisms are plated or placed on solid support with substrate and cultured. The cultures are subjected to one or more cycles in which the solid support is rinsed to remove non- or weakly adherent microorganisms followed by the addition of more media to allow the remaining microorganisms to increase their numbers. Those that exhibit enhanced or rapid growth on the solid support are selected and stored for later use. Picked isolates can be further improved through adaptation or mutagenesis and selection for increased product tolerance. Picked isolates can also be transformed to express a heterologous gene that confers increased product tolerance or increase product production.

In some embodiments, the microorganisms are fungi and the fungi are yeasts. Examples of yeasts include, but are not limited to, *Saccharomyces cerevisiae, S. bayanus, S. carlsbergensis, S. Monacensis, S. Pastorianus, S. uvarum* and *Kluyveromyces* species. Other examples of anaerobic or aerotolerant fungi include, but are not limited to, the genera *Neocallimastix, Caecomyces, Piromyces* and other rumen derived anaerobic fungi.

In some embodiments, the microorganisms are bacteria. Bacteria covered by this invention include Gram-negative and Gram-positive bacteria. Non-limiting examples of Gram-positive bacteria include bacteria found in the genera of *Staphylococcus, Streptococcus, Bacillus, Mycobacterium, Enterococcus, Lactobacillus, Leuconostoc, Pediococcus*, and *Propionibacterium*. Examples of specific species include *Enterococcus faecium, Enterococcus gallinarium*.

Non-limiting examples of Gram-negative bacteria include bacteria found in the genera *Pseudomonas, Zymomonas, Spirochaeta, Methylosinus, Pantoea, Acetobacter, Gluconobacter, Escherichia* and *Erwinia*.

In some embodiments, the bacteria are strict anaerobes or obligate anaerobes such as *C. acetobutylicum*. Strains of *C. acetobutylicum* contemplated for use with this invention include wild types strains such as ATCC 43084 and ATCC 824 from the American Tissue Culture Collection (ATCC) and DSM 792 and DSM 1731 from the Deutsche Sammlung von Mikroorganismen and Zellkulturen GmbH, Germany. High butanol producing strains *C. acetobutylicum* contemplated for use with this invention include strains such as ATCC 55025, and ATCC 39058 from ATCC. Another high producing strain contemplated for use with this invent is B643. (Contag, P. R., et al, Cloning of a lactate dehydrogenase gene from *Clostridium acetobutylicum* B643 and expression in *Escherichia coli*. Appl. Environ. Microbiol. 56:3760-3765, 1990.) While originally identified as *C. acetobutylicum*, B643 is now classified as *C. saccharobutylicum*. A further high producing strain contemplated for use with this invention is B18 derived from B643, (Rogers, P. and Palorsaari, N. *Clostridium acetobutylicum* mutants that produce butyraldehyde and altered quantities of solvents. Appl. Environ. Microbiol. 53:2761-2766, 1987).

Other examples of *Clostridium* contemplated for use in this invention include *C. beijerinckii* (e.g., ATCC 25752, ATCC51743, and BA101, ATCC PTA 1550 (U.S. Pat. No. 6,358,717 and U.S. application Ser. No. 10/945,551), *C. puniceum* (e.g. ATCC 43978), or *C. saccharobutylicum* (e.g., ATCC BAA-117 or Co-7449).

Further examples of species of *Clostridium* contemplated for use in this invention can be selected from *C. aurantibutyricum, C. butyricum, C. cellulolyticum, C. phytofermentans, C. saccharolyticum, C. saccharoperbutylacetonicum, C. tetanomorphum, C. thermobutyricum, C. thermocellum, C. saccharoperbutylacetonicum* or *C. thermosaccharolyticum*.

Other bacteria contemplated for use in this invention include *Corynebacteria*, such as *C. diphtheriae*, Pneumococci, such as *Diplococcus pneumoniae*, Streptococci, such as *S. pyogenes* and *S. salivarus*, Staphylococci, such as *S. aureus* and *S. albus*, Myoviridae, Siphoviridae, Aerobic Spore-forming *Bacilli*, Bacilli, such as *B. anthracis, B. subtilis, B. megaterium, B. cereus, Butyrivibrio fibrisolvens*, Anaerobic Spore-forming *Bacilli*, Mycobacteria, such as *M. tuberculosis hominis, M. bovis, M. avium, M. paratuberculosis*, *Actinomycetes* (fungus-like bacteria), such as, *A. israelii, A. bovis, A. naeslundii, Nocardia asteroides, Nocardia brasiliensis*, the Spirochetes, *Treponema pallidum, Treponema pertenue, Treponema carateum, Borrelia recurrentis, Leptospira icterohemorrhagiae, Leptospira canicola, Spirillum minus, Streptobacillus monilformis, Trypanosomas, Mycoplasmas, Mycoplasma pneumoniae, Listeria monocytogenes, Erysipelothrix rhusiopathiae, Streptobacillus monilformis, Donvania granulomatis, Bartonella bacilliformis, Rickettsiae, Rickettsia prowazekii, Rickettsia mooseri, Rickettsia rickettsiae*, and *Rickettsia conori*. Other bacteria used can include *Escherichia coli, Zymomonas mobilis, Erwinia chrysanthemi*, and *Klebsiella planticola*.

In some embodiments of this invention, the microorganisms are obligate anaerobes. A non-limiting example of obligate anaerobes include *Butyrivibrio fibrosolvens* and *Clostridium* species such as *C. pasterianum*. In other embodiments of this invention, the microorganisms are microaerotolerant and are capable of surviving in the presence of small concentrations of oxygen. In some embodiments, microaerobic conditions include, but are not limited, to fermentation conditions produced by sparging a liquid media with a gas of at least 0.01% to at least 5% or more O2 (e.g. 0.01%, 0.05%, 0.10%, 0.50%, 0.60%, 0.70%, 0.80%, 1.00%, 1.20%, 1.50%, 1.75%, 2.0%, 3%, 4%, 5% or more O2). In another aspect, the microaerobic conditions include, but are not limited to, culture conditions with at least about 0.05 ppm dissolved O2 or more (e.g. 0.05, 0.075, 0.1, 0.15, 0.2, 0.3, 0.4, 0.5, 0.6, 0.8, 1.0, 2.0, 3.0, 4.0, 5.0, 8.0, 10.0, ppm or more).

Sources of parent strains of bacteria and fungi for the development of higher product tolerant mutants include established culture collections, and researchers in universities, government institutions, or companies. Alternatively, parent strains can be isolated from environmental samples such as wastewater sludge from wastewater treatment facilities including municipal facilities and those at chemical or petrochemical plants. The latter are especially attractive as the isolated microorganisms can be expected to have evolved over the course of numerous generations in the presences of high product concentrations and thereby have already attained a level of desired product tolerance that may be further improved upon. Individual species or mixed populations of species can be isolated from environmental samples.

When mixed populations of specific species or genera are desired, a selective growth inhibitor for undesired species or genera can used to prevent or suppress the growth of these undesired microorganisms.

In some embodiments, cocultures are utilized. Frequently, one microorganism secretes enzymes into the media that break down a feedstock into constituent compounds that can be utilized by another microorganism. Examples of solvent production using cocultures of microorganisms include butanediol production with *Klebsiella pneumoniae* in a coculture with *Trichoderma harzianum* (Yu et al., Applied and Environmental Microbiology (1985) 50 (4): 924-929) and ethanol production from a coculture of *Clostridium thermocellum* and *C. thermohydrosulfuricum* (Eng et al., Applied and Environmental Microbiology (1981) 41 (6): 1337-1343).

In other embodiments, environmental isolates and/or microbial consortiums are used to generate microbial consortiums that have increased product tolerance. Isolates, including microbial consortiums can be collected from numerous environmental niches including soil, rivers, lakes, sediments, estuaries, marshes, industrial facilities, etc. In some embodiments, the microbial consortiums are strict anaerobes. In other embodiments, the microbial consortiums are obligate anaerobes. In some embodiments, the microbial consortiums are facultative anaerobes. In still other embodiments, the microbial consortiums do not contain species of *Enterococcus* or *Lactobacillus*.

In some embodiments, the microorganisms comprise one or more heterologous genes, the expression of which, increase the product tolerance of the microorganisms. In some embodiments, the one or more heterologous genes are introduced into the microorganism before adaptation or selection for product tolerance on a solid support, while in other embodiments the one or more heterologous genes are introduced into the microorganisms after adaptation or selection for product tolerance.

In some embodiments, the microorganisms are engineered to over-express endogenous genes that increase the product tolerance of the microorganisms. In some embodiments, the microorganisms comprise additional copy numbers of endogenous genes that increase resistance to products. In certain embodiments, the product tolerant microorganisms are not *E. coli* and the heterologous or over-expressed genes are not yfdE, yhhL, yhhM, and csrC. In other embodiments, the microorganisms are not recombinant microorganisms that have increased expression of heat shock proteins. In still other embodiments, the microorganisms are not recombinant microorganisms that comprise a heterologous gene that encodes a polypeptide that exports butanol out of the microorganism.

Adaptation Process

Microorganisms can be adapted or selected to grow and attach to a solid support, in the presence of a product that they normally produce or both. In some embodiments, typically, a population of microorganisms is plated or otherwise dispersed across a solid support that contains available nutrients. The nutrients can be freely available such as in the case when the solid support is agar comprising a nutrient media. Alternately, in other embodiments, the solid support can be a surface that microorganisms can colonize to form a biofilm, such as bonechar, but where the nutrients are provided by a liquid media that perfuses the solid support. Colonies of microorganisms that grow rapidly on a desired solid support can be picked and cultured, or stored for later applications.

In another embodiment, the solid support can comprise a feedstock that through enzymatic breakdown releases available nutrients as happens when starch or cellulose containing feedstock are broken down into glucose and other simpler constituents that can be assimilated by the microorganisms. Colonies of rapidly growing microorganisms can be picked from the solid support and cultured or stored for later applications.

In still another embodiment, microorganisms that are known to grow well on a select solid support can be exposed to varying concentrations of a product that they normally produce in order to select for microorganisms that can grow at higher concentrations. The exposure can be serial, such as starting with a low concentration of the product. Colonies with good growth characteristics are then picked and transferred or plated on the same solid surface wherein the microorganisms are exposed to a higher concentration of the product. Colonies with good growth characteristics can be picked and the process continued sequentially with higher concentrations as needed to produce an adapted microorganism for the intended use.

An alternate manner to adapt microorganisms to a product concentration is to maintain a continuous culture on the microorganisms on a solid substrate. The concentration of the product can be maintained at the same concentration or it can be varied over time, usually in a concentration escalating manner. As the cells grow, excess cells are generally removed and over multiple generations, more product tolerant microorganisms arise that are adapted to product concentration.

For butanol-producing *Clostridium* including but not limited to *C. acetobutylicum* or *C. saccharobutylicum*, useful acetic acid or butyric acid concentrations for adaptation include from about 0.2% to about 10%. In some embodiments, *C. acetobutylicum* or *C. saccharobutylicum* can be adapted to exhibit tolerance to acetic acid or butyric acid of at least 0.2%, 0.40%, 0.60%, 0.80%, 1.00%, 1.20%, 1.40%, 1.60%, 1.80%, 2.00%, 2.20.0%, 2.40%, 2.60%, 2.80%, 3.00%, 3.5%, 4.00%, 5.00%, 6.00%, 7.00%, or 8.00%.

For butanol-producing *Clostridium*, such as but not limited to *C. acetobutylicum* or *C. saccharobutylicum*, useful butanol concentrations for adaptation include from about 1.0% w/v to about 25% w/v, 1.5% w/v to about 22.5% w/v, 2.0% w/v to about 20.0% w/v, 2% to about 18% w/v, 2.0% w/v to about 16.0% w/v, 2% to about 15% w/v, 2.0% w/v to about 12.0% w/v, 2% to about 10% w/v, 2.0% w/v to about 9.0% w/v, 2% to about 8% w/v, 2.0% w/v to about 7.0% w/v, 2% to about 6% w/v, 2.0% w/v to about 5.0% w/v, 2% to about 4% w/v, 2.0% w/v to about 3.0% w/v, and 2% to about 2.5% w/v. Other useful butanol concentration include at least 1.0%, 1.5%, 1.8%, 2.0%, 2.2%, 2.4%, 2.6%, 2.8%, 3.0%, 3.2%, 3.4%, 3.6%, 4.0%, 5.0%, 7.0%, 10%, 12%, or 15%. Butanol adaptation concentrations includes those made solely of 1-butanol, and those composed of mixtures of butanol isomers. *C. acetobutylicum* can also be adapted to solutions that contain the ABE solvent mixtures. Useful ABE total solvent concentration ranges include those from about 1.0% w/v to about 25% w/v, 1.5% w/v to about 22.5% w/v, 2.0% w/v to about 20.0% w/v, 2% to about 18% w/v, 2.0% w/v to about 16.0% w/v, 2% to about 15% w/v, 2.0% w/v to about 12.0% w/v, 2% to about 10% w/v, 2.0% w/v to about 9.0% w/v, 2% to about 8% w/v, 2.0% w/v to about 7.0% w/v, 2% to about 6% w/v, 2.0% w/v to about 5.0% w/v, 2% to about 4% w/v, 2.0% w/v to about 3.0% w/v, and 2% to about 2.5% w/v. Other useful total ABE concentrations include at least 1.0%, 1.5%, 1.8%, 2.0%, 2.2%, 2.4%, 2.6%, 2.8%, 3.0%, 3.2%, 3.4%, 3.6%, 4.0%, 5.0%, 7.0%, 10%, 12%, or 15%.

In some embodiments, microorganisms can be adapted on a solid support to tolerate an organic acid at a level that is at least 125% greater than the level that can be tolerated by the corresponding non-adapted parent microorganism. In other embodiments, adapted microorganisms exhibit at least 150%, 200%, 250%, 300%, 400%, 500%, 600%, 700%, 800%, 900%, 1,000%, 2,000%, 3,000%, 4,000%, 5,000%, 6,000%, 7,000%, 8,000%, 9,000%, 10,000%, 11,000%, 12,000%, 13,000%, 14,000%, or 15,000% acid tolerance compared to the acid tolerance for the corresponding non-adapted parent microorganisms. If the parent microorganism is unavailable, then the comparison can be performed using a standard species or strain. For example, with *C. acetobutylicum*, a standard strain is ATCC 824.

In some embodiments, acid tolerance is an absolute value that is determined by measuring the growth ability of an adapted microorganism on a semi-solid or solid support containing a specified concentration of an acid. For example, an adapted strain of *C. saccharobutylicum* produced using the methods of the invention may have an absolute tolerance to acetic acid or butyric acid of at least 5%. In some embodiments, adapted strains of *Clostridium* exhibit tolerance to acetic acid or butyric acid of at least 2.0%, 2.5%, 3.0%, 3.5%, 4.0%, 5.0%, 6.0%, 7.0%, 8.0%, 9.0%, 10.0%, 12.5%, 15.0%, 20%, or 25%.

Selection Process

Numerous methodologies are known in the art for inducing mutations into microorganisms and selecting for a desired phenotype. Typically, microorganisms are suspended in a liquid medium that contains a mutagen at a specific concentration. After incubation for a given amount of time, the suspension is centrifuged and the resulting liquid decanted leaving a microbial pellet. The pellet is resuspended in media. This wash step can be repeated if necessary. Once the mutagen is removed, the microorganisms are often cultured in a liquid media to recover from the mutagenesis step before being diluted and then spread out on a solid nutritive medium like agar containing an agent that exerts selective pressure on the plated microorganisms.

If mutants with increased product tolerance are desired, a collection of plates representing a range of product concentrations are used. After an appropriate incubation period, colonies of product tolerant microorganisms can be selected from the solid nutritive media. By varying the mutagenesis time and the concentration of the mutagenesis agent, the mutation rate and the mortality rate of the microorganisms can be modified to find favorable conditions.

An alternative mutagenesis and selection process for n-butanol tolerant *C. acetobutylicum* is described in U.S. Pat. No. 4,757,010. In this process, mutagenesis is performed in one step on solid medium. A liquid culture of *C. acetobutylicum* is obtained that is in a growing state. This is plated at various dilutions onto plates of solid nutritive medium, each plate containing a specific concentration of n-butanol, with the collection of plates representing a range of n-butanol concentrations. Additionally, each plate has a concentration gradient of the mutagen. Typically, the mutagen is place at one point, for example, at the center of each dish from where it diffuses away creating a concentration gradient. After incubation for an appropriate amount of time n-butanol-resistant colonies are isolated.

A further method for mutagenesis and selection is to use the double disc method wherein after a culture is plated out onto one or more containers containing a semi-solid or solid support, two paper discs or strips are laid on top of the support in each container. One disc or strip is impregnated with a solution of a mutagen. The other disc or strip contains the agent to exert the selective pressure. Typically, the paper strips are used and place perpendicularly to each other to create overlapping gradients of mutagen and selective agent. FIG. 1. Near both strips there is a zone of clearing where no cells can grow. Typically, farther away from the strips, at lower overlapping concentrations, colonies of mutants may be found and isolated.

Mutagens useful in the present invention include alkylating agents such as ethylmethylsulfonate (EMS), N-methyl N'-nitro N-nitrosoguanidine (MNNG or NG), ICR 191, nitrous acid, nitroquinoline-N-oxide, N-ethyl-N-nitrosourea (ENU), and triethylene melamine. Other useful chemical mutagens include hydroxylamine, nucleoside base analogs, e.g. BrdU, DNA intercalating agents e.g. ethidium bromide, and DNA crosslinkers, e.g. cisplatin. Useful physical mutagens include ionizing radiation, e.g. x-rays, alpha particles, and beta particles, and non-ionizing radiation, e.g. ultraviolet radiation.

For butanol-producing *Clostridium*, such as but not limited to *C. acetobutylicum* or *C. saccharobutylicum*, useful butanol concentrations for selection include from about 1.0% w/v to about 25% w/v, 1.5% w/v to about 22.5% w/v, 2.0% w/v to about 20.0% w/v, 2% to about 18% w/v, 2.0% w/v to about 16.0% w/v, 2% to about 15% w/v, 2.0% w/v to about 12.0% w/v, 2% to about 10% w/v, 2.0% w/v to about 9.0% w/v, 2% to about 8% w/v, 2.0% w/v to about 7.0% w/v, 2% to about 6% w/v, 2.0% w/v to about 5.0% w/v, 2% to about 4% w/v, 2.0% w/v to about 3.0% w/v, and 2% to about 2.5% w/v. Other useful butanol concentrations include at least 1.0%, 1.5%, 1.8%, 2.0%, 2.2%, 2.4%, 2.6%, 2.8%, 3.0%, 3.2%, 3.4%, 3.6%, 4.0%, 5.0%, 7.0%, 10%, 12%, or 15%. Butanol selection concentrations includes those made solely of 1-butanol, and those composed of mixtures of butanol isomers. Solvent-producing *Clostridium*, such as but not limited to *C. acetobutylicum* or *C. saccharobutylicum*, can also be selected with solutions that contain the ABE solvent mixtures. Useful ABE total solvent concentration ranges include those from about 1.0% w/v to about 25% w/v, 1.5% w/v to about 22.5% w/v, 2.0% w/v to about 20.0% w/v, 2% to about 18% w/v, 2.0% w/v to about 16.0% w/v, 2% to about 15% w/v, 2.0% w/v to about 12.0% w/v, 2% to about 10% w/v, 2.0% w/v to about 9.0% w/v, 2% to about 8% w/v, 2.0% w/v to about 7.0% w/v, 2% to about 6% w/v, 2.0% w/v to about 5.0% w/v, 2% to about 4% w/v, 2.0% w/v to about 3.0% w/v, and 2% to about 2.5% w/v. Other useful ABE total solvent concentrations include at least 1.0%, 1.5%, 1.8%, 2.0%, 2.2%, 2.4%, 2.6%, 2.8%, 3.0%, 3.2%, 3.4%, 3.6%, 4.0%, 5.0%, 7.0%, 10%, 12%, or 15%.

In some embodiments, multiple rounds of selection or mutagenesis and selection can be used on an initially selected microorganism. Each round can be at a progressively higher product concentration. Alternatively, mutagens and/or products can be varied across multiple selection rounds.

Acid Tolerance

In some embodiments, acid tolerant microorganisms are mutagenized and selected for increased acid tolerance on solid support. In some embodiments, acid tolerant mutants can be used for either solvent or organic acid production. For example, an acid tolerant mutant of solvent-producing *Clostridium*, such as but not limited to *C. acetobutylicum* or *C. saccharobutylicum*, can be cultured under conditions conducive for acetic and butyric acid production, or alternatively, under condition conducive to butanol production. In some embodiments of the present invention, acid tolerance is a relative value that is measured by comparing the growth ability of a mutant microorganism on a semi-solid or solid support to the growth ability of the non-mutant parent microorganism on the same semi-solid or solid support. Typically, the semi-solid or solid support comprises a growth media and a specified concentration of a acid that is usually measured on a volume to volume (w/v) basis. Generally, multiple containers, usually petri dishes, are filled with semi-solid or solid support representing a range of acid concentration. For example, a useful support for testing butanol tolerance of *C. acetobutylicum*, is agar containing Reinforced *Clostridium* Medium (RCM) and a useful acetic acid or butyric acid concentration range is from 0.2% to 5.0%. The highest concentration at which colonies still form represents the acid tolerance of the microorganism. An alternative acid tolerance test method is to overlay the non-acid support with a solution containing a specified concentration of the acid.

By dividing the highest acid concentration that a mutant microorganism is capable of growing by the highest acid concentration where non-mutant microorganism growth is noted, the relative acid tolerance of the mutant microorganism can be calculated.

For example, if mutants of a strain of *C. acetobutylicum* are isolated using the methods of this invention that display an acetic acid tolerance of at least 4%, while the parent strain has an acetic acid tolerance of 2%, the relative acid tolerance of the mutants would be 200% of the non-mutant parent strain.

In some embodiments, the relative acid tolerance of mutant microorganisms of the present invention include microorganisms with at least 125% tolerance compared to the acid tolerance for the corresponding non-mutant microorganism. In other embodiments, selected mutant microorganisms exhibit at least 150%, 200%, 250%, 300%, 400%, 500%, 600%, 700%, 800%, 900%, 1,000%, 2,000%, 3,000%, 4,000%, 5,000%, 6,000%, 7,000%, 8,000%, 9,000%, 10,000%, 11,000%, 12,000%, 13,000%, 14,000%, or 15,000% acid tolerance compared to the acid tolerance for the corresponding non-mutant microorganism. If the parent microorganism is unavailable, then the comparison can be performed using a standard species or strain. For example, with *C. acetobutylicum*, a standard strain is ATCC 824.

In some embodiments, acid tolerance is an absolute value that is determined by measuring the growth ability of a mutant microorganism on a semi-solid or solid support containing a specified concentration of an acid. For example, mutants of *C. saccharobutylicum* produced using the methods of the invention may have an absolute tolerance to acetic acid or butyric acid of at least 0.8%, whereas the parent microorganism cannot grow above an acetic acid or butyric acid concentration of 0.40%. In some embodiments, mutants of *C. acetobutylicum* or *C. saccharobutylicum* exhibit tolerance to acetic acid or butyric acid of at least 0.2%, 0.40%, 0.60%, 0.80%, 1.00%, 1.20%, 1.40%, 1.60%, 1.80%, 2.00%, 2.20.0%, 2.40%, 2.60%, 2.80%, 3.00%, 3.5%, 4.00%, 5.00%, 6.00%, 7.00%, or 8.00%.

Solvent Tolerance

In some embodiments, solvent tolerant microorganisms are mutagenized and selected for increased solvent tolerance on solid support. In some embodiments, solvent tolerant mutants can be used for either solvent or organic acid production. For example, a solvent tolerant mutant of *C. acetobutylicum* can be cultured under conditions conducive for acetic and butyric acid production, or alternatively, under condition conducive to butanol production. In some embodiments of the present invention, solvent tolerance is a relative value that is measured by comparing the growth ability of a mutant microorganism on a semi-solid or solid support to the growth ability of the non-mutant parent microorganism on the same semi-solid or solid support. Typically, the semi-solid or solid support comprises a growth media and a specified concentration of a solvent that is usually measured on a volume to volume (v/v) basis. Generally, multiple containers, usually petri dishes, are filled with semi-solid or solid support representing a range of solvent concentration. For example, a useful support for testing butanol tolerance of *C. acetobutylicum*, is agar containing Reinforced *Clostridium* Medium (RCM) and a useful butanol concentration range is from 0.8% to 5.0%. The highest concentration at which colonies still form represents the solvent tolerance of the microorganism. An alternative solvent tolerance test method is to overlay the non-solvent support with a solution containing a specified concentration of a solvent. Another alternative solvent tolerance test method is to determine survival following exposure to butanol.

By dividing the highest solvent concentration that a mutant microorganism is capable of growing by the highest solvent concentration where non-mutant microorganism growth is noted, the relative solvent tolerance of the mutant microorganism can be calculated.

As an example of the relative solvent tolerance calculation, mutants of *C. saccharobutylicum* strain Co-7449 were isolated using the methods of this invention that display a butanol tolerance of at least 5%. Strain Co-7449, on the other hand, has a butanol tolerance of approximately 2.1%. Therefore, the relative solvent tolerance of the mutants is at least 225% of the non-mutant parent strain.

In some embodiments, the relative solvent tolerance of mutant microorganisms of the present invention include microorganisms with at least 125% tolerance compared to the solvent tolerance for the corresponding non-mutant microorganism. In other embodiments, selected mutant microorganisms exhibit at least 150%, 200%, 250%, 300%, 400%, 500%, 600%, 700%, 800%, 900%, 1,000%, 2,000%, 3,000%, 4,000%, 5,000%, 6,000%, 7,000%, 8,000%, 9,000%, 10,000%, 11,000%, 12,000%, 13,000%, 14,000%, or 15,000% solvent tolerance compared to the solvent tolerance for the corresponding non-mutant microorganism. If the parent microorganism is unavailable, then the comparison can be performed using a standard species or strain. For example, with *C. acetobutylicum*, a standard strain is ATCC 824.

In some embodiments, solvent tolerance is an absolute value that is determined by measuring the growth ability of a mutant microorganism on a semi-solid or solid support containing a specified concentration of a solvent. For example, mutants of *C. saccharobutylicum* strain Co-7449 produced using the methods of the invention have an absolute tolerance to butanol of at least 5%, whereas the parent microorganism cannot grow above a butanol concentration of 2.1%. In some embodiments, mutants of *C. acetobutylicum* or *C. saccharobutylicum* exhibit butanol tolerance of at least 2.0%, 2.5%, 3.0%, 3.5%, 4.0%, 5.0%, 6.0%, 7.0%, 8.0%, 9.0%, 10.0%, 12.5%, 15.0%, 20%, or 25%. In other embodiments, mutants of *C. acetobutylicum* or *C. saccharobutylicum* exhibit tolerance to total ABE solvent concentrations of at least 2.0%, 2.2%, 2.4%, 2.5%, 2.6%, 2.8%, 3.0%, 3.2%, 3.4%, 3.6%, 4.0%, 5.0%, 7.0%, 10%, 12%, or 15%.

Fermentation Media

Fermentation media for the production of products must contain suitable carbon-based substrates. These substrates are converted enzymatically to intermediate compounds used by the biochemical, metabolic, synthetic, and fermentative pathways to produce products. As used herein, the term "carbon-based substrate" refers to material containing at least one carbon atom which can be enzymatically converted into an intermediate for subsequent conversion into the desired carbon target. Exemplary carbon-based substrates include, but are not limited to biomass, starches, dextrins, sugars, or hydrolysates of these materials.

As used herein, "biomass" refers to cellulose- and/or starch-containing raw materials, including but not limited to wood chips, corn stover, rice, grasses, forages, perrie-grass, potatoes, tubers, roots, whole ground corn, grape pomace, cobs, grains, wheat, barley, rye, milo, brans, cereals, sugar-containing raw materials (e.g., molasses, fruit materials, sugar cane, or sugar beets), wood, and plant residues.

As used herein, "starch" refers to any starch-containing materials. In particular, the term refers to various plant-based materials, including but not limited to wheat, barley, potato, sweet potato, tapioca, corn, maize, cassava, milo, rye, and brans. In general, the term refers to any material comprised of the complex polysaccharide carbohydrates of plants, comprised of amylose, and amylopectin, with the formula $(C_6H_{10}O_5)_x$, wherein "x" can be any number.

As used herein, "cellulose" refers to any cellulose-containing materials. In particular, the term refers to the polymer of glucose (or "cellobiose"), with the formula $(C_6H_{10}O_5)_x$, wherein "x" can be any number. Cellulose is the chief constituent of plant cell walls and is among the most abundant organic substances in nature. While there is a β-glucoside linkage in cellulose, there is an α-glucoside linkage in starch. In combination with lignin, cellulose forms "lignocellulose."

As used herein, "hemicellulose" refers to any hemicellulose-containing materials. In particular, the term refers to heteropolymers with xylosyl-, glucosyl-, galactosyl-, arabinosyl- or mannosyl-residues.

Suitable substrates include, but are not limited to processed materials that contain constituents which can be converted into sugars (e.g. cellulosic biomass, glycogen, starch, and various forms thereof, such as corn starch, wheat starch, corn solids, and wheat solids). Other suitable substrates include, but are not limited to mono- and di-saccharides, sugars (raw or processed), molasses, syrups and juices from agricultural materials (such as sweet sorghum juice), juice concentrates, corn syrup, and similar. Various starches are commercially available.

Fermentable sugars can be obtained from a wide variety of sources, including lignocellulosic material. Lignocellulose material can be obtained from lignocellulosic waste products (e.g., plant residues and waste paper). Examples of suitable plant residues include but are not limited to any plant material such as stems, leaves, hull, husks, cobs and the like, as well as corn stover, bagasses, wood, wood chips, wood pulp and sawdust. Examples of waste paper include but are not limited to discarded paper of any type (e.g., photocopy paper, computer printer paper, notebook paper, notepad paper, typewriter paper, and the like), as well as newspapers, magazines, cardboard, and paper-based packaging material.

As known in the art, in addition to an appropriate carbon source, fermentation media must contain suitable nitrogen source(s), mineral salts, cofactors, buffers, and other components suitable for the growth of the cultures and promotion of the enzymatic pathway necessary for the production of the desire target (e.g., butanol). In some embodiments, salts and/or vitamin B12 or precursors thereof find use in the present invention.

The nitrogen source may be any suitable nitrogen source, including but not limited to, ammonium salts or yeast extract. Phosphorus may be present in the medium in the form of phosphate salts, such as sodium and potassium phosphates. Sulfur may be present in the medium in the form of sulfate salts, such as sodium or ammonium sulfates. Additional salts include, but are not limited to, magnesium sulfate, manganese sulfate, iron sulfate, magnesium chloride, calcium chloride, manganese chloride, ferric chloride, ferrous chloride, zinc chloride, cupric chloride, cobalt chloride, and sodium molybdate. The growth medium may also contain vitamins such as thiamine hydrochloride, biotin, and para-aminobenzoic acid (PABA).

Culture Conditions

Optimal culture conditions for the various industrially important microorganisms are known in the art. As required, the culture conditions may be anaerobic, microaerotolerant, or aerobic conditions. As is readily understood by the skilled person, anaerobic conditions are those that are essentially devoid of oxygen, aerobic conditions are those that contain oxygen dissolved in the media such that an aerobic culture would not be able to discern a difference in oxygen transfer with the additional dissolved oxygen, and microaerotolerant conditions are those where some dissolved oxygen is present at a level below that found in air and frequently below the detection limit of standard dissolved oxygen probes, e.g., less than 1 ppm. The cultures can be agitated or left undisturbed. Typically, the pH of the media changes over time as the microorganisms grow in number, consume feedstock and excrete organic acids. The pH of the media can be modulated by the addition of buffering compounds to the initial fermentation media in the bioreactor or by the active addition of acid or base to the growing culture to keep the pH in a desired range.

Growth of the culture may be monitored by measuring the optical density, typically at a wavelength of 600 nm.

For converting sugars to ethanol using *S. cerevisiae*, generally, the temperature is between about 25° C. and 35° C. Useful pH ranges for the conversion medium are provided between 4.0 and 6.0, between 4.5 and 6.0, and between pH 5.5 and 5.8. The culture is grown under anaerobic conditions without agitation.

ABE fermentations by *C. acetobutylicum* are typically conducted under anaerobic conditions at a temperature in the range of about 25° C. and 40° C. Historically, suspension cultures did not use agitators, but relied on evolved or sparged gas to mix the contents of the bioreactors. Cultures, however, can be agitated to ensure more uniform mixing of the contents of the bioreactor. For immobilized cultures, the bioreactors will be run without agitation in a fixed bed (plug flow) or fluidized (well-mixed) mode. Thermophillic bacterial fermentations can reach temperatures in the range of about 50° C. to 80° C. In some embodiments, the temperature range is about 55° to 70° C. In some embodiments, the temperature range is about 60° C. to 65° C. For example, *Clostridium* species such as *C. thermocellum* or *C. thermohydrosulfuricum* may be grown at about 60° C. to 65° C.

Semi-Solid and Solid Support

For the production of fermentative, metabolic, respiratory or synthetic products, the microorganisms of this invention are grown immobilized to semi-solid or solid supports. Various types of semi-solid and/or solid support materials may be used. Useful support material has a high surface area to volume ratio such that a large amount of active, productive cells can accumulate in the bioreactor.

Non-limiting examples include solid agar, porous materials such as bone char, synthetic polymers, natural polymers, inorganic materials, or organic materials. Natural polymers include organic materials such as cellulose, lignocellulose, hemicellulose, and starch. Organic materials include feedstock such as plant residue and paper. It is understood that composites of two or more materials may also be used such as mixtures of synthetic polymer with natural plant polymer.

Examples of semi-solid media include alginate, κ-carrageenan and chitosan, polyacrylamide, polyacrylamide-hydrazide, agarose, polypropylene, polyethylene glycol, dimethyl acrylate, polystyrene divinyl benzene, polyvinyl benzene, polyvinyl alcohol, epoxy carrier, cellulose, cellulose acetate, photocrosslinkable resin, prepolymers, urethane, and gelatin.

Examples of solid support include cork, clay, resin, sand, porous alumina beads, porous brick, porous silica, celite, wood chips or activated charcoal.

The suitable inorganic solid support materials are general inorganic materials with available surface hydroxy or oxide groups. Such materials can be classified in terms of chemical composition as siliceous or nonsiliceous metal oxides. Siliceous supports include, among others, glass, colloidal silica, wollastonite, cordierite, dried silica gel, bentonite, and the like. Representative nonsiliceous metal oxides include alumina, hydroxy apatite, and nickel oxide.

Methods of Immobilization on a Solid Support

Immobilization of the microorganism, from spores or vegetative cells, can be by any known means. Generally, microorganisms can be immobilized to a semi-solid or solid support by three different mechanisms. The first, entrapment or inclusion in the support, is achieved by polymerizing or solidifying a spore or vegetative cell containing solution. Useful polymerizable or solidifyable solutions include alginate, κ-carrageenan, chitosan, polyacrylamide, polyacrylamide-hydrazide, agarose, polypropylene, polyethylene glycol, dimethyl acrylate, polystyrene divinyle benzene, polyvinyl benzene, polyvinyl alcohol, epoxy carrier, cellulose, cellulose acetate, photocrosslinkable resin, prepolymers, urethane, and gelatin.

The second immobilization method is by adsorption onto a support. Useful supports include e.g. bone char, cork, clay, resin, sand porous alumina beads, porous brick, porous silica, celite, or wood chips. The microorganisms colonize the substrate and form a biofilm. The third immobilization method is through the covalent coupling of the microorganisms to a support using chemically agents like glutaraldehyde, o-dianisidine (U.S. Pat. No. 3,983,000), polymeric isocyanates (U.S. Pat. No. 4,071,409), silanes (U.S. Pat. Nos. 3,519,538 and 3,652,761), hydroxyethyl acrylate, transition metal-activated supports, cyanuric chloride, sodium periodate, toluene, and the like. See also U.S. Pat. Nos. 3,930,951 and 3,933,589.

In one embodiment, immobilized spores, such as those of *C. acetobutylicum*, are activated by thermal shock and then incubated under appropriate conditions in a growth medium whereby vegetative growth ensues. These cells remain enclosed in or on the solid support. After the microorganisms reach a suitable density and physiological state, culture conditions can be changed for acid and/or solvent production. If the immobilized cells lose solvent production, they can be reactivated by first allowing the cells to sporulate before repeating the thermal shock and culture sequence.

Vegetative cells can be immobilized in different phases of their growth. For microorganisms that display a biphasic culture, such as *C. acetobutylicum* with its acidogenic and solventogenic phases, cells can be immobilized after they enter the desired culture phase in order to maximize production of the desired products, where in the case of *C. acetobutylicum* it is the organic acids acetic acid and butyric acid in the acidogenic phase and the solvents acetone, butanol and ethanol in the solventogenic phase. Alternatively, biphasic cells can be immobilized in the acidogenic phase and then adapted for solvent production.

In some embodiments, microorganisms to be immobilized in a bioreactor are introduced by way of a cell suspension. Generally, these microorganisms are dispersed in the media as single cells or small aggregates of cells. In other embodiments, the microorganisms are introduced into the bioreactor through the use of suspended particles that is colonized by the microorganisms. These suspended particles can be absorbed onto the solid support and frequently are of sufficiently small size that they can enter and become immobilized in the pore structures of the solid support comprising the packed bed. Typically, regardless of the suspended particle size, microorganisms can be transferred by contact with the solid support comprising the packed bed through contact. The biofilm on the introduced particles can transfer to and colonize these new surfaces. In some embodiments, the desired characteristics of the microorganisms can only be maintained by culturing on a solid support, thereby necessitating the use of small colonized particle suspensions for seeding the solid support of bioreactors.

Bioreactors

One or more bioreactors may be used in this invention. When multiple bioreactors are used they can be arranged in series and/or in parallel. The advantages of multiple bioreactors over one large bioreactor include lower fabrication and installation costs, ease of scale-up production, and greater production flexibility. For example individual bioreactors may be taken off-line for maintenance, cleaning, sterilization, and the like without appreciably impacting the production schedule.

It is understood that bioreactors arranged in parallel or series may comprise one or more types of fermentation processes. For example, in a series arrangement, the first bioreactor may comprise batch fermentation while the second bioreactor, may comprise continuous fermentation.

In another embodiment, in a series arrangement each bioreactor can have a different species, strain, or mix of species or strains of microorganisms compared to other bioreactors in the series. Similarly, in another embodiment of the invention, illustrated in FIG. 8, in a series arrangement the first bioreactor has a suspension culture while the second bioreactor has immobilized cells. In this arrangement, media is introduced into the suspension culture bioreactor and the fermentation effluent is removed and fed to the immobilized cells in the second bioreactor, along with additional media. The immobilized cells are mutants that exhibit increased product tolerance and can further utilize substrate in the media, creating a higher concentration of product. The fermentation effluent is then removed and sent to separation and recovery.

In another embodiment of the invention, a fermentor may be arranged in series such that effluent from the fermentor is introduced into multiple parallel fermentors at once. In some embodiments, effluent can be recycled after the harvesting of acids and/or solvents and used to make the initial fermentation media or a feed stream for future fermentations, thereby allowing maximum utilization of unassimilated and recovered nutrients and minerals. In some embodiments, product is isolated from the effluent and the product reduced effluent is then used as a feedstock for the next fermentor in the series. Various types of extractions techniques including gas stripping, adsorbents, pervaporation, perstraction, and distillation can be used.

The order of bioreactors in a series can be adjusted to prevent or remove blockage due to excessive biomass growth. For example, when the first fermentor in a series reaches a high level of biomass it can be placed second in the series to instead now receive effluent with high product concentration or reduced nutrient levels that may inhibit further biomass production. The timely shifting of the order of fermentors may prevent biomass overgrowth and blockage of the fermentor if it is a packed or fluidized bed bioreactor.

In a continuous process, it is possible to obtain a higher productivity than in batch or fed-batch processes since the cell concentration and the effluent flow rate can be varied independently of each other. In a continuous fermentation, volumetric productivity is calculated by multiplying the product concentration (herein, interchangeably called the "titer") times the nutrient dilution rate (i.e. the rate of changeover of the volume of the bioreactor, or the inverse of the bioreactor residence time). The maximum achievable dilution rate is determined by the concentration of biomass that one can stably maintain in the bioreactor. At a constant dilution rate (i.e. nutrient consumption rate), as one increases the fermentation titer that can be maintained, the productivity is proportionately increased. Immobilized cell bioreactors allow higher concentrations of productive biomass to accumulate and therefore, the bioreactors can be run at high dilution rates, resulting in a significant improvement in volumetric productivity relative to cultures of suspended cells. Bioreactors for the continuous fermentation of *C. acetobutylicum* are also known in the art. (U.S. Pat. Nos. 4,424,275, and 4,568,643.) Since a high density, steady state culture can be maintained through continuous culturing, with the attendant removal of product containing fermentation broth, smaller capacity bioreactors can be used.

Conventional bioreactors and methods for culturing microorganisms to produce target products are known and are contemplated for use with the present invention methods and compositions. For example, fermentors for use in the batch fermentation of *C. acetobutylicum* are well known in the art. (Beesch, S. C. Acetone-butanol fermentation of sugars. Eng. Proc. Dev. 44:1677-1682, 1952; Beesch, S. C. Acetone-butanol fermentation of starches. Appl. Microbiol. 1:85-96, 1953; Killeffer, D. H. Butanol and acetone from corn. A description of the fermentation process. Ind. Eng. Chem. 19:46-50, 1927; MuCutchan W. N., and Hickey, R. J. The butanol-acetone fermentations. Ind. Ferment. 1:347-388, 1954.) Historically, fermentors used for butanol production have capacities of 50,000 to 200,000 gallons and are frequently without mechanical agitation systems. Fermentor capacities contemplated for use with the invention include fermentors with at least 100 L, 1000 L, 10,000 L, 50,000 L, 100,000 L, 250,000 L, or 500,000 L capacity.

Mixing of the fermentor contents can be achieved through the sparging of sterile gas, e.g. carbon dioxide or $N_2$, which may also serve to prevent contamination of the culture through the maintenance of positive pressure within the fermentor. The evolved gas ($CO_2$, $H_2$) from the fermentation may also be utilized in a gas lift type reactor to maintain anaerobic, pressurized, well mixed conditions. Other techniques of mixing culture contents include the use of agitators or the recirculation of fermentation broth, particularly broth returned to the fermentor after the removal of a fermentation product. In some embodiments, the contents of the fermentor are not mixed, but may rely on the production and movement of evolved gases to mix contents.

Immobilized Cell Bioreactor

In some embodiments of the invention, immobilized microorganisms are cultured in packed bed bioreactors, also known as plug-flow bioreactors. In other embodiments, the microorganisms are cultured in expanded (fluidized) bed bioreactors. In still further embodiments, the microorganisms are cultured in bioreactors that are designed to operate in dual mode, i.e., the bioreactors are capable of operating in either packed bed or expanded (fluidized) bed mode. FIGS. 19A and 19B. Immobilized cell bioreactors use relatively small sized solid supports that provide a large surface area relative to the volume of the particles, allowing for the microorganisms immobilized on the particles to process large volumes of fluid. In packed bed bioreactors, cells are immobilized on or in semi-solid or solid particles that because of particle size, mechanical restraint and/or low fluid flow rates do not cause or allow for appreciable axial movement of the supporting material. Packed bed reactors are simple to construct and operate but can suffer from blockages, poor nutrient transfer and poor pH control.

In contrast, expanded (fluidized) bed reactors use semi-solid or solid support that is not substantially restrained mechanically so that with sufficient fluid flow, usually an upward-flowing stream, the particles become suspended in the stream or "fluidized", i.e. act as if they are part of the fluid stream. Fluid drag on the particle is the primary suspension mechanism, but buoyancy forces can also contribute to the suspension of the particles. Typically, the bioreactors use vertical fluid motion to suspend the particles, but other fluid motion is possible including fluid flow at a direction perpendicular to the vertical axis of the bioreactor. The fluid velocity should be sufficient to suspend the particles, but not large enough to carry them out of the vessel. The expansion of the bed allows the solid particles to move around the bioreactor, causing the fluid within the bioreactor to thoroughly mix. The magnitude of mixing depends on the extent of particle fluidization achieved in the bioreactor. Expanded bed bioreactors require relatively larger amounts of energy to operate compared to packed beds because of the volume of fluid that must be circulated to keep the particles suspended.

The dual mode, packed bed-expanded bed bioreactors of the invention allow for the option of conducting fermentations in either mode for the course of a whole fermentation run. Alternately, the fermentation can alternate between modes during the course of a single fermentation. Dual mode bioreactors can have reduced energy usage compared to conventional expanded (fluidized) bed bioreactors because fluidization with its requisite increased energy requirement need only be performed, for example, at relatively high cell densities, high product concentrations, or when pH or nutrient inhomogeneities develop that can be corrected through increased mixing of the bioreactor contents.

The following illustrates one embodiment of a dual mode bioreactor that operates with a vertical fluid flow. The solid support of the bioreactor is seeded with microorganisms in the packed bed mode and then maintained for a period of time in batch mode with no fluid flow. As the microorganisms start to colonize the semi-solid or solid support and increase in density, a low fluid flow rate is initiated to provide additional nourishment and/or to control pH. The flow rate is then increased as required to accommodate increased cell density. At a certain point, the increased fluid flow will cause the packed column to start to expand or "fluidize" into an area of the bioreactor termed the "expanded bed zone." FIG. 19B. The minimum fluid velocity, $U_{mf}$, required for bed expansion depends on numerous considerations including the bioreactor configuration and its attendant fluid dynamics, the specific particle size distribution of the semi-solid or solid support, and the void volume of the packed bed as further explained in the Examples section using a particular embodiment to illustrate the general engineering concept. With further increases in fluid velocity, the packed bed will continue to expand. As can be appreciated, energy usage is initially very low and will ramp up as fluid flow commences and later increases to accommodate the biological needs of the culture. Fluidization and hence, maximum energy consumption, need only occur in a dual mode bioreactor at the point in time when the cell density requires such mixing to further increase productivity, decrease pH or substrate inhomogeneity, or otherwise rectify or manage other culture conditions brought on by the increased cell density.

Another illustration of an embodiment of the operation of a vertical fluid flow dual mode bioreactor is as follows. The solid support of the bioreactor is seeded with microorganisms during packed bed mode through the continuous perfusion of the packed bed with smaller semi-solid or solid particles that are colonized with microorganisms. The smaller particles can enter the pore structure of the support material and lodge there, or through collisions between the smaller particles and the solid support, microorganisms may transfer to the support material. After 24 hours the perfusion of the support with the smaller particles with attached microorganisms is terminated and perfusion with a nutrient solution commences. A low flow rate is used that is increased over time as needed to provide adequate nutrients, but is never increased over the course of the fermentation run to the point that the $U_{mf}$ is reached.

Numerous methods of fermentor inoculation are possible including back flushing from the top of fermentor to load the bed from the top. Other ways include the addition of a liquid culture or impregnated solid support through a port located along the reactor's wall. Reactor effluent may also be used to inoculate an additional reactor and in this case any residual fermentable materials may be converted in the secondary reactor, increasing yield/recovery.

In a similar manner, support material may be added to the column/reactor through bottom, top, or side loading to replenish support material that becomes degraded or lost from the bioreactor.

To keep the fluidized support material contained within the bioreactor, a particle disengagement zone is place above the bed expansion zone. The disengagement zone has a means for separating the fluidized particles from the fluid and thereby retaining the particles within the bioreactor. In some embodiments, the means for separating the particles from the fluid comprises a means for slowing the velocity of the fluid. Typically, this is accomplished by increasing the cross sectional area of the bioreactor. As the fluid velocity slows, the particles start to settle out of the fluid. The top section of the particle disengagement zone is free of particles. An outlet can be located at this top portion to remove effluent. Other means to retain particles include filters or screens located within the bioreactor. Support material can be removed and recovered from the effluent stream through the use of settling tanks, centrifuges, hydrocyclones, all types of filters (e.g., rotary drum), filter aids, dryers, or distillation apparatus.

As the previous example illustrates, a dual mode bioreactor of the invention comprises an inlet coupled to a packed bed zone coupled to a bed expansion zone coupled to a particle disengagement zone that has an outlet. FIG. 19B. In some embodiments, the bioreactor of this design is capable of continuous fermentations of at least 100, 250, 500, 750, 1,000, 1250, 1,500, 2,000, 2,250, 2,500, 3,000 hours, 4,000, 5,000 or 6,000 hours. A dual mode packed bed-expanded bed bioreactor may further comprise a column expansion zone. FIG. 19B This zone is coupled to the downstream end of the bed expansion zone and it is coupled to the upstream end of the particle disengagement zone. The column expansion zone comprises a sloping surface to return particles that have fallen out of the fluid stream to the expanded bed zone. The angle of the slope is at least 15°, 20°, 30°, 40°, 45°, 50°, 55°, 60°, 70°, or 80° when measured from the horizontal. The column expansion zone further functions as a particle disengagement zone since the top portion of the zone has a wider cross-sectional diameter, and hence will have a slower vertical fluid velocity. The column expansion zone is optional as a particle disengagement zone can be used that comprises a sloped angle for the return of the support material to the expanded bed zone.

A dual mode packed bed-fluidized bed bioreactor may further comprise a gas-liquid separation zone. FIG. 19B This zone is coupled to the down stream end of the particle disengagement zone. The gas-liquid zone allows for the separation of evolved or introduced gases from the fermentation broth and may be required with cultures that actively produce gases such as $CO_2$, $H_2$, or methane or when the cultures are sparged. An alternative to the gas-liquid zone is the placement of a holding tank downstream of the bioreactor outlet. The effluent will usually enter and exit the tank from low points in the tank, while a head space is provide to trap any gas that may be dissolved in the effluent or carried as bubbles or foam out of the bioreactor. Usually, a vent, frequently coupled to a condenser, filter and/or scrubber to control odors, is placed at a high point in the tank to allow accumulated gas to exit the system. Depending on factors like flow rate, feed stock, and production of insoluble debris, the holding tank may comprise a settling area, wherein particulate matter can settle out and be periodically removed. With the anticipated high product titers to be achieved with this invention, certain products like butanol may reach a concentration point wherein the product will phase separate from the fermentation effluent. The holding tank can be further designed to comprise an area to facilitate the separation of the product from the effluent by phase separation and also harvest of the product by decantation or drawing off accumulated product that is less dense than the effluent.

The holding tank noted above may also serve as a in situ product extraction location in which any manner of product recovery techniques—including but not limited to gas stripping, pervaporation, vacuum recovery, or liquid-liquid extraction, may be used to assist the recovery of product from the process.

A dual mode bioreactor may further comprise an inlet distribution zone. FIG. 19B. The inlet distribution zone is coupled to the upstream end of the packed bed zone. The inlet distribution zone distributes fluid uniform across the packed bed to prevent inhomogenieties in feed stock distribution or the creation of pH gradients within the bed. Generally, the pressure drop of the bioreactor across the inlet distribution zone is limited to no more than 30% of the total pressure drop across the length of the bioreactor. In some embodiments, the pressure drop is less than 30%, 25%, 20%, 15%, 10%, or 5% of the total system pressure.

Typically, at least one of the column expansion zone, the particle disengagement zone, or the gas-liquid separation zone has a diameter that is larger than the diameter of the packed bed zone.

The bioreactors of the invention may also be alternately perfused from the top of the bioreactor down through the packed bed in the direction opposite the usually fluid flow. Alternate feeding directions may prevent or reduce the development of flow restrictions and thereby extend the life of the packed bed and hence allow for prolonged continuous fermentation runs.

Support material is generally available in different particle size classifications. For example, bonechar is available in mesh sizes of 5×8, 10×28, and 20×60. Within each particle classification there is a range of particle size. For example, with 5×8 bonechar the particles range from 3000-5000 μm in size. With any particular particle size range, there is a minimum fluid velocity, $U_{mf}$, required for fluidization of the largest particles found within the particle size range. A dual mode bioreactor is typically designed to be of sufficient overall height so as to be able to retain within the bioreactor the smallest sized particles found within the distribution range when it is operated at the $U_{mf}$. Generally, the minimum sufficient bioreactor height is calculated by determining the ratio of the total height of the expanded bed (H) to the height of the packed bed ($H_p$), where H is equal to height of $H_p$ plus the bed expansion zone. A dual mode bioreactor should have a H:$H_p$ ratio of at least 1.0 and preferably a ratio of at least 1.05, 1.10, 1.15, 1.20, 1.25, 1.30, 1.35, 1.40, 1.45, 1.50, 1.55, 1.60, 1.70, 1.80, 1.90 or 2.00.

The Experimental section details a general method as applied to bonechar for deriving the ratio of H:$H_p$ for a particular semi-solid or solid support material of a given particle size distribution range.

The packed bed height can be calculated as the height of the packed bed at any point during a fermentation run, including a time point at least a quarter, half, or three-quarters through the run, or at the end of the run. This calculation takes into account an increase over time of the size of individual particles that can occur with the growth of exterior biofilm. The packed bed can also increase in size due to the accumulation of insoluble debris.

The dual mode bioreactors of the invention can further comprise means for controlling pH, controlling Redox, introducing antifoam, and portholes for visualizing the contents of the bioreactor and for introducing probes for detecting or measuring various constituents of the fermentation broth including one or more fermentation products. Additionally, temperature probes, pressure probes and dissolved oxygen or other dissolved gas probes can be introduced through portholes. Alternatively, the measurements can be accomplished by having probes placed in-line of the effluent stream exiting the bioreactor. Sampling ports may also be present for the automatic or manual procurement of physical samples. Additionally, the evolved or introduced gases can be sampled from a port in the gas-liquid separation zone or in-line of an off gas processing system. The bioreactors can be jacketed for temperature control and for in-place sterilization. Optionally, the bioreactors can be of a modular design that allows for large scale access to the interior of the bioreactor or allows for changes in the height of one or more of the packed bed zone, expanded bed zone, column expansion zone, particle disengagement zone, or gas-liquid separation zone.

The dual mode bioreactor of the instant invention can be run primarily in packed bed mode with periodic boosts in fluid velocity to achieve expansion of the column into the column expansion zone or to fluidize the packed bed. This can be done prophylactically at scheduled intervals to prevent pressure build up and restriction or clogging of fluid flow. In some embodiments, the bioreactor is run principally in packed bed mode, but is switched to expanded bed mode at a frequency of every hour, 2 hours, 4 hours, 6 hours, 8 hours, 12 hours, 18 hours, 24 hours, 2 days, 4 days, 6 days, 8 days, 10 days, 20 days, or combinations thereof. It can also be done when the fluid pressure increases beyond a predetermined operating point.

Upon reversion to a lower fluid velocity the particles will settle in a loser configuration that will allow for the same or greater fluid flow rates than before the flow rate boost, but with a reduced pressure drop. After each periodic flow rate boost in expanded bed mode, the flow rate in packed bed mode may be set to ratchet upwards over time, for example, with an initial flow rate of 100 ml/min, after the first boost the flow rate may be set to 105 ml/min, the next flow rate after a boost a 110 ml/min and so on. Such a ratcheting increase may prevent clogging or unacceptable pressure increases inside the bioreactor. The ability to periodically repack the bed through increased fluid velocity and then settling of the solid support and insoluble particles after the fluid velocity is lowered may afford a method to prevent clogging or fouling of the pack bed and conduct continuous fermentation runs in excess of 100, 250, 500, 750, 1,000, 1250, 1,500, 2,000, 2,250, 2,500, 3,000, 4,000, 5,000, 6,000, 7,000, or 8,000 hours. Depending upon the size and density of the insoluble particles that reside in the packed bed, the switch to expanded bed mode may allow the opportunity to flush these insoluble particles from the system. Using a holding tank in line with the bioreactor, the insoluble particles may settle out of the fermentor effluent. Alternatively, the insoluble particles can be filtered out, removed by centrifugation or through other suitable means.

The ability to periodically repack the bed though switching from packed bed to expanded bed run mode can also prevent or alleviate channeling in the bed matrix. Channeling can result in feed distribution and pH control inhomogeneities as the cells on solid support near channels are exposed to greater volumes of the feed stream compared to cells located on solid support away from the channels.

In some embodiments, the flow rate is boosted to initially adjust the interparticle spacing of the support material, prior to or immediately after seeding the bioreactor, thereby increasing the overall productivity or altering other parameters such as pressure drop across the bed. In some embodiments, a periodic increase or decreased in the flow rate cyclically expands and re-settles the support and organism material. In so doing, the void spacing between the support material can be adjusted.

Optionally, an anaerobic gas can be added the liquid media to enhance mixing, provide additional nutrients, or to maintain a positive pressure inside the bioreactor. The characteristics and behavior of a fluidized bed are dependent on both the solid and liquid properties. Where the product has a toxic or inhibitory effect on the microorganisms, gas stripping can be used to reduce the product concentration in the column fluid and thereby reduce or prevent product inhibition or toxicity.

The required particle size for use in the invention will vary depending upon application, bioreactor configuration and operation parameters. In some embodiments, the solid support is sized by sieving. In some embodiments, the particles are classified by the sieve number of the mesh that they can pass through. In some embodiments, the particles are sieved with a mesh that has a U.S. Sieve Number of 3½, 4, 5, 6, 7, 8, 10, 12, 14, 16, 18, 20, 25, 30, 35, 40, 45, 50, 60, or 70. In some embodiments, the particles are sieved at least twice, first using a mesh with larger openings followed by a mesh with smaller openings to yield particles within a defined particle size distribution range. In some embodiments, the particles are at least 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm in diameter. In some embodiments, the particles are less than 100 µm, 200 µm, 300 µm, 400 µm, 500 µm, 600 µm, 700 µm, 800 µm, 900 µm, 1000 µm, 1,100 µm, 1,200 µm, 1,300 µm, 1,400 µm, 1,500 µm, 1,600 µm, 1,700 µm, 1,800 µm, 1,900 µm, 2,000 µm in diameter. In further embodiments, at least 80%, 85%, 90%, 95%, or 100% of the particle have diameters that are in the range of 100-400 µm, 100-600 µm, 100-800 µm, 200-500 µm, 200-800 µm, 200-1000 µm, 400-800 µm, 400-1000 µm, 500-1000 µm, 600-1,200 µm, 800-1,400 µm, 1,000-1,500 µm, or 1,000-2000 µm. In some embodiments, the particle diameters are the equivalent diameters, a parameter that takes into account the irregular shapes of the individual particles.

Ideally, the semi-solid or solid support material should have a high surface area. This can be achieved through the use of small sized particles, particles with high porosity, or a combination thereof. In some embodiments, the surface area of the particles is at least 10 m$^2$/g, 25 m$^2$/g, 50 m$^2$/g, 75 m$^2$/g, 100 m$^2$/g, 125 m$^2$/g, 150 m$^2$/g, 175 m$^2$/g, 200 m$^2$/g, 225 m$^2$/g, 250 m$^2$/g, 275 m$^2$/g, 300 m$^2$/g, 325 m$^2$/g, 350 m$^2$/g, 375 m$^2$/g, 400 m$^2$/g, 425 m$^2$/g, 450 m$^2$/g, 500 m$^2$/g, 600 m$^2$/g, 700 m$^2$/g, 800 m$^2$/g, 900 m$^2$/g, 1000 m$^2$/g, or 2000 m$^2$/g. Additionally, the bulk density should be sufficiently high so that the smallest particles settle out of the fluid stream in the column expansion zone and/or particle disengagement zone and are thereby retained in the bioreactor. In some embodiments, the bulk density of the support is at least 0.3 g/cm$^3$, 0.4 g/cm$^3$, 0.5 g/cm$^3$, 0.6 g/cm$^3$, 0.7 g/cm$^3$, 0.8 g/cm$^3$, 0.9 g/cm$^3$, 1.0 g/cm$^3$, 1.1 g/cm$^3$, 1.2 g/cm$^3$, or 1.3 g/cm$^3$. The support material should have sufficient hardness to resist abrasion and thereby avoid appreciably dust formation when the support material touch or collide with each other. In some embodiments, the support has a ball-pan hardness number of at least 20, 40, 60, 80, 100, 120, 140, 160 or 200. The support material should also have sufficient tensile strength to resist shattering due to internal stresses caused by the growth of biofilms inside support material pores. In some embodiments, the support has a yield strength of at least 20 MaP, 40 MaP, 60 MaP, 80 MaP, 100 MaP, 120 MaP, 140 MaP, 160 MaP, 180 MaP, 200 MaP, 300 MaP, or 400 MaP.

Means for Harvesting Product

Numerous means are available for the isolation of products from fermentation broth including distillation, continuous extraction with solvents (U.S. Pat. Nos. 4,424,275 and 4,568,643), the use of fluorocarbons (U.S. Pat. No. 4,777,135), the use of absorbent material (U.S. Pat. No. 4,520,104), the use of a pervaporation membrane (U.S. Pat. No. 5,755,967), and the use of a stripping gas (U.S. patent application Ser. No. 10/945,551).

One embodiment of this invention uses a vapor compression distillation system. (U.S. Pat. Nos. 4,671,856, 4,769,113, 4,869,067, 4,902,197, 4,919,592, 4,978,429, 5,597,453, and 5,968,321.) Another embodiment utilizes a mechanical vapor recompression system to concentrate the solvents and utilize the enthalpy of the overhead stream to vaporize the feed mixture. In this embodiment, fermentation broth is sent directly to the MVR tower for solvent concentration. The overhead stream from the MVR system is compressed. A heat exchanger is used to transfer heat from the compressed overheads with the feed mixture. The solvent containing mixture is passed to subsequent distillation columns for separation. The bottoms from the MVR column contain the biomass and additional heavier compounds. The biomass is filtered by any manner of filtration and can be dried to recover additional water. The filtered stream contains a majority of water and fermentation media components. This stream is treated to remove undesirable components and can be recycled as process water. In an alternate configuration, for batch fermentations of C. acetobutylicum, the harvesting of products contained in the spent fermentation media first requires clarification by centrifugation, cross flow filtration or alternative means of filtration. The clarified fermentation broth is then sent to the distillation system wherein the clarified broth enters a heat exchanger and is preheated by heat transfer from outgoing distilled product and waste fluid. The preheated broth is degassed and fed to a plate-type evaporator/condenser which has counter-flow evaporating and condensing chambers formed alternately between stacked metal plates which are separated by gaskets. The media enters the evaporating chambers where it boils. Heated vapor leaving the evaporating chambers passes through a mesh that removes mist, and is then pressurized by a low pressure compressor. The pressurized vapor is delivered to the condenser chambers, where it condenses, partially or completely, as the distilled product, giving up heat to broth in the boiling chambers, and is then discharged from the system. Unvaporized broth containing dissolved solids can be recycled and used to supplement the feed mixture of a new fermentation run or it can be discharged from the system.

In some embodiments, with continuous cultures of C. acetobutylicum, the fermentation broth drawn is off the fermentor and centrifuged to concentrate cells and particulate matter. Alternately, the fermentation broth can be filtered, for example, by tangential flow filtration. The concentrated cells and particulate matter can be added back to the fermentor if desired to increase cell density or for further fermentation of the partially fermented substrate. Alternately, the clarified or filtered fermentation broth can be added back to the fermentor if it contains soluble fermentable substrate. When it is desired to harvest products from the media numerous strategies are available including storage of the clarified or filtered fermentation broth until a reasonable quantity is present to initiate a product separation run, such as distillation, or alternatively, a continuous feed of clarified or filtered fermentation broth can be sent to a separation system. In some embodiments, the fermentation broth can be processed directly without centrifugation or filtration.

Fermentation broth composed of certain butanol containing solvent mixtures may undergo spontaneous phase separation based on specific gravity. The use of a float level indicator can be used to assist in separating the butanol containing solvent layer from the remaining aqueous fraction.

Fermentation products can also be recovered by gas stripping or liquid extraction. In the case of gas stripping, the desired products or inhibitory compounds are desired to be removed from the fermentation broth. In the gas stripping approach, the removed product is recovered by means of a flash drum, vacuum extraction, or condensation method. The product is further purified or disposed in the case of inhibitory compounds. The biomass and other solid materials and precipitates formed must be removed or purged from the system at some point. This can be achieved by an intermittent or continuous purge stream. Biomass removal can be achieved by several means outlined previously. In the case of liquid extraction, biomass can be present in both the extracted stream or a purge stream. The liquid extractant stream is passed to additional recovery and purification operations.

EXAMPLES

Example 1

Preparation of P2+4% Xylose Agar Plates Containing 2.2-2.6% (v/v/) Butanol

To prepare 1 L of P2 medium, the following ingredients were weighed into a 1-L bottle: Bacto Yeast Extract (1.0 g), Ammonium Acetate (2.2 g), Potassium Phosphate, Dibasic ($K_2HPO_4$) (0.5 g), Potassium Phosphate, Monobasic ($KH_2PO_4$) (0.5 g). Distilled water (800 mL) was added to the mixture along with a stir bar. The ingredients were dissolved by mixing on a stir plate. The pH of the solution was adjusted to 7.2 with 5N NaOH. Agar (16 grams) was weighed out and added into the bottle. The volume was brought up to 915 ml with addition of the appropriate amount of distilled water. The bottle was covered, autoclaved for 30 minutes, and then placed on a stir plate. When the media was just cool to touch, the following was added to bring up the final volume of medium to 1 L: P2 Trace Elements (200×) (5 ml) and 50% (w/v) Xylose (80 ml for final concentration of 4% (w/v)).

1-L of 200× P2 trace elements was prepared by weighing out the following ingredients into a 1-L bottle: Magnesium Sulfate, Heptahydrate ($MgSO_4.7H_2O$) (40.0 g), Manganese Sulfate, Monohydrate ($MnSO_4.H_2O$) (2 g), Ferrous Sulfate, Heptahydrate ($FeSO_4.7H_2O$) (2 g), Para-amino-benzoic Acid (0.2 g), Thiamine HCl (0.2 g), Citric Acid (20 g), NaCl (2 g), D-Biotin (0.002 g). The final volume was brought up to 1-L with distilled water. The solution was filter sterilized using 0.2 micron filter, wrapped in aluminum foil, and stored at 4° C.

50% (w/v) xylose was prepared by heating 200 ml of distilled water to 50 deg C on a stir plate. 255 g of D-Xylose was added slowly to the heated water and stirred until all the Xylose has dissolved. The volume was brought up to 500 ml by adding distilled water. The solution was filter sterilize by passing through 0.2 micron filter.

Plates with 2.2-2.6% (v/v) butanol in 0.1% increments were prepared with 4.4-5.2 ml of butanol added in 0.2 ml increments, respectively, into each of five sterile 200 ml measuring cylinders. The volume in each measuring cylinder was brought up to 200 ml with P2+Xylose agar medium prepared as described, sealed using parafilm, and the cylinder was inverted to evenly mix the butanol with the P2+Xylose agar medium.

Agar medium was placed on a hot plate to keep the medium from solidifying during pouring. Plates (approximately 25-30 ml per plate) were poured using burner/torch to maintain a sterile environment from each measuring cylinder to get the appropriate concentration of Butanol in the plate 2.2-2.6% (v/v) in 0.1% increments. The plates were moved to the anaerobic hood when media has solidified and were individually parafilmed to prevent butanol loss. After 24 hrs in the anaerobic hood, the plates were ready to use.

Example 2

Double Disc Mutagenesis Assay for Isolation of Mutants with Increased Butanol Tolerance On the first day, a seed train of the strain to be mutagenized was started. The next day, appropriate number of 0.75×6 cm filter papers were cut. Half the number of filter papers were placed into a 50 ml tube containing 6 mg/ml MNNG. The other half of filter papers was placed into a 50 ml tube containing butanol. Tubes were moved into the anaerobic hood at least 4 hours before being used on plates.

The $OD_{600}$ of the seed train tubes was measured to determine which tube is closest to $OD_{600}$ of 1, and if needed, wait until the particular culture reached the $OD_{600}$ of 1. If all three cultures have grown above $OD_{600}$ 1, the appropriate dilution was made using YEM to obtain cultures of $OD_{600}$ 0.5. Cultures of $OD_{600}$ 0.5 reached $OD_{600}$ 1 within 0.5 to 1 hour.

200 µl of the above $OD_{600}$ 1, culture was plated on each RCM plate. A MNNG-soaked filter paper was placed horizontal to the one side of the plate (see FIG. 1). The plate was incubated for 1 hour. A butanol soaked filter paper was placed vertical (perpendicular) to the MNNG filter paper (see FIG. 8). Three control plates were prepared: a plate without butanol and MNNG, a plate without butanol, and a plate without MNNG.

The plates were incubated for 1 to 3 days. Growth of isolated colonies near the butanol filter paper (i.e. circled area in the FIG. 1) was evaluated. These colonies are assessed to determine their abilities to tolerate butanol compared to their parent strains.

Bacteria isolated in the circled area in FIG. 1 were re-exposed to this double gradient of MNNG and butanol to obtain multiple mutations. This may increase the ability of bacteria to tolerate butanol. A colony was isolated from the circled area after exposure to the double gradient twice.

Example 3

Isolation of Mutants with Increased Butanol Tolerance on Solid Media

*Clostridium saccharobutylicum* strain Co-7449 was grown in yeast extract medium (YEM) to an approximate $OD_{600}$ of 3 and was treated with a final concentration of 50 µg/ml N-methyl-N'-nitro-N-nitrosoguanidine (MNNG) for 15 minutes. Cells were twice washed with glucose-free YEM and plated on Reinforced *Clostridium* Medium (RCM) at $10^{-3}$ and $10^{-4}$ dilution to recover 3000-4000 colonies. The colonies were replica plated on to RCM plates containing 5% butanol. A total of 20 colonies were isolated in the butanol plates and re-streaked on RCM plates containing 5% butanol. The mutants display at least a two-fold higher tolerance for butanol when grown on a solid support compared to the parent Co-7449 strain that has a butanol tolerance of approximately 2.1% on solid support.

Butanol tolerance in suspension culture for select mutants was tested by taking colonies from the second set of 5% butanol RCM plates and using the mutants to inoculate flasks containing YEM media with or without 1.2% butanol. The colonies grew in YEM without butanol, but did not grow in YEM with 1.2% butanol added to the broth, illustrating that the mutant microorganisms are more solvent tolerant on solid support than when they are suspended in liquid media.

Samples removed from the YEM media without 1.2% butanol were plated on 5% butanol plates, but failed to grow. Maintenance of high butanol tolerant strains may require passage on solid support with continuous selective pressure of the solvent to retain the high tolerance.

Example 4

Butanol Tolerance Assay Protocol—Solid Vs. Liquid Media

Strains of *Clostridium* that were not adapted or selected for butanol tolerance were studied to see if they have greater solvent tolerance when cultured on solid support compared to suspension culture. On the first day, a seed train of a strain to be investigated was started in 5 ml cultures of P2+4% Xylose in the anaerobic hood. A 1-L volume of sterile P2 medium containing 4% Xylose and agar was prepared and place on hot plate. In a sterile environment, 4.4, 4.6, 4.8, 5.0, and 5.2 ml butanol was placed in 250 ml sterile measuring cylinders and made up to 200 ml with P2+4% Xylose Agar medium for 2.2, 2.3, 2.4, 2.5, and 2.6% (v/v) final butanol concentrations respectively. The solution was mixed well and plates were poured in a sterile environment. After the plates were solidified, they were transferred to the anaerobic hood and parafilmed immediately prior to storage overnight.

The next day, the $OD_{600}$ of the seed train tubes was measured. Tubes with $OD_{600}$ between 0.6-1.0 were picked and used to inoculate at 1:20 dilution into 10 ml of P2+4% Xylose tubes containing 0, 0.5, 1.0, 1.1, 1.2, 1.3, 1.4, 1.5, and 1.6% (v/v) butanol. Control tubes without inoculum were also prepared. Tubes were incubated in an anaerobic hood. Additionally, 200 µl of culture was plated on 0, 2.2, 2.3, 2.4, 2.5, and 2.6% (v/v) butanol plates.

Figure 3:
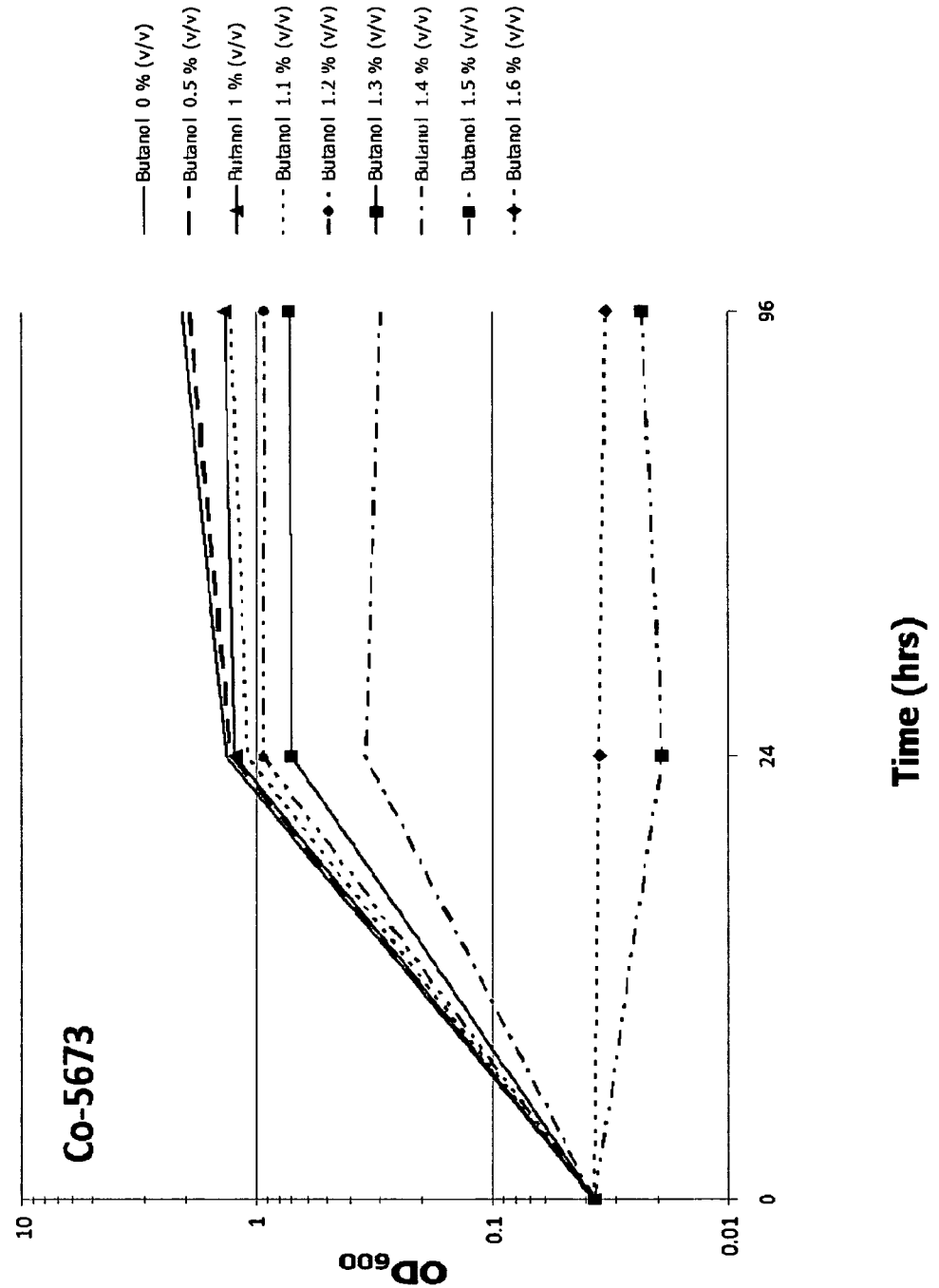
FIG. 3 is a graph showing Co-5673 growth over time in liquid media at each butanol concentration (0%-1.6% butanol).
Figure 4:
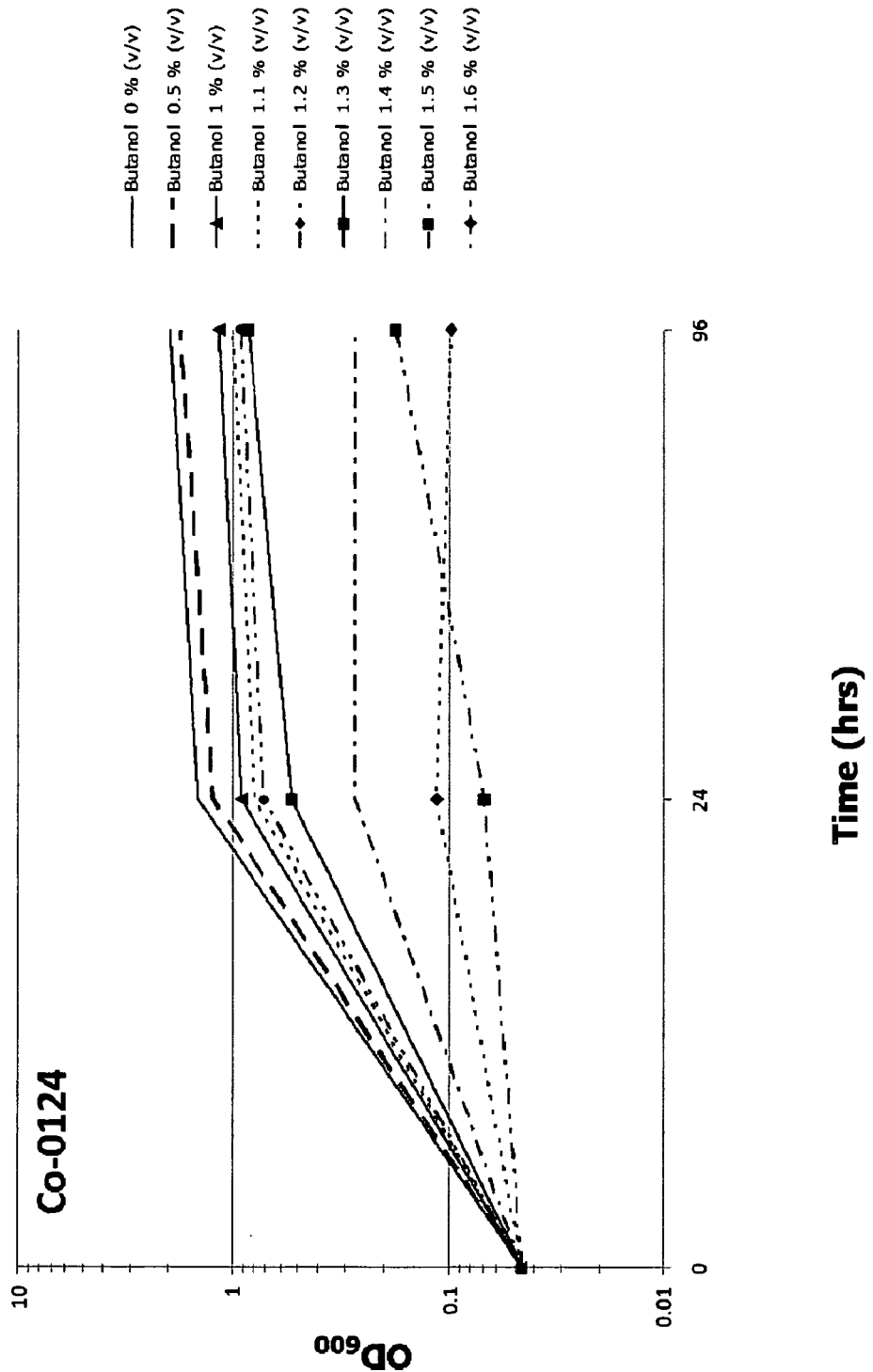
FIG. 4 is a graph showing Co-0124 growth over time in liquid media at each butanol concentration (0%-1.6% butanol).
Figure 5:
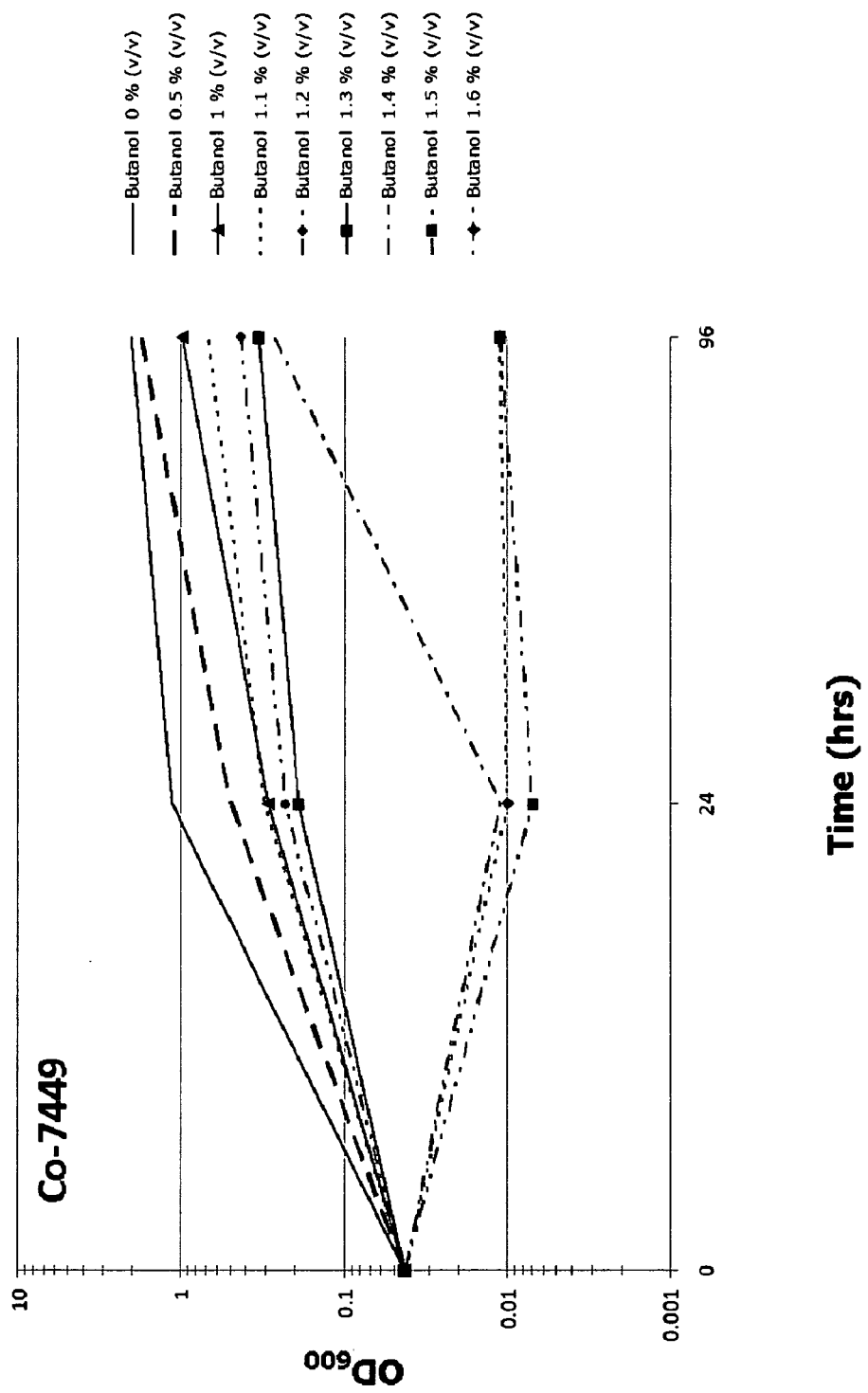
FIG. 5 is a graph showing Co-7449 growth over time in liquid media at each butanol concentration (0%-1.6% butanol).

After 1 day and 3-4 days, the $OD_{600}$ of liquid cultures was measured. Plates were examined for growth. For each strain and at each time point of the liquid cultures, $OD_{600}$ at each concentration of butanol relative to $(O)_{om}$ at 0% (v/v) butanol was plotted as $((OD_{600} \text{ at x \%})/(OD_{600} \text{ at } 0\%))*100$. FIG. 2A shows the $OD_{600}$ measurements taken at various time points (0 hr, 24 hr, 96 hr) for the various liquid cultures containing various butanol concentrations for the three *Clostridium* strains used. $OD_{600}$ at start (0 hr) was based on a 1:20 inoculation of the starter cultures. FIG. 2B shows $OD_{600}$ measurements of starter liquid cultures taken following 1:20 inoculations. FIG. 3 is a graphical representation of the data from FIG. 2A and shows Co-5673 growth over time in liquid media at each butanol concentration (0%-1.6% v/v). For Co-5673, $OD_{600}$ increased at the 24 and 96 hr time points up to 1.4% (v/v) butanol. FIG. 4 is a graph showing Co-0124 growth over time in liquid media at each butanol concentration (0%-1.6% butanol). For Co-0124, $OD_{600}$ increased at the 24 and 96 hr time points up to 1.6% (v/v) butanol. FIG. 5 is a graph showing Co-7449 growth over time in liquid media at each butanol concentration (0%-1.6% butanol). For Co-7449, $OD_{600}$ increased at the 24 and 96 hr time points up to 1.4% (v/v) butanol.

FIG. 6A is a table showing the three strains, Co-5673, Co-7449, and Co-0124 that were analyzed for butanol tolerance on solid media plates (P2+4% Xylose) at the 24 hour time point. Butanol tolerance in liquid media was based on increase in $OD_{600}$ compared to the starting $OD_{600}$. Observed growth on solid media plates indicated butanol tolerance. Co-5673 showed growth on plates containing 0% and 2.2% butanol. Co-0124 showed growth on plates containing 0% and 2.2% butanol. Co-7449 showed growth only on plates containing 0% butanol. FIG. 6B is a comparison of the butanol tolerance of the three strains grown in liquid and on solid media at the 24 hr time point. The butanol tolerance result on solid media (2.1%) for Co-7449 at 24 hr was determined in a separate experiment from the other two strains. A higher butanol tolerance is exhibited for all three strains when grown on solid media at 24 hours.

FIG. 7A is a table showing the three strains, Co-5673, Co-7449, and Co-0124 were analyzed for butanol tolerance on solid media plates (P2+4% Xylose) at the 96 hour time point. Butanol tolerance in liquid media was based on the increase in $OD_{600}$ compared to the starting $OD_{600}$. Observed growth on solid media plates indicated butanol tolerance. Co-5673 showed growth on plates containing 0% and 2.2% butanol. Co-0124 showed growth on plates containing 0%, 2.2%, and 2.3% butanol. Co-7449 showed growth only on plates containing 0%, and 2.2% butanol. FIG. 7B is a comparison of the butanol tolerance of the three strains grown in liquid and on solid media at the 96 hr time point. A higher butanol tolerance is exhibited for all three strains when grown on solid media at 96 hours compared to liquid media. The higher butanol tolerance of various strains of *C. acetobutylicum* found when these microorganisms are cultured on solid support is a surprising result that if it holds true with other microorganisms including other strains of *C. acetobutylicum* and other species of *Clostridium* holds the potential to increase volumetric productivity for biofuels and also reduce separation costs due to reduced energy requirements.

Example 5

Adapting a Butanol Tolerant Microorganism from an Environmental Sample

An environmental sample (isolate) is obtained. The isolate is plated on a set of identical plates containing a nutrient agar. The plates have an increasing concentration of butanol ranging from 1.0%, 1.2%, 1.4%, 1.6%, 1.8%, and 2.0%. Plates with 1.0%, 1.2%, and 1.4% overgrow, while the plate with the 1.6% has several colonies. No growth is seen on the plates with 1.8% or 2.0% butanol. Colonies are picked from the 1.6% plate and serially passaged on solid support that contains ever increasing concentrations of butanol. After 20 passages, a strain adapted for growth in 2.5% butanol is obtained.

Example 6

Immobilized Continuous Culture Set-up and Operation

A continuous fermentation process with a packed column of immobilized Co-7449 cells on 10×28 mesh bone char was set up using a 0.15 L column with a void fraction of 0.665 and flowing P2 media with 3% glucose through the column at a rate of 0.36 L/h. Cells of a Co-7449 were first immobilized onto the column by attaching the column to a batch fermentation of Co-7449 in mid-level growth and circulating media from that batch fermentation through the column and then back to the fermentor for a period of about 24 h.

After cells were immobilize onto the packed column, the outlet stream of the column was then disconnected from the batch fermentor and attached to another harvest tank. The flow rate to the column from the fermentor was set to 0.36 L/h. Media was also continuously added to the fermentor from a 100 L sterile media bag to maintain the same media volume in the fermentor. The temperature of the packed column was maintained at a temperature that allowed bacterial growth by passing the outlet stream from the fermentor through a heat exchanger, which heated the media, before flowing through the column. The system was kept anaerobic by sparging nitrogen through the fermentation media being supplied to the column. Using these conditions, the packed column with immobilized Co-7449 produced a butanol titer of 1.36 g/L with a yield of 0.24 g butanol/g glucose and a productivity of 4.9 g butanol/(L*h) at a dilution rate of $3.6\ h^{-1}$.

Example 7

Immobilized Continuous Culture Set-up and Operation

An immobilized continuous culture is established by immobilizing cells of a butanol tolerant mutant of Co-7449 that has a butanol tolerance of 5.0%. A column packed with 10×28 mesh bone char is used as described in Example 6 above. After the cells are immobilized onto the packed column, the inlet stream from the seed batch fermentor and the return outlet stream to the seed batch fermentor are disconnected. A feed line from a 100 L sterile media bag is attached to the column and an outlet line from the column is routed back to the media bag. The flow rate of media to the column is set to 0.36 L/h. The temperature of the packed column is maintained at a temperature that allows bacterial growth by passing the outlet stream from the media bag through a heat exchanger before entering the column. Evolving fermentation gas is allowed to escape through a fermentation lock. Using these conditions, the packed column with immobilized Co-7449 mutant produces a butanol titer of over 10 g/L.

Example 8

Fermentation

Figure 8:
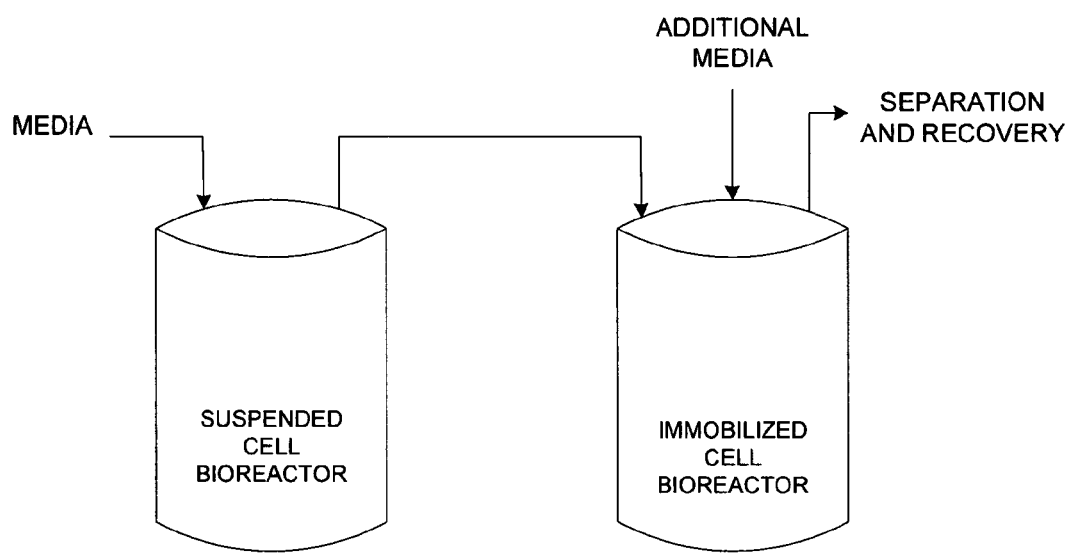
FIG. 8 illustrates a system comprising a bioreactor with suspended cells and a bioreactor with immobilized cells, arranged in series. Media is introduced into the suspended cell bioreactor and the fermentation effluent is removed and introduced into the immobilized cell bioreactor, along with additional media. The immobilized cell bioreactor contains isolated, adapted strains or mutants with butanol tolerance exhibiting increased product tolerance that can utilize residual substrate in the media, creating a higher concentration of product. The fermentation effluent is then removed and sent to separation and recovery.

A primary fermentation broth is generated using a fermentation processes such as batch, fed-batch or continuous fermentation, wherein the microorganisms are grown in suspension culture or immobilized on a solid support. This primary fermentation broth contains some acid and/or solvent titer and residual unassimilated feedstock. Further utilization of the residual feedstock for increased productivity and titer is achieved by placing a second bioreactor comprising immobilized product tolerant mutant microorganisms in series with the first bioreactor, as illustrated in FIG. 8. Additional feed can be added as desired to further increase productivity and titer and thereby lower separation and recovery energy requirements. At the conclusion of the fermentation process, the fermentation broth is sent for separation and recovery of the fermentation products.

As will be appreciated, multiple configurations of bioreactors are possible. Two or more bioreactors can serve as primary bioreactors with suspension or immobilized cells. Two or more bioreactors can be placed in series, with each successive bioreactor containing a mutant microorganism with a higher tolerance to product. Additionally, with bioreactors in series, specific process parameters for each bioreactor can be optimized such as dilution and feed rates, media components, and temperature. This feature may be particularly important when individual bioreactors in series contain different strains or species of microorganisms, or consortiums of microorganisms.

Regardless of the bioreactor configurations, further savings in feedstock and water usage is obtained by recycling processed fermentation effluent from the separation and recovery stage where it can serve as a basis for initial fermentation media in a bioreactor, or feed stream. In this way, unassimilated and/or recovered nutrients and minerals (e.g. iron) are utilized.

Exemplary Determination of Packed Bed Zone, Expanded Bed Zone and H:Hp for a Select Solid Support Material Examples 9-13 exemplify a methodology used to calculate specific design parameters for a duel mode bioreactor. In the examples, bonechar was selected as the solid support material, but the design parameters for other solid support and semi-solid support can also be generate using this same or a similar approach.

Example 9

Calculation of Equivalent Diameters for Bonechar Particles

Bonechar particles have irregular shapes, however, equivalent diameters can be calculated from terminal settling velocities thereby giving estimates of the particle-fluid interactions of "equivalent" spheres of the same density. Due to variations in bonechar shape and size, equivalent diameters were obtained for the mean settling velocities, and for +/−one standard deviations (+/−σ) from the mean settling velocities.

Bonechar Particle Information

| Bonechar Type | Particle Density (g/mL) | Size (microns) | Shape | Settling Velocity (cm/s ± σ) | Bulk Density (g/mL) | Void Fraction |
|---|---|---|---|---|---|---|
| 5 × 8 | 2.27 | 3000-5000 | varies - flat | 11.42 ± 2.57 | 0.72 | 0.625 |
| 10 × 28 | 2.36 | 900-2500 | rectangles and | 6.40 ± 1.56 | 0.69 | 0.63 |
| 20 × 60 | 2.38 | 400-1300 | flat squares to splinter shape | 4.42 ± 0.97 | 0.74 | 0.65 |

Figures 9A, 9B:
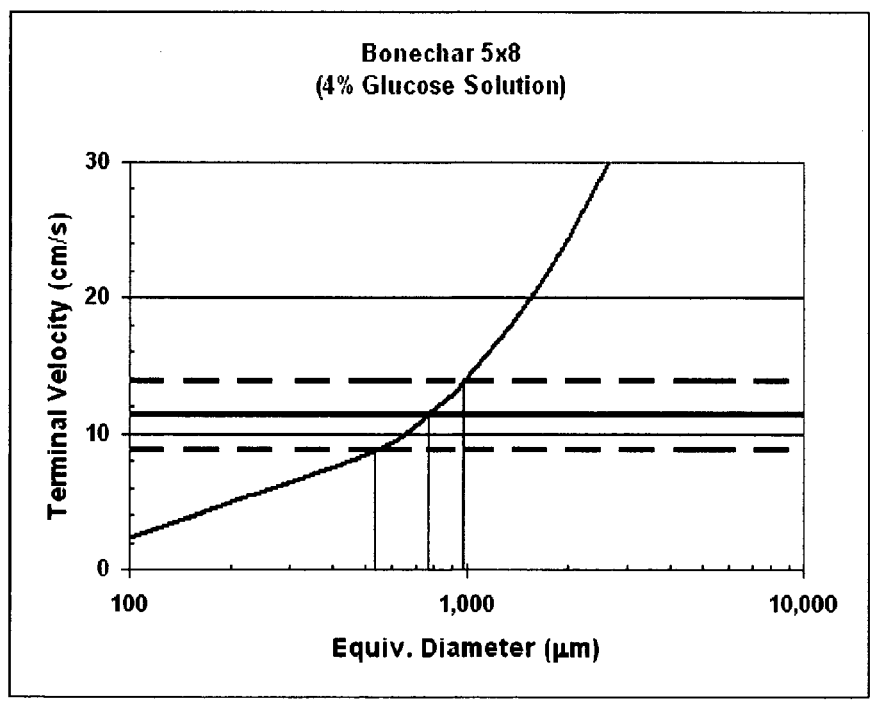
FIG. 9A is table containing three examples of bonechar particles of different sized mesh, their settling velocity (cm/s), and their equivalent diameter (μm).
FIG. 9B is a graphical representation of the equivalent diameter of bonechar type 5×8 in 4% glucose solution using terminal settling velocity.

FIG. 9A shows a table containing three, non-limiting, examples of bonechar particles of different sized mesh, their settling velocity (cm/s), and their equivalent diameter (μm). FIG. 9B is a graphical representation of the equivalent diameter of bonechar type 5×8 in 4% glucose solution using the terminal settling velocity.

Example 10

Minimum Fluidization Velocities for Bonechar Particles

Estimations of the minimum liquid velocities required to fluidize bonechar particles was done using the Ergon equation for pressure drop. This minimum fluidization velocity ($U_{mf}$) was calculated for three types of bonechar particles, based on the particle densities and equivalent spherical diameters disclosed in Example 9. Properties of the liquid were taken to be that of 4% glucose aqueous solution at 35° C.

For each type of particle, 3 sizes were used for the equivalent diameters, corresponding to the reported mean settling velocity, and +/−one standard deviation (+/−σ) from the respective mean (see Example 9).

The minimum fluidization velocity is dependent on the packing density (void fraction, $\epsilon_{mf}$) prior to fluidization. Since this is unknown is as of yet unknown, the results were calculated over a range of void fractions. For spherical particles, a common value for $\epsilon_{mf}$ is in range of 0.35-0.45. For particles of odd shapes and mixed sizes, the void fraction could be significantly different.

Figures 10A, 10B:
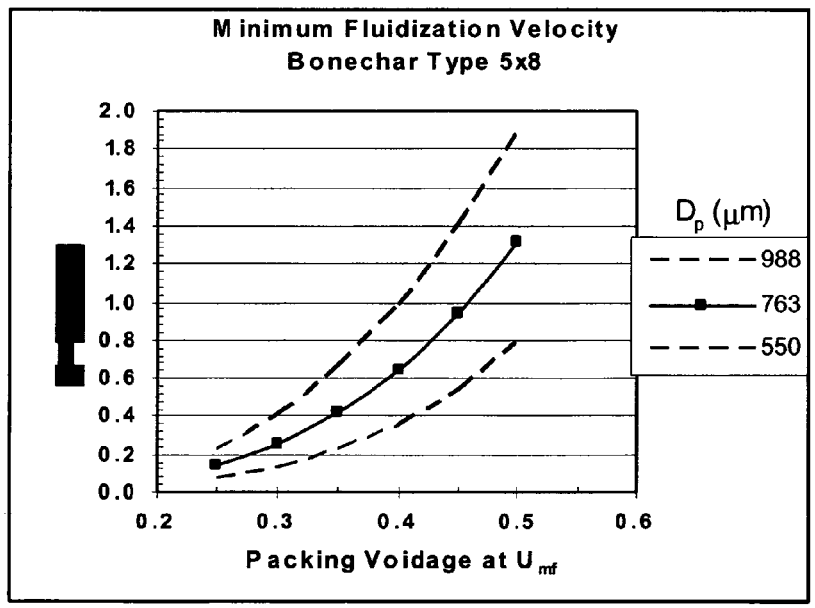
FIG. 10A is a table showing the minimum fluidization velocity ($U_{mf}$) calculated over a range of void fractions at different equivalent diameters for bonechar type 5×8 in 4% glucose solution.
FIG. 10B is a graphical representation of the minimum fluidization velocity ($U_{mf}$) calculated over a range of void fractions for different equivalent diameters for bonechar type 5×8.
Figures 11A, 11B:
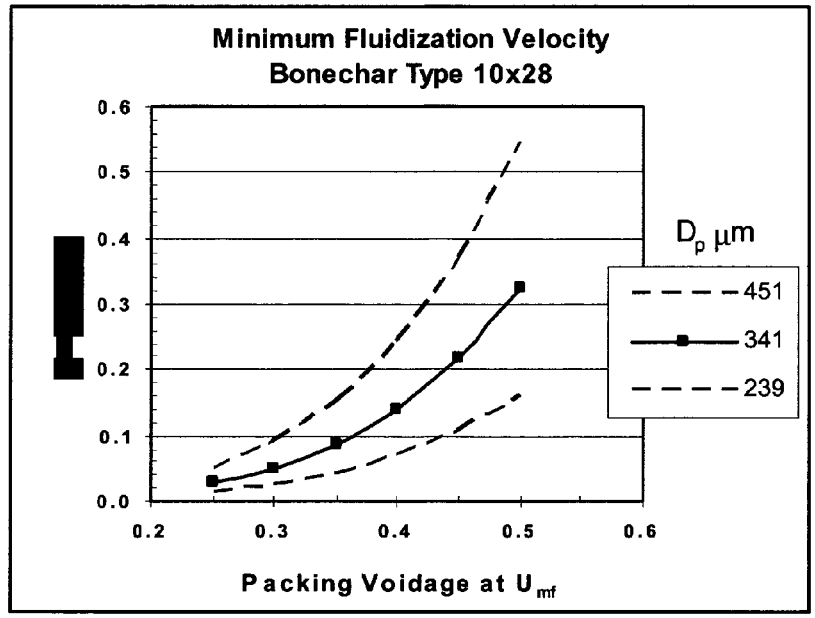
FIG. 11A is a table showing the minimum fluidization velocity ($U_{mf}$) calculated over a range of void fractions at different equivalent diameters for bonechar type 10×28 in 4% glucose solution.
FIG. 11B is a graphical representation of the minimum fluidization velocity ($U_{mf}$) calculated over a range of void fractions for different equivalent diameters for bonechar type 10×28.
Figures 12A, 12B:
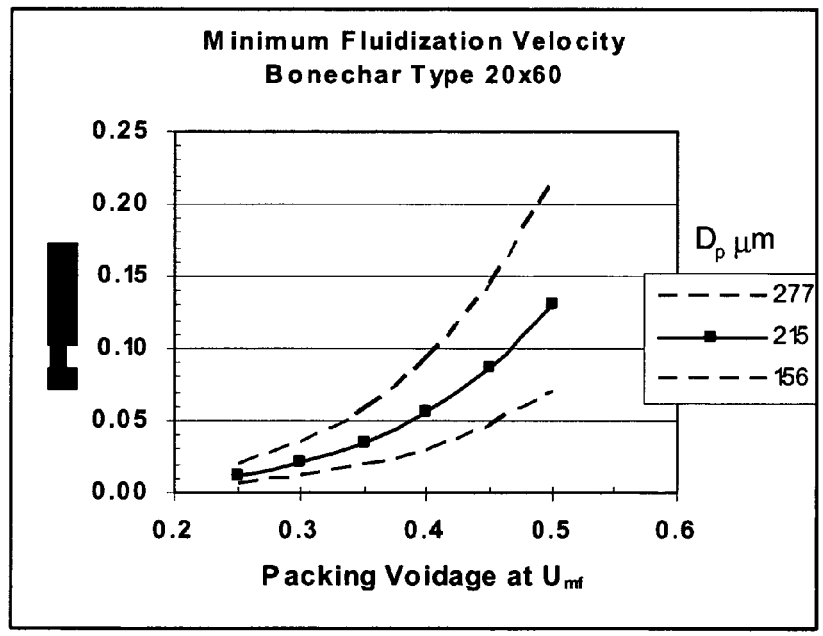
FIG. 12A is a table showing the minimum fluidization velocity ($U_{mf}$) calculated over a range of void fractions at different equivalent diameters for bonechar type 20×60 in 4% glucose solution.
FIG. 12B is a graphical representation of the minimum fluidization velocity ($U_{mf}$) calculated over a range of void fractions for different equivalent diameters for bonechar type 20×60.

Results for the three types of bonechar are presented in tables and graphs shown in FIGS. 10, 11, and 12. FIGS. 10A, 11A, 12A are tables showing the minimum fluidization velocity ($U_{mf}$) calculated over a range of void fractions at different equivalent diameters for bonechar types 5×8, 10×28, and 20×60 in 4% glucose solution, respectively. FIGS. 10B, 11B, 12B are graphical representation of the minimum fluidization velocity ($U_{mf}$) calculated over a range of void fractions for different equivalent diameters.

In order to be able to fluidize the larger particles (+1σ size) in each type of bonechar, the minimum fluidization velocities is taken to be no less than those corresponding to the larger diameter in each type, at an $\epsilon_{mf}$ of 0.45, as listed below:

| Bonechar Type | Minimum Fluidization Velocity (cm/s) |
|---|---|
| 5 × 8 | 1.394 |
| 10 × 28 | 0.371 |
| 20 × 60 | 0.144 |

These minimum fluidization velocities are estimated values, with some degree of uncertainty due to odd shape of particles, a range of sizes for each type, and unknown packing densities. The above listed values are taken as minimum values for equipment capability. Operations in packed-bed mode will occur at lower velocities, and operation in fluidized expanded-bed mode will occur at somewhat higher velocities. Additionally, the calculations are for clean particles; as the biofilm grows on the particles, it is anticipate that there will be changes in effective diameters and in velocity requirements. For such uncertainties, a safety factor is built in, i.e. some capability to exceed these velocities.

Example 11

Bed Expansion for Fluidized Bonechar Particles

When solid particles are fluidized by upward flowing liquid, the bed expands beyond the level of the original packed bed for liquid velocities greater than the minimum fluidization velocity. Using the model of Richardson & Zaki (Richardson, J. F. and Zaki, W. N. 1954. Sedimentation and fluidization: Part I. *Trans. Inst. Chem. Eng.* 32:35-53), and the correlation of Richardson & Khan (Khan, A. R. and Richardson, J. F. 1989. Fluid-particle interactions and flow characteristics of fluidized beds and settling suspensions of spherical particles. *Chem. Eng. Comm.* 78:111-130), a program was written to estimate the bed expansion levels for three types of bonechar particles (5×8, 10×28, and 20×60). The original correlation was developed for mono-sized particles and thus involves some degree of uncertainty since each type of bonechar has a range of particle sizes. For this analysis, the model was applied as if the beds are comprised of mono-sized particles of diameter equal to the equivalent "mean" diameter. To gain some estimate of possible variations, the calculations were repeated for mono-sized particles of diameters equal to +1σ "larger" and −1σ "smaller", in terms of settling velocities:

| Bonechar Type | Equivalent Diameters (μm) | | |
|---|---|---|---|
| | Larger | Mean | Smaller |
| 5 × 8 | 988 | 763 | 550 |
| 10 × 28 | 451 | 341 | 239 |
| 20 × 60 | 277 | 215 | 156 |

The bed expansion depends, not only on particle size and liquid velocity, but also on bed diameter ($D_{bed}$) and on the voidage at minimum fluidization ($\epsilon_{mf}$). For this example, the analysis used a bed diameter of $D_{bed}$=10 cm, and a void fraction of $\epsilon_{mf}$=0.5.

Figures 15A, 15B:
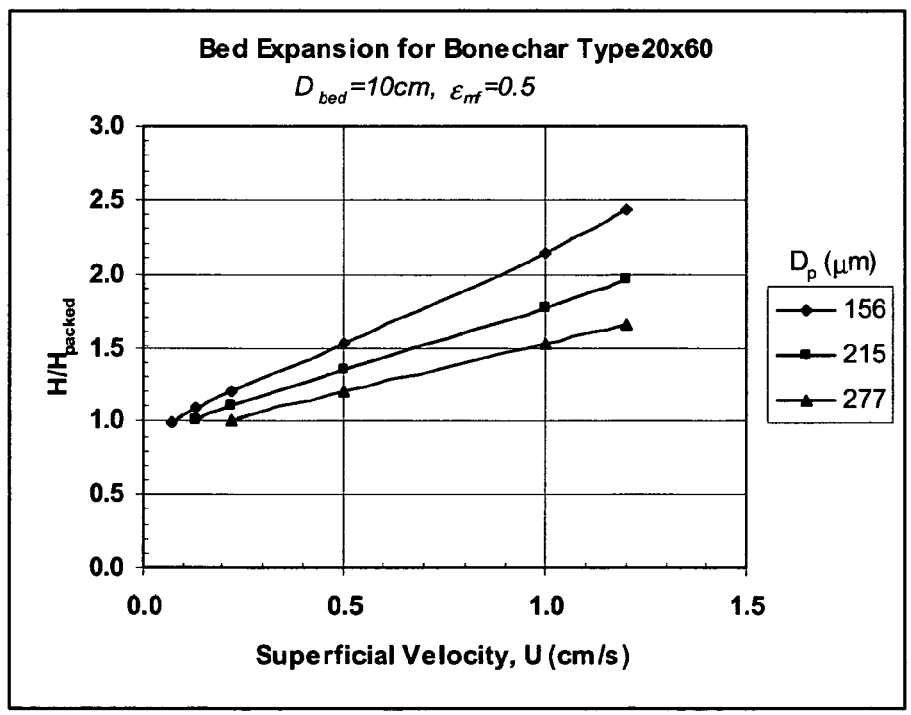
FIG. 15A illustrates the parameters used to calculate bed expansion levels for bonechar type 20×60. Results are in the form of ratios for expanded bed height to packed bed height ($H/H_{packed}$).
FIG. 15B, is a graphical representation of the bed expansion for bonechar type 20×60.

Results are presented in the tables and graphs shown in FIGS. 13, 14, and 15 and are in the form of ratios for total height of the expanded bed to packed bed height (H/H$_{packed}$). FIGS. 13A, 14A, 15A show the parameters used to calculate bed expansion levels. FIGS. 13B, 14B, 15B are graphical representations of the bed expansion for bonechar types 5×8, 10×28, and 20×60, respectively. The spread in this ratio, between the larger and the smaller particles in each type of bonechar, was greatest for Type 5×8 (FIG. 13) and least for Type 20×60 (FIG. 15). This implies that it will be more difficult to retain the smaller particles in the expansion zone of the bioreactor for 5×8 bonechar, easier for the 10×28 bonechar, and easiest for the 20×60 bonechar.

For a bioreactor capable of running in both packed bed and fluidized bed mode, it is desirable to retain the smaller particles in the bed expansion zone (FIGS. 19 and 20), while still achieving fluidization of the larger particles. Thus, for each type of bonechar, the total height of the expanded bed to packed bed height ratio (H/H$_{packed}$) for the smaller particles at a liquid superficial velocity was just slightly greater than the minimum fluidization velocity for the larger particles. From the calculated tables and graphs, this condition was found to be as follows, for each type of bonechar:

| Bonechar Type | Superficial Velocity ($U_{mf}$ cm/s) For Larger Particles | Total Height of Expanded Bed to Packed Bed Height Ratio H/H$_{packed}$ For Smaller Particles |
|---|---|---|
| 5 × 8 | 1.88 | 1.38 |
| 10 × 28 | 0.55 | 1.32 |
| 20 × 60 | 0.22 | 1.21 |

Therefore, a bioreactor designed for use with all three types of bonechar, the largest total height of expanded bed to packed bed height ratio, (i.e. H/H$_{packed}$ of ~1.4) should be selected for the bioreactor design.

Example 12

Design Requirements for a Dual Mode Packed Bed-Fluidized Bed Bioreactor

Design requirements for a dual mode packed bed-fluidized bed bioreactor are based on the correlations and calculations described in Examples 9, 10, and 11. The design was based on the following premises:
1. Reactor is to operate with immobilized cells on bonechar particles.
2. Reactor volume (of the packed bed) is a parameter to be selected.
3. Reactor should be able to operate in either packed-bed or fluidized-bed modes.
4. Maximum liquid flow should be capable of fluidizing the largest particles present in the selected grade of bonechar.
5. Sufficient height should be allowed for expansion of the fluidized bed, even for the smallest particles in the selected grade of bonechar.

A spreadsheet program was written to calculate the design parameters needed for a packed bed-fluidized bed bioreactor with the above requirements. These calculations exercise the software described in Examples 9, 10, and 11 for determining equivalent particle diameters, minimum fluidization velocities, and bed expansion heights.

For a given set of specifications (reactor volume, bed diameter, type of bonechar, liquid properties) the design calculations were determined for the:
1. Height of packed zone.
2. Height for bed expansion zone.
3. Rate of liquid flow to achieve fluidization.

The bed diameter was left as a variable, since the final design choice depends on component availability. The flow rates utilized in the packed-bed mode, the pressure drop across the bed, and the design of the upper disengagement vessel were not included in the calculations.

Figures 16A, 16B:
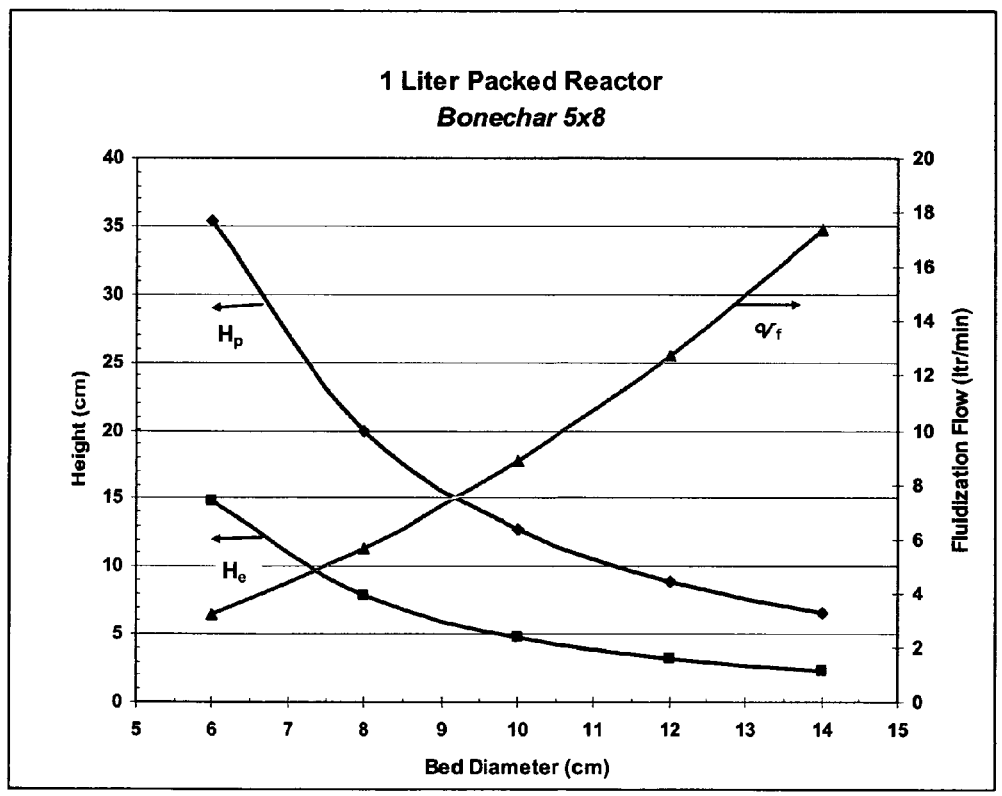
FIG. 16 illustrates the design calculations to determine the height of packed zone, height for bed expansion zone, and the rate of liquid flow to achieve fluidization for bonechar type 5×8.
Figures 17A, 17B:
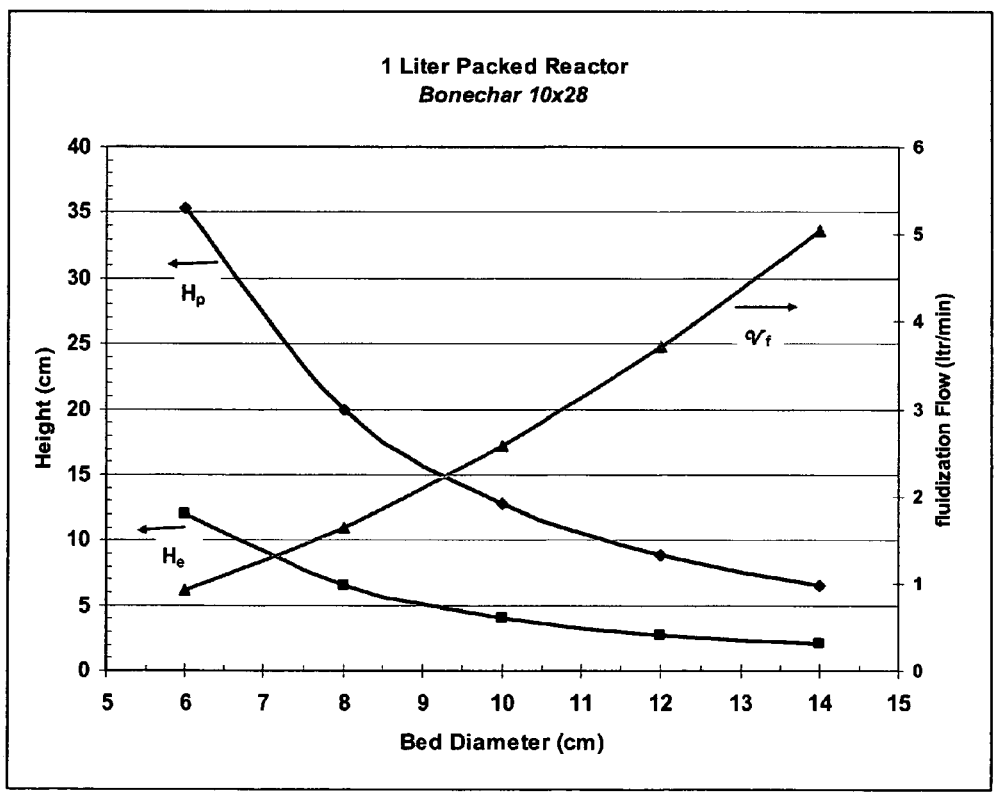
FIG. 17 illustrates the design calculations to determine the height of packed zone, height for bed expansion zone, and the rate of liquid flow to achieve fluidization for bonechar type 10×28.
Figures 18A, 18B:
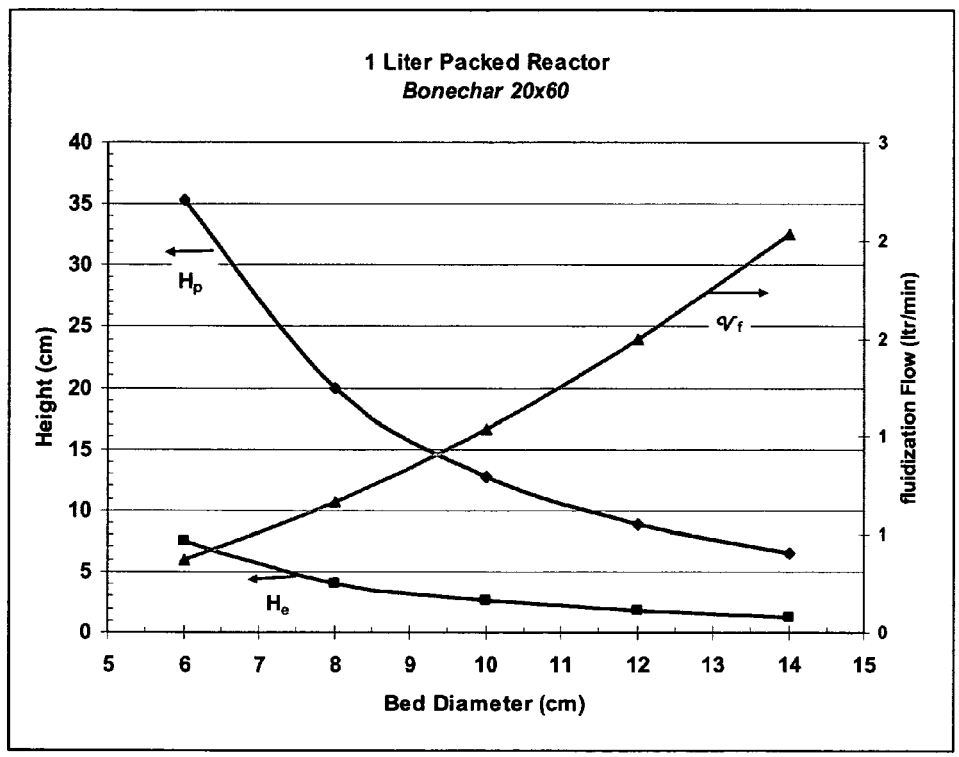
FIG. 18 illustrates the design calculations to determine the height of packed zone, height for bed expansion zone, and the rate of liquid flow to achieve fluidization for bonechar type 20×60.

Results for the three types of bonechar particles, 5×8, 10×28, and 20×60 are presented in FIGS. 16, 17, and 18, respectively. These results were calculated specifically for the case of:
Reactor volume ($V_R$)=1 liter.
Voidage at minimum fluidization ($\epsilon_{mf}$)=0.5.
Bed diameter ($D_b$) variable over range 6-14 cm.
The following table compares design requirements for the three types of bonchar, for case of $D_b$=8 cm.

| Bonechar Type | Required Flow $V_f$ (ltr/min) | Required Expansion Height $H_e$ (cm) |
|---|---|---|
| 5 × 8 | 5.67 | 7.79 |
| 10 × 28 | 1.65 | 6.52 |
| 20 × 60 | 0.66 | 4.08 |

Similar results can be read from the graphs in FIGS. 16, 17, and 18, for different bed diameters. The calculations can be redone if different specifications are chosen for reactor volume or if voidage at minimum fluidization is found to be other than 0.5.

The following observations were noted:
Required liquid flow rate is highest for type 5×8, least for type 20×60 bonechar.

Height requirement for bed expansion is greatest for type 5×8, least for type 20×60 bonechar.

Therefore, it is easiest to achieve the dual mode capability for type 20×60 bonechar, and most difficult for type 5×8 bonechar.

Conversely, a reactor designed for type 20×60 bonechar is unlikely to be operable in fluidized mode for the other two types of bonechar particles.

Figure 19:
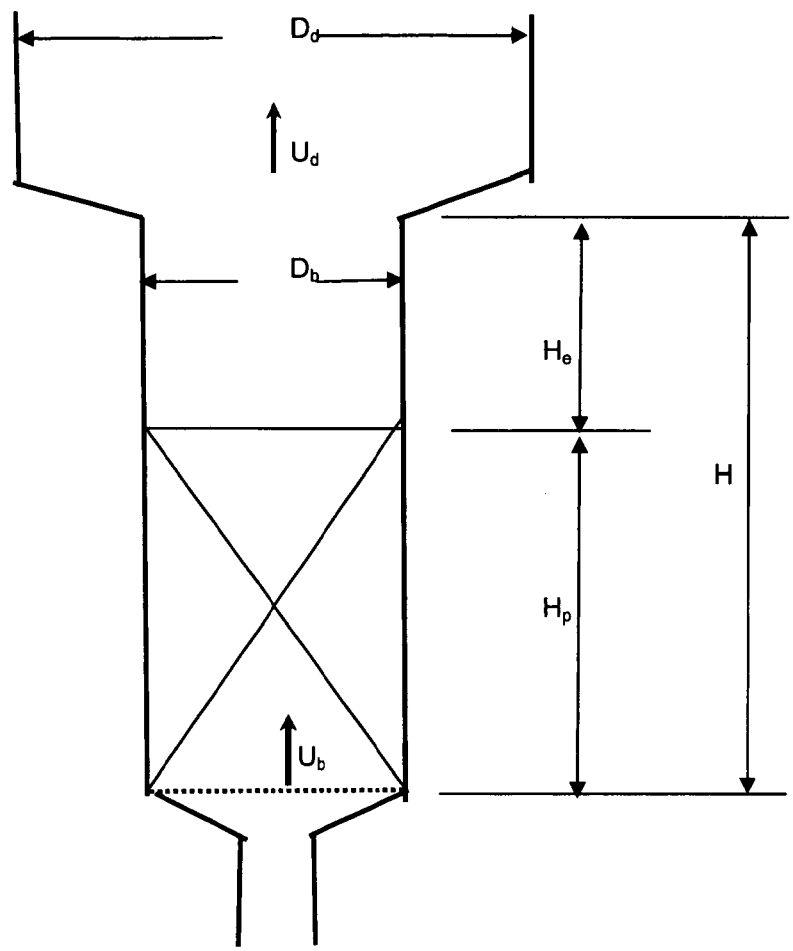
FIG. 19 illustrates a sample reactor concept.
Figure 19B:
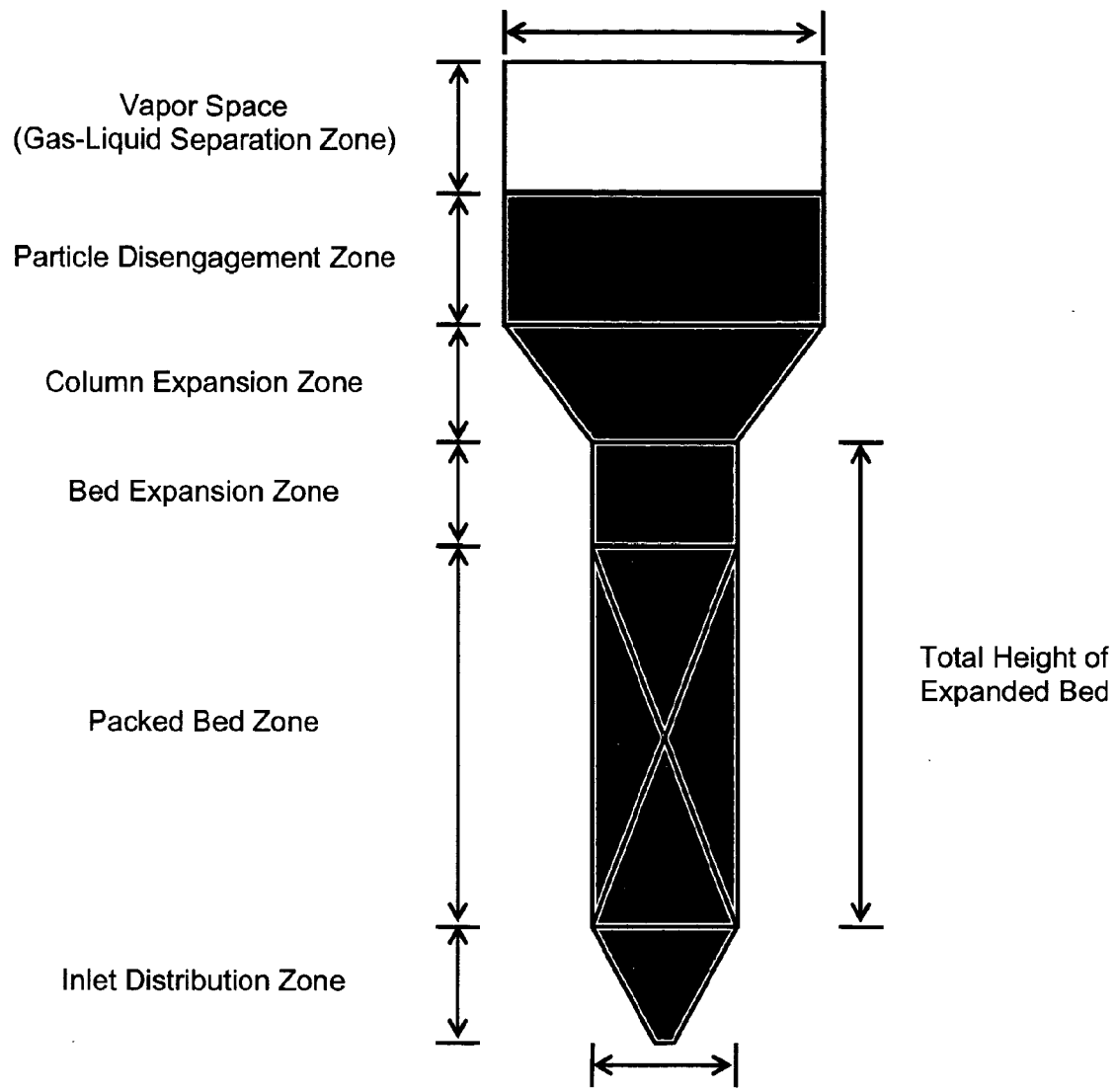

FIGS. 19A and 19B illustrate the dual mode bioreactor concept. The nomenclature used in FIGS. 16, 17, 18, and 19 is as follows:

$V_R$=volume of reactor in packed-bed zone
$D_b$=diameter of reactor bed vessel
$D_d$=diameter of disengagement vessel
$D_p$=diameter of bonechar particle
$H_p$=height of packed bed
$H_e$=height of expansion region in fluidized operation
H=total height of expanded bed=$H_p$+$H_e$
$U_b$=superficial liquid velocity in bed vessel
$U_d$=superficial liquid velocity in disengagement vessel
$\mathcal{V}_p$=volumetric flow rate of liquid through reactor in packed mode
$\mathcal{V}_f$=volumetric flow rate of liquid through reactor in fluidized mode The duel mode bioreactors usually have a columnar shaped that is configured to include several discrete zones. FIG. 19B They are arranged usually in a vertical position in the following sequential order:

a) a packed bed zone comprising particles therein, the particles comprising microorganisms thereon for fermenting the biological product;

b) a bed expansion zone coupled to said packed bed zone for expansion of the particles in a fluidized bed mode; and c) a particle disengagement zone coupled to the bed expansion zone, the particle disengagement zone allowing the particles to settle when the particle are in a fluidized bed mode.

The inlet for a dual mode bioreactor is usually located at the bottom of a vertically positioned bioreactor where the fluid flows in a vertical manner and where the above zones are arranged in an ascending order from packed bed zone to the particle disengagement zone. The packed bed zone contains the solid support when the flow rate is below the rate needed to fluidize the largest support particles. The bed expansion zone is designed to allow expansion of the bed at increased liquid inlet flow rates to enable more uniform axial mixing and to breakup aggregated particles formed by the growth of biofilms. The latter property is useful in the intermittent expansion (fluidization) of the packed bed to prevent plugging, allowing longer fermentation time and therefore, less frequent bioreactor turnaround. The particle disengagement zone is an area of lower fluid velocity that allows for the separation of the suspended particles from the fermentation broth thereby allowing for the fermentation broth to be drawn off the bioreactor free of suspended particles. Where a product, such as butanol, reaches a concentration that spontaneously phase separates into a product phase and an aqueous phase, the particle disengagement zone can also act as a phase separation zone, allowing the product rich organic phase to be withdrawn directly from the bioreactor.

The bioreactor may optionally feature a column expansion zone, an inlet distribution zone, and/or a gas-liquid separation zone. FIG. 19B The inlet distribution zone distributes incoming fluid uniformly across the packed bed of solid support material. The pressure drop across the inlet distribution zone is generally designed to be no more than 30%, 25%, 20%, 15%, 10%, or 5% of the total pressure drop across the length of the bioreactor. The gas-liquid separation allows for evolved or introduced gases to separate from the liquid and thereby prevent gas entrainment in the effluent, and liquid entrainment in the gas. Typically, at least one of the column expansion zone, particle disengagement zone, and the gas-liquid separation zone has a diameter that is larger than the diameter of the packed bed zone.

Example 13

Analysis of Results from FIG. 20B

Examples 9-12 present calculations for fluidization characteristics of bonechar particles, based on models and correlations judged to be most appropriate from technical literature. FIGS. 20A and 20B show two sets of data collected for a pipet bed diameter of 1.6 cm with a bed area of 2 $cm^2$. FIG. 20B shows data collected for measurements of two key characteristics (minimum fluidization and bed expansion) for the actual bonechar particles. This data can be used along with the models to refine design features for a duel mode bioreactor. Based on the experimental data and the model predictions, the following conclusions and recommendations for design specifications of duel mode packed bed-fluidized bed bioreactors are made.

Minimum Fluidization

The minimum fluidization velocity ($U_{mf}$) of bonechar particles is dependent on particle size, density, shape, and packing void fraction ($\epsilon$). The void fraction is not known at this time for the irregularly shaped particles, therefore the estimates for $U_{mf}$ in Example 10 were based on a value of $\epsilon$=0.45.

Measured $U_{mf}$ were obtained and are slightly greater than the models' predictions, implying that actual void fractions are greater than 0.45. Based on the experimental values of $U_{mf}$, the models were used and new values for the void fraction (to correspond to the experimental $U_{mf}$) were calculated:

| Bonechar Type | Experimental $U_{mf}$ | Corresponding $\epsilon$ |
| --- | --- | --- |
| 5 × 8 | 1.88 | 0.50 |
| 10 × 28 | 0.86 | 0.56 |
| 20 × 60 | 0.33 | 0.55 |

The new values for s ranged from 0.50 to 0.56, which are reasonable, given the irregular shapes of bonechar particles. These void fractions will be used to make fluidization calculations.

For design, the experimental values of $U_{mf}$ will be used since they are slightly greater than original estimates. Using the larger values assure the ability to fluidize the particles.

Bed Expansion

A sufficient height of the duel mode bioreactor is required so that particles can be retained in the bioreactor when the bed is fluidized. Example 11 gave "safe" estimates for the ratio of expanded to packed bed heights (H/$H_{packed}$), and these are compared to the values measured shown in FIG. 20B:

| Bonechar Type | Model H/$H_{packed}$ | Exp. H/$H_{packed}$ |
| --- | --- | --- |
| 5 × 8 | 1.38 | 1.02 |
| 10 × 28 | 1.32 | 1.06 |
| 20 × 60 | 1.21 | 1.04 |

The model estimated heights are safe estimates, however, to reduce reactor volume and cost, based on these new experimental observations, a total expanded bed height to packed bed height ratio (H/H$_{packed}$) of 1.2 is sufficient for all three types of bonechars. In some embodiments, a H/H$_{packed}$ of not less than 1.01, 1.10, 1.15, 1.20, 1.25, 1.30, 1.35, 1.40, 1.45 is used in a duel mode, packed bed-expanded (fluidized) bed bioreactor. In other embodiments, a H/H$_{packed}$ ratio of not more than 1.01, 1.10, 1.15, 1.20, 1.25, 1.30, 1.35, 1.40, 1.45 is used in a duel mode, packed bed-expanded (fluidized) bed bioreactor.

Example 14

Immobilized Cell Packed Bed Bioreactor Data from Continuous Fermentation

Figure 21:
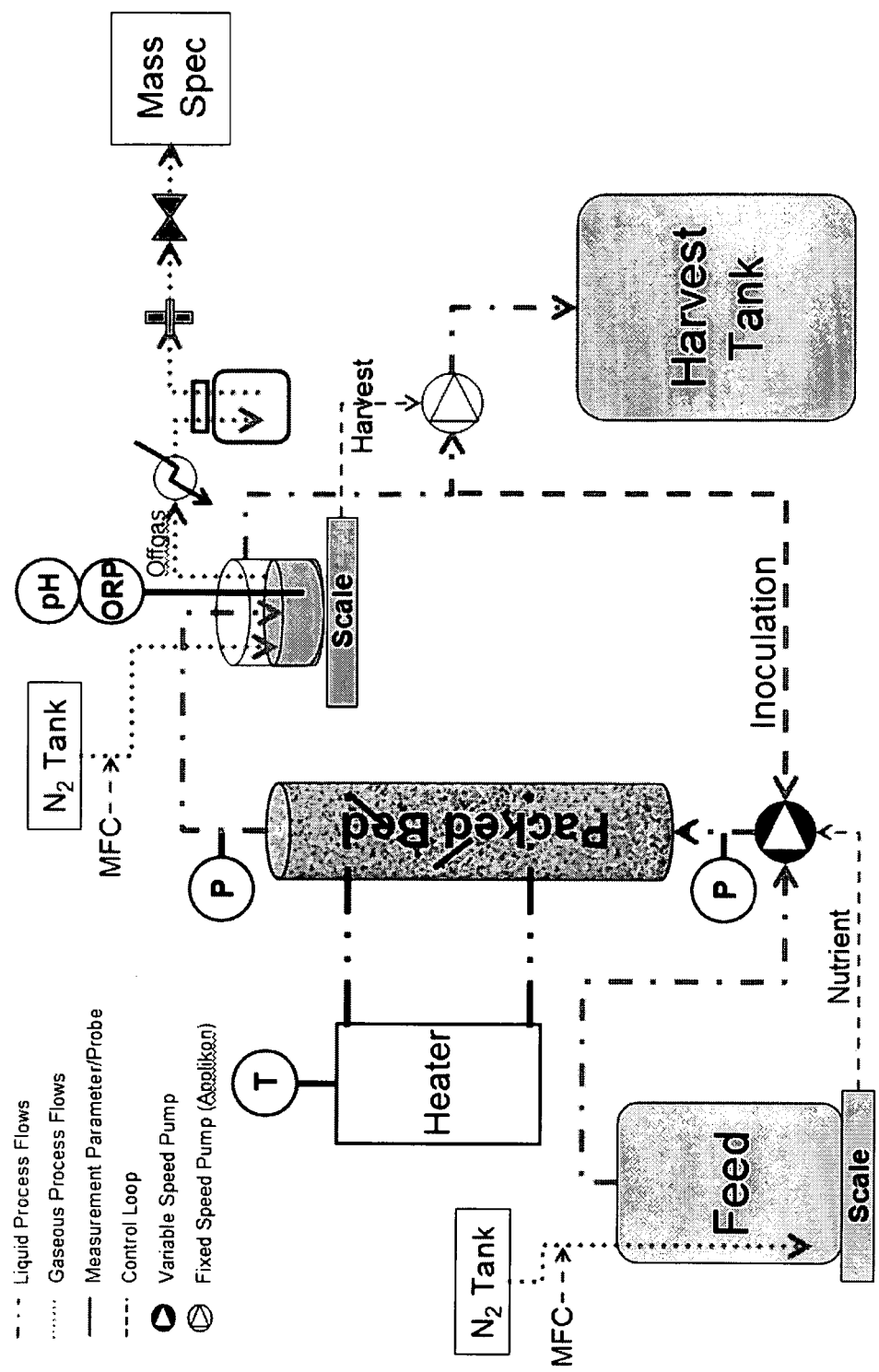
FIG. 21 is a scheme of an immobilized cell bioreactor set-up and control.

Immobilized cell packed bed bioreactors were set-up according the schematic shown in FIG. 21. Here, MFC is Mass Flow Controller, P is pressure, T is temperature, ORP is Oxidative Reductive Potential. Non-adapted or selected strains of *Clostridium saccharobutylicum* and *C. beijerinckii* were used. The bioreactors were seeded and started in batch mode and then switched over to continuous fermentation mode. Some of the bioreactors were run in batch and continuous mode for a combined time of over 1000 hours. OD$_{600}$ readings, feed rates, percent feedstock in culture media, butanol levels and butanol productivity are presented in graphical form for five runs in FIGS. 22-26. EFT is the elapsed fermentation time (hours). A summary of fermentation runs including the dilution rate, butanol titer, butanol yield and butanol productivity is provided in FIG. 27.

Figure 22:
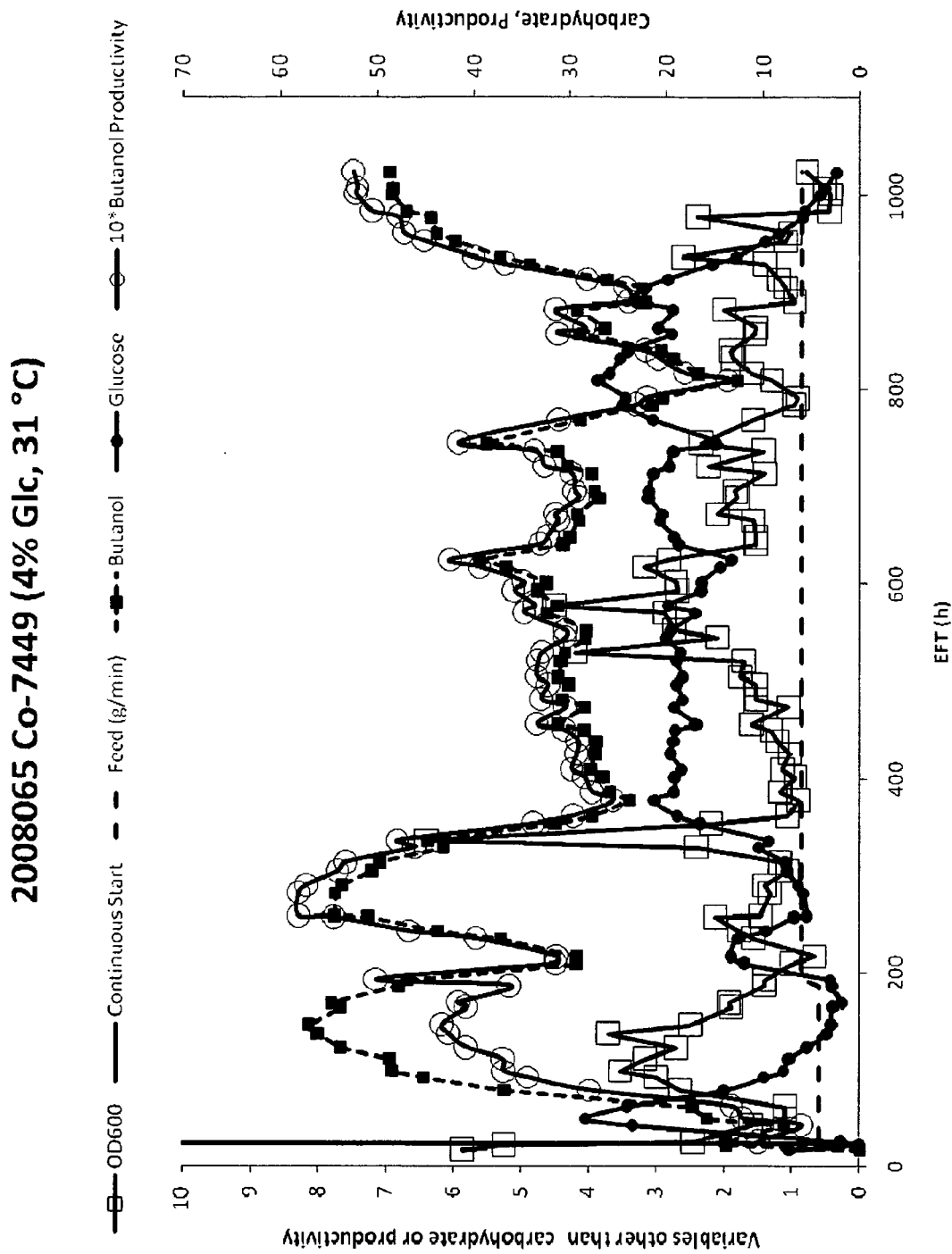
FIG. 22 shows the experimental traces of data obtained during continuous fermentation of Co-7449 in a 100 mL immobilized cell bioreactor.

FIG. 22 shows a graph of data generated from monitoring continuous fermentation run of Co-7449 in 100 mL immobilized cell bioreactor containing bonechar as the support (Run no. 2008065). The substrate was 4% glucose and the dilution rate was 0.73/h.

Figure 23:
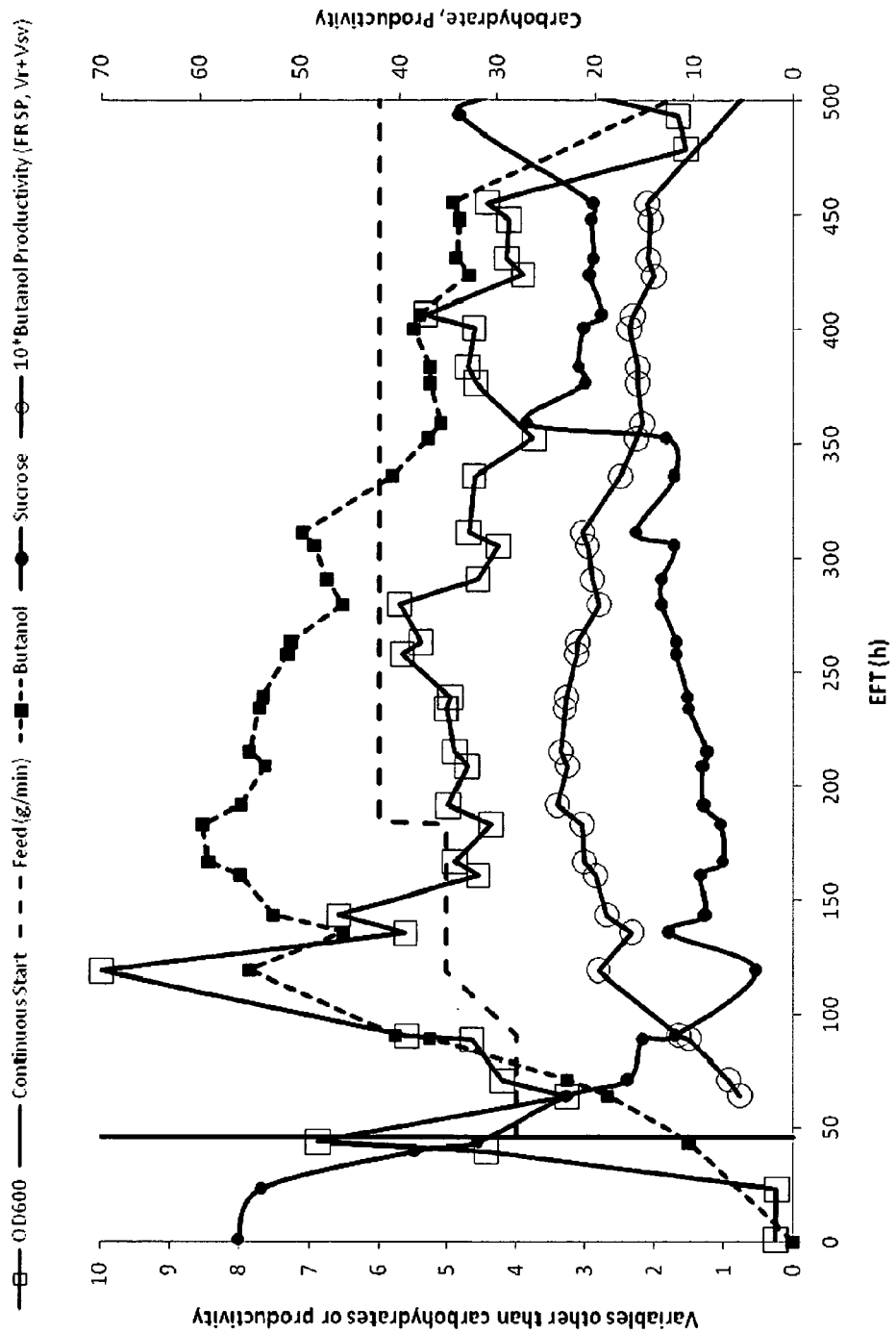
FIG. 23 shows the experimental traces of data obtained during continuous fermentation of Co-7449 in a 1000 mL immobilized cell bioreactor.

FIG. 23 shows a graph of data generated from monitoring continuous fermentation run of Co-7449 in 1000 mL immobilized cell bioreactor containing bonechar as the support at 31° C. (Run no. 2008137). The substrate was 4% sucrose and the dilution rate was 0.51/h.

Figure 24:
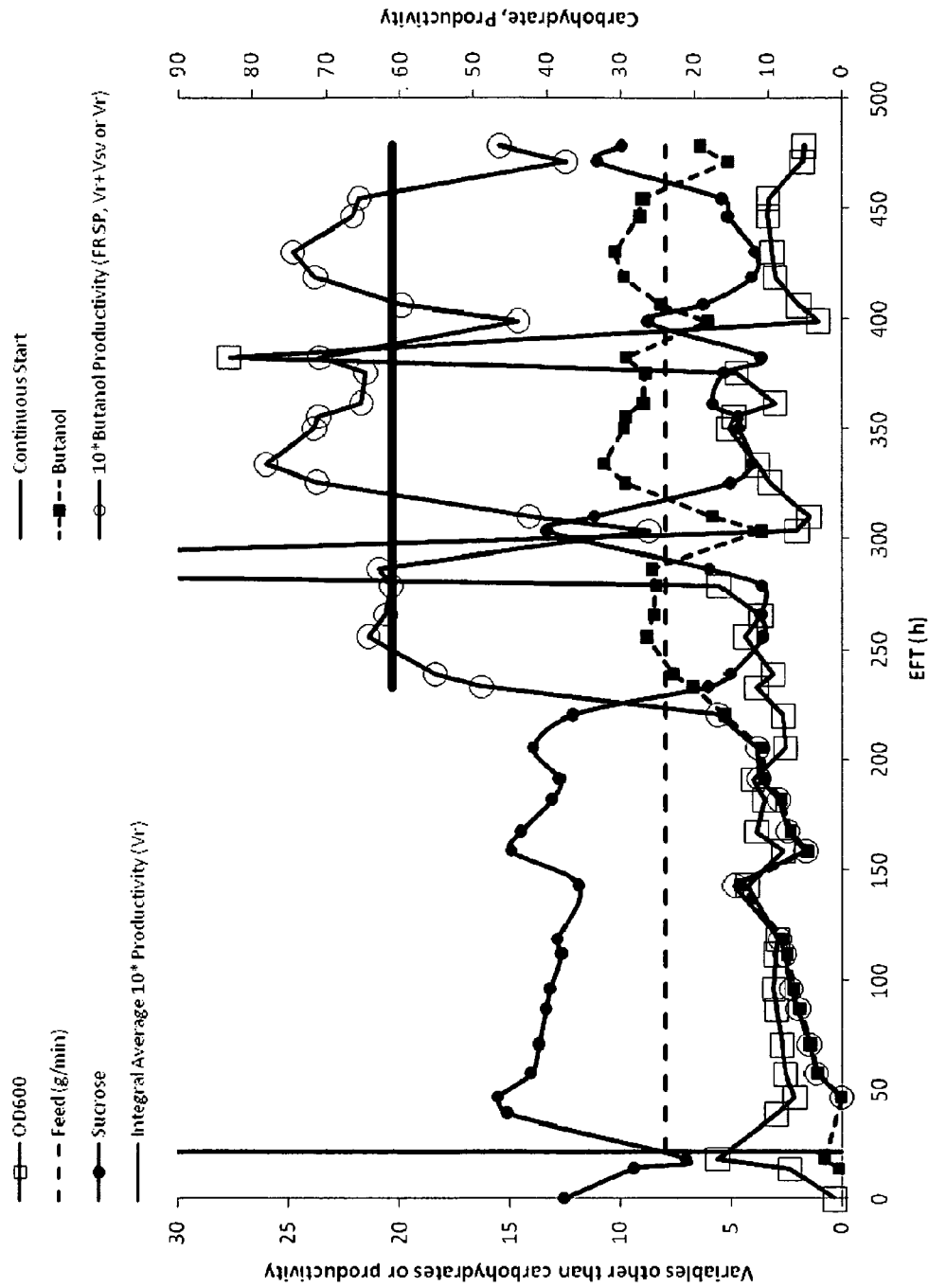
FIG. 24 shows the experimental traces of data obtained during continuous fermentation of Co-5673 in a 1000 mL immobilized cell bioreactor.

FIG. 24 shows a graph of data generated from monitoring continuous fermentation run of Co-5673 in 1000 mL immobilized cell bioreactor containing bonechar as the support at 33° C. (Run no. 2009012). The substrate was 5% sucrose and the dilution rate was 0.73/h. The solid straight horizontal black line running through the butanol productivity trace is the integral average of the butanol productivity data using trapezoidal rule for the time period indicated by the horizontal black line.

Figure 25:
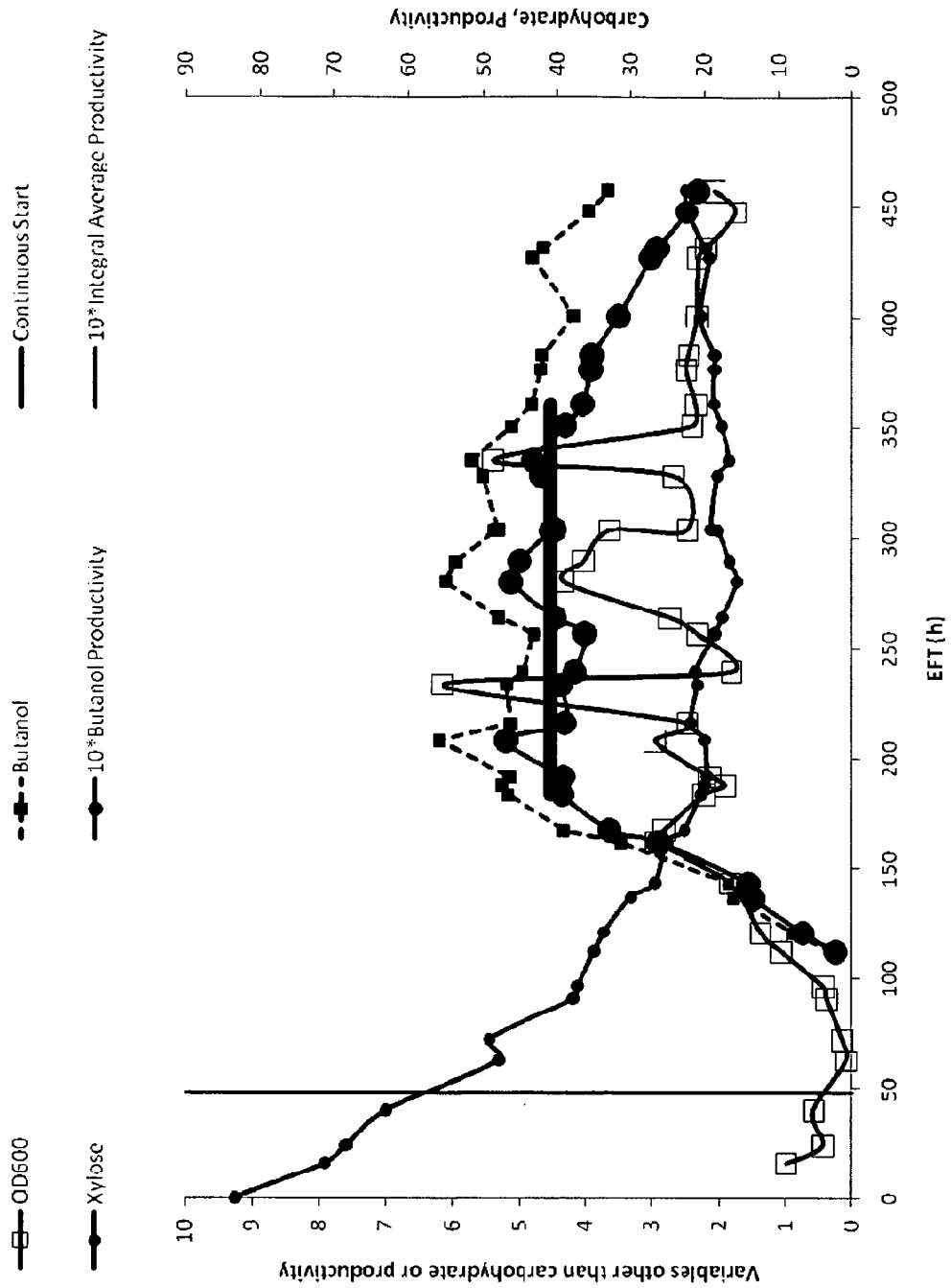
FIG. 25 shows the experimental traces of data obtained during continuous fermentation of Co-7449 in a 1000 mL immobilized cell bioreactor.

FIG. 25 shows a graph of data generated from monitoring continuous fermentation run of Co-7449 in 1000 mL immobilized cell bioreactor containing bonechar as the support at 31° C. (Run no. 2009021). The substrate was 4% xylose and the dilution rate was 0.76/h. The solid straight horizontal black line running through the butanol productivity trace is the integral average of the butanol productivity data using trapezoidal rule for the time period indicated by the horizontal black line.

Figure 26:
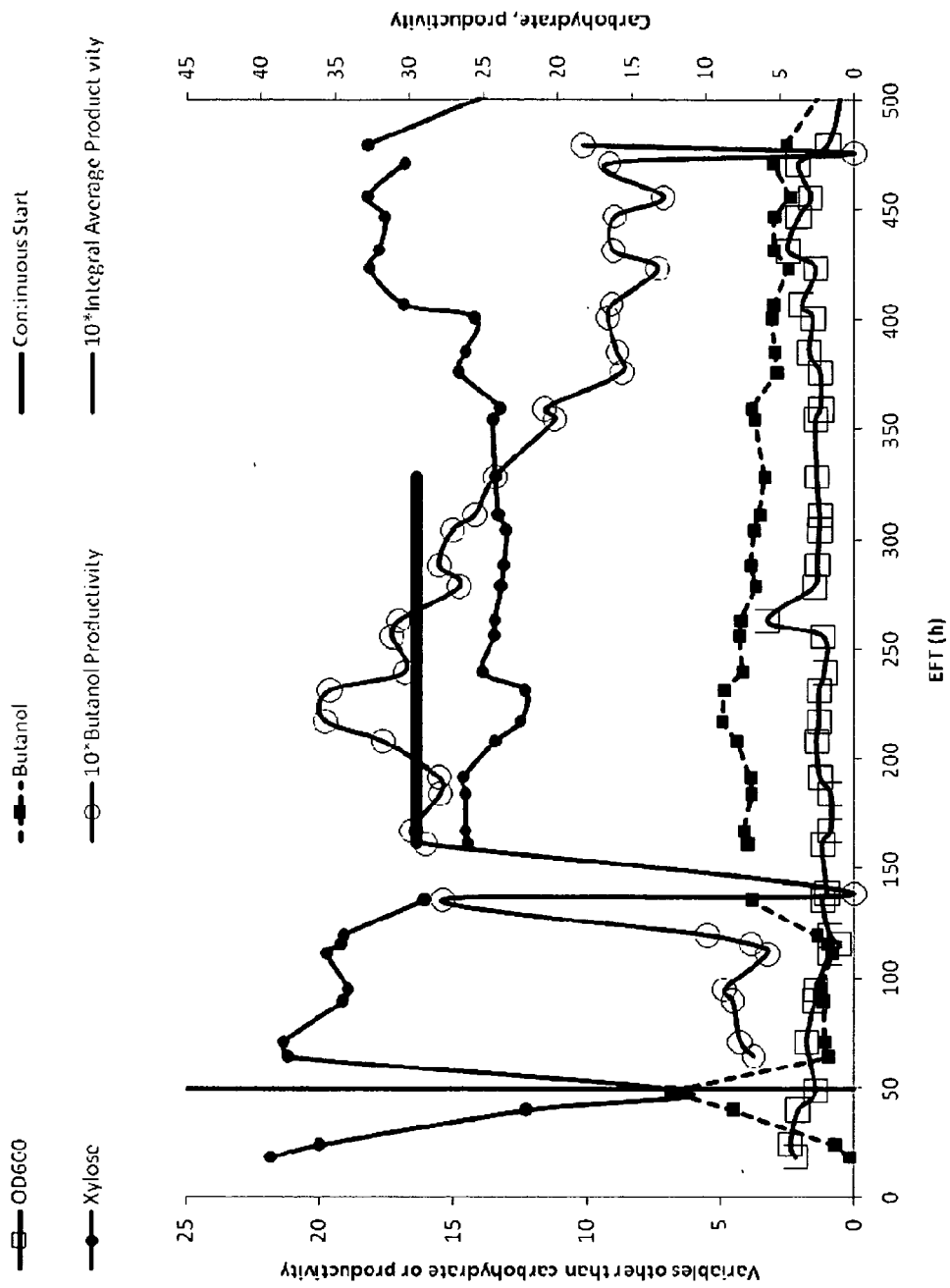
FIG. 26 shows the experimental traces of data obtained during continuous fermentation of Co-5673 in a 1000 mL immobilized cell bioreactor.

FIG. 26 shows a graph of data generated from monitoring continuous fermentation run of Co-7449 in 1000 mL immobilized cell bioreactor containing bonechar as the support at 33° C. (Run no. 2009023). The substrate was 4% xylose and the dilution rate was 0.76/h. The solid straight horizontal black line running through the butanol productivity trace is the integral average of the butanol productivity data using trapezoidal rule for the time period indicated by the horizontal black line.

FIG. 27 is a table showing the dilution rate, butanol titer (g/L), yield of butanol (g butanol/g substrate), and the productivity of butanol (g/L/h) for each of the continuous fermentation runs in FIGS. 22-26. Numbers with an asterisk (*) were calculated using integral average using trapezoidal rule for the time period shown by the horizontal black line on respective graphs (FIG. 24-26). These time periods are representative of a steady state system. Calculations demonstrate that the results achieved with the immobilized cell packed bed bioreactors used in these experiments are scalable. Titers of at least 8-10 g/L of butanol are expected on scaled up, single stage, packed bed bioreactors with normal, non-adapted or selected strains of *C. saccharobutylicum* and *C. beijerinckii* when run at a steady state using sucrose as a feedstock. Titers of total solvents for this system with normal strains are expected to be at least 12 g/L. Titers of 8-10 g/L are expected on scaled up, single stage, packed bed bioreactors when run at a steady state with normal strains of *C. saccharobutylicum* and *C. beijerinckii* using xylose solutions, molasses, sugar cane, sugar beets or sweet sorghum juice, fruit materials, juice concentrates, corn syrup, or similar feedstocks.

Titers of butanol on the scaled up system for strains of *C. saccharobutylicum* and *C. beijerinckii* that are adapted or selected for tolerance of butanol to at least 2.5% are expected to be at least 15-20 g/L.

Example 15

Next Generation Immobilized Cell Bioreactor Design and Control

Figure 28:
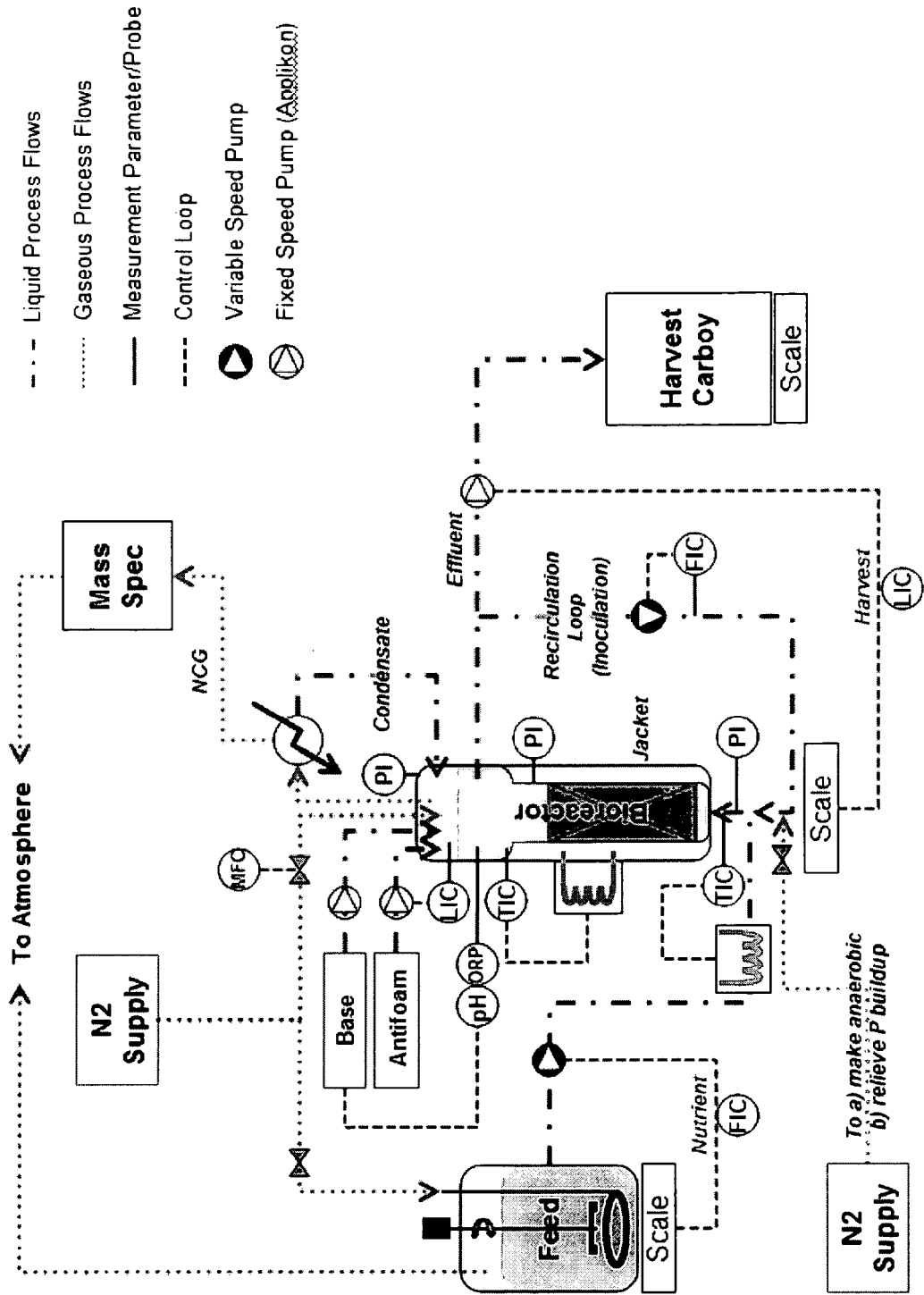
FIG. 28 is a scheme of a bench-scale immobilized cell packed bed bioreactor process design/control (with bioreactor temperature indicator control).

FIG. 28 shows a bench-scale immobilized cell bioreactor process design/control with bioreactor temperature indicator control (TIC). Here, NCG is Non-Condensable Gas, MFC is Mass Flow Controller, PI is Pressure Indicator, FIC is Flow Indicator Control. This design and control scheme is suitable for packed bed, expanded bed, and dual mode bioreactors.

Figure 29:
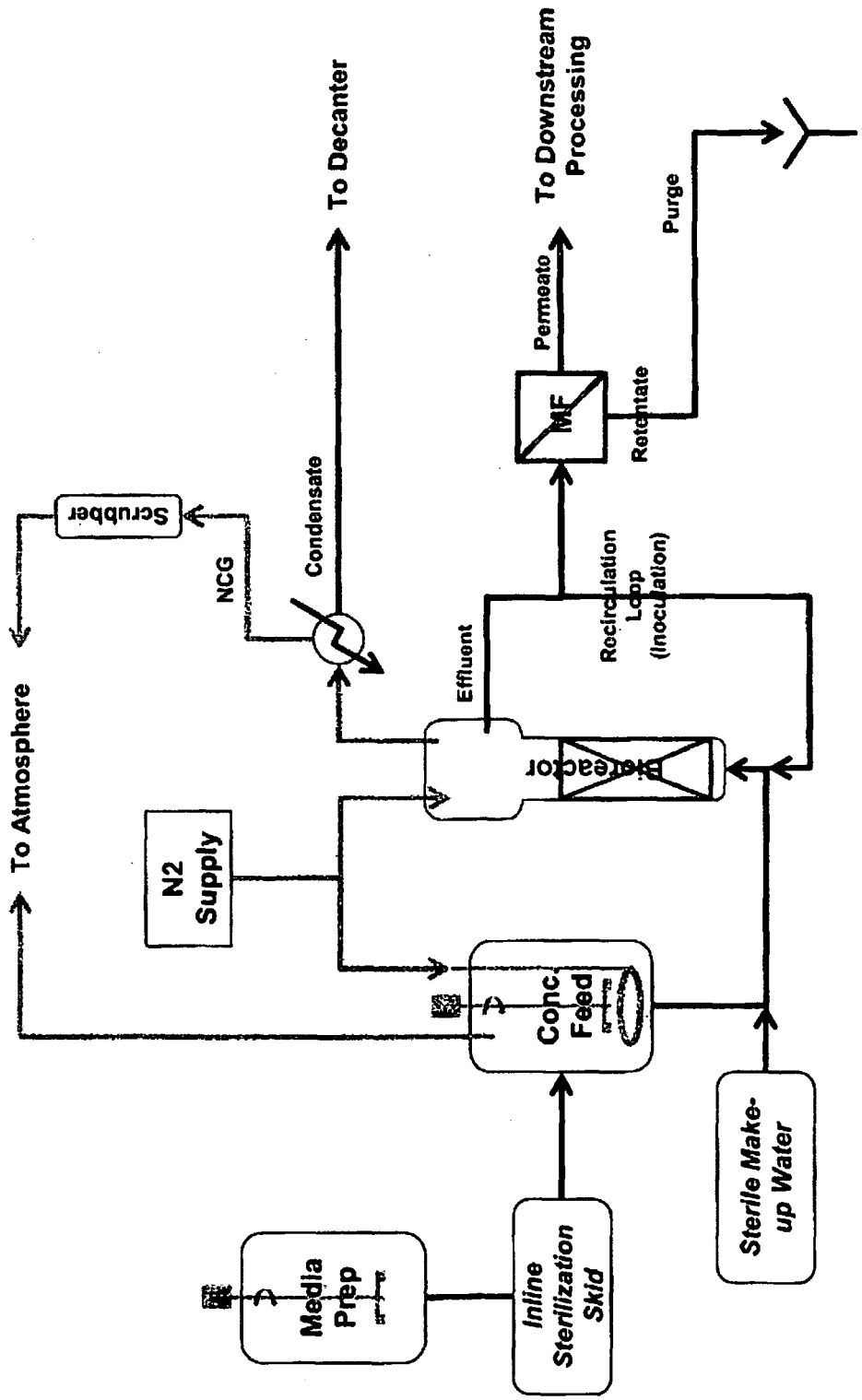
FIG. 29 is a scheme of a mini-pilot process flow—upstream processing (immobilized cell packed bed bioreactor with no harvest tank). MF stands for microfiltration such as the tangential flow filter.

FIG. 29 is a mini-pilot process flow for upstream processing (immobilized cell bioreactor with no harvest tank). Here, MF stands for microfiltration such as the tangential flow filter. This process flow scheme is suitable for packed bed, expanded bed, and dual mode bioreactors.

Example 16

Use of a Dual Mode Bioreactor for Continuous Fermentation of Immobilized Cells

A dual mode bioreactor with a H:Hp of 1.2 is packed with 20×60 sized bonechar, pressure tested and sterilized in place with steam. Following cool down, the bioreactor is connected to a packed bed bioreactor that has a butanol producing strain of *Clostridium* absorbed onto bonechar solid support. A recirculation loop is run between the two bioreactors wherein the effluent from the packed bed bioreactor is run through the inlet of the dual mode bioreactor and the effluent of the dual mode bioreactor is returned to the packed bed bioreactor through the inlet of this bioreactor. The recirculation loop is run for 24 hours. Shed cells and cells on small solid support from the packed bed bioreactor colonize the virgin support in the dual mode bioreactor.

Following the inoculation period, the recirculation loop is disconnected and a feed line is installed in its place. The pressure drop across the packed bed reads higher than desired. The fluid flow is increased 40% in an incremental manner to exceed the U$_{mf}$ of the largest particles of the solid support. After holding the fluid rate for 10 minutes, the fluid flow rate is reduced step-wise back down to the initial feed rate. The back pressure in the system drops down to an acceptable pressure reading after the support material repacks itself.

The culture is run in packed bed mode for 240 hours without incident, but as a preventative measure the fluid flow is again increased as before 40% incrementally and held for 10 minutes. The flow rate is then reduced step-wise back to the initial feed rate.

After a further 92 hours of continuous fermentation in packed bed mode, back pressure builds, so the fluid flow is increased incrementally to 40% of the initial rate, held for 10 minutes and then incrementally reduced to the initial operating flow rate. The pressure increase is only partially alleviated. The fluid flow rate is then increased incrementally to the level where the smallest particles are carried to the top of the expanded bed zone. The fluid flow rate is held for 30 minutes and then stepped back down to the initial rate plus 20%. The perfusion rate is judged adequate and the flow rate is kept at this rate for the next 238 hours. Bioreactor operation at the top fluid flow rate that keeps the smallest particles in the expanded bed zone, however insoluble particles are blown out from the column and settle out in the effluent holding tank. The fermentation run is terminated after 594 hours.

What is claimed is:

1. A system for making a solvent or organic acid, comprising a bioreactor that comprises:
   a) growth medium in contact with a solid or semi-solid support; and
   b) product tolerant microorganisms of the *Clostridium* genus on the solid or semi-solid support, wherein said microorganisms produce the solvent or organic acid and have previously been mutagenized and selected for tolerance to the solvent or organic acid on a solid or semi-solid support in the presence of the solvent or organic acid, wherein the tolerance of the selected microorganisms to the solvent or organic acid is greater on a solid or semi-solid support than the tolerance to the solvent or organic acid exhibited when the selected microorganisms are cultured in a liquid media, and wherein the microorganisms have been selected to exhibit at least 125% tolerance to the solvent or organic acid in comparison to the tolerance of corresponding non-mutagenized microorganisms.

2. The system of claim 1, wherein the microorganisms are cultured in a continuous culture.

3. The system of claim 2, further comprising the recycle and reutilization of fermentation broth nutrients and minerals recovered during product purification.

4. A system according to claim 1, wherein the bioreactor is a packed bed or fluidized bed bioreactor.

5. A system according to claim 1, wherein the bioreactor comprises:
   a) a packed bed zone, said packed bed zone adapted to hold a solid support;
   b) a bed expansion zone coupled to said packed bed zone, said bed expansion zone adapted to hold said solid support when said bioreactor is operated in an expanded bed mode; and
   c) a particle disengagement zone coupled to said bed expansion zone, said particle disengagement zone adapted to prevent egress of said solid support from said bioreactor.

6. A system according to claim 5, wherein the bioreactor further comprises an inlet distribution zone coupled to the packed bed zone.

7. A system according to claim 6, wherein the bioreactor has a pressure drop in the inlet distribution zone that is no more than 30% of the total pressure drop across the length of the bioreactor.

8. A system according to claim 5, wherein the diameter of the particle disengagement zone is larger than the diameter of the packed bed zone or the expanded bed zone.

9. A system according to claim 1, comprising at least two bioreactors arranged in series or parallel.

10. A system according to claim 9, wherein the solid or semi-solid support is within at least one of the at least two of the bioreactors.

11. A system according to claim 9, wherein at least one of the at least two bioreactors comprises a continuous culture.

12. A system according to claim 1, wherein the solvent or organic acid is butanol.

13. A system according to claim 1, wherein the microorganisms on the solid or semi-solid support comprise a biofilm.

14. A system according to claim 1, wherein the microorganisms of the *Clostridium* genus comprise *Clostridium acetobutylicum, Clostridium beijerinckii, Clostridium puniceum, Clostridium saccharobutylicum, Clostridium aurantibutyricum, Clostridium tetanomorphum, Clostridium thermosaccharolyticum, Clostridium butyricum, Clostridium cellulolyticum, Clostridium phytofermentans, Clostridium saccharoperbutylacetonicum, Clostridium thermomorphum, Clostridium thermobutyricum, Clostridium thermocellum*, or *Clostridium pasteurianum*.

15. A system according to claim 1, wherein the solid or semi-solid support in the bioreactor comprises a porous material.

16. A system according to claim 1, wherein the solid or semi-solid support in the bioreactor comprises a material selected from bone char, synthetic polymers, natural polymers, inorganic materials, or organic materials.

17. A system according to claim 14, wherein the microorganisms of the *Clostridium* genus comprise *Clostridium acetobutylicum, Clostridium saccharobutylicum*, or *Clostridium beijerinckii*.

18. A system according to claim 1, wherein the bioreactor comprises a packed bed zone, said packed bed zone adapted to hold a solid support, wherein the bioreactor further comprises an inlet distribution zone coupled to the packed bed zone and wherein the bioreactor has a pressure drop in the inlet distribution zone that is no more than 30% of the total pressure drop across the length of the bioreactor.

19. A method for making a solvent or organic acid in a system according to claim 1, comprising:
   culturing the product tolerant microorganisms of the *Clostridium* genus on the solid or semi-solid support under product producing conditions in the bioreactor.

20. The method of claim 19 wherein the *Clostridium* species is *Clostridium acetobutylicum, Clostridium saccharobutylicum* or *Clostridium beijerinckii*.

21. The method of claim 19, wherein the solvent or organic acid is butanol.

22. The method of claim 21, wherein the microorganisms exhibit tolerance to at least 2% butanol.

23. The method of claim 19, wherein the microorganisms are immobilized on the solid or semi-solid support.

24. The method of claim 23, wherein immobilizing the mutagenized and selected microorganisms on the solid or semi-solid support comprises circulating fermentation media containing the mutagenized and selected cells through the bioreactor.

25. The method of claim 23 wherein the solid or semi-solid support in the bioreactor comprises a porous material.

26. The method of claim 23 wherein the solid or semi-solid support in the bioreactor comprises a material selected from bone char, synthetic polymers, natural polymers, inorganic materials, or organic materials.

27. The method of claim 19 wherein the microorganisms are cultured in batch, fed-batch, or continuous culture.

28. The method of claim 19, wherein the solvent or organic acid is butanol and the *Clostridium* microorganisms are cultured under conditions that provide for a butanol productivity of at least 6 g/L/hr.

29. The method of claim 19, wherein the microorganisms comprise a heterologous gene.

30. The method of claim 29, wherein the heterologous gene encodes an enzyme in a product biosynthetic pathway.

31. The method of claim 30, wherein the enzyme is selected from phosphotransacetylase, acetate kinase, NAD-dependent beta-hydroxybutyryl-CoA dehydrogenase, butyryl-CoA dehydrogenase, 3-hydroxybutyryl-COA dehydratase, acetyl-CoA acetyltransferase, butyrate kinase, phosphate butyryltransferase, NADH-dependent butanol dehydrogenase B, NADH-dependent butanol dehydrogenase A, aldehyde-alcohol dehydrogenase, acetyl coenzyme A acetyltransferase, aldehyde dehydrogenase, butyrate-acetoacetate COA- transferase subunit A, butyrate-acetoacetate COA-transferase subunit B, and acetoacetate decarboxylase.

32. A method of making a solvent or organic acid according to claim 19,
wherein the bioreactor comprises:
a) a packed bed zone, comprising solid support therein, said solid support comprising said product tolerant microorganisms;
b) a bed expansion zone coupled to said packed bed zone adapted for containing said solid support when said bioreactor is operated in an expanded bed mode; and
c) a particle disengagement zone coupled to said bed expansion zone, said particle disengagement zone adapted to prevent egress of said solid support from said bioreactor.

33. A method according to claim 23, wherein the microorganisms form a biofilm on the solid or semi-solid support.

34. A method according to claim 19, further comprising harvesting the solvent or organic acid.

35. A method according to claim 19, wherein the bioreactor comprises a packed bed zone, said packed bed zone adapted to hold a solid support, wherein the bioreactor further comprises an inlet distribution zone coupled to the packed bed zone and wherein the bioreactor has a pressure drop in the inlet distribution zone that is no more than 30% of the total pressure drop across the length of the bioreactor.

36. A method according to claim 19, wherein the microorganisms of the *Clostridium* genus comprise *Clostridium acetobutylicum, Clostridium beijerinckii, Clostridium puniceum, Clostridium saccharobutylicum, Clostridium aurantibutyricum, Clostridium tetanomorphum, Clostridium thermosaccharolyticum, Clostridium butyricum, Clostridium cellulolyticum, Clostridium phytofermentans, Clostridium saccharoperbutylacetonicum, Clostridium thermomorphum, Clostridium thermobutyricum, Clostridium thermocellum*, or *Clostridium pasteurianum*.

37. The method of claim 36, wherein harvesting of the product comprises continuously extracting the product from the culture.

38. The method of claim 36, wherein harvesting of the product is performed with the use of a stripping gas, solvent, absorbent material, pervaporation membrane, or distillation.

* * * * *